United States Patent
Jackson et al.

(10) Patent No.: US 7,488,824 B2
(45) Date of Patent: Feb. 10, 2009

(54) PROCESS FOR THE PRODUCTION OF SUBSTITUTED NICOTINIC ACID ESTERS

(75) Inventors: David Anthony Jackson, Muenchwilen (CH); Martin Charles Bowden, West Yorkshire (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 299 days.

(21) Appl. No.: 10/547,840

(22) PCT Filed: Mar. 5, 2004

(86) PCT No.: PCT/EP2004/002291

§ 371 (c)(1), (2), (4) Date: Sep. 6, 2005

(87) PCT Pub. No.: WO2004/078729

PCT Pub. Date: Sep. 16, 2004

(65) Prior Publication Data

US 2006/0199964 A1    Sep. 7, 2006

(30) Foreign Application Priority Data

Mar. 7, 2003   (CH) ................................ 373/03

(51) Int. Cl.
| | |
|---|---|
| C07D 401/00 | (2006.01) |
| C07D 417/00 | (2006.01) |
| C07D 211/70 | (2006.01) |
| C07D 405/00 | (2006.01) |
| C07D 411/00 | (2006.01) |
| C07D 413/00 | (2006.01) |
| C07C 69/73 | (2006.01) |

(52) U.S. Cl. ................ 544/333; 546/268.7; 546/315; 546/282.4; 546/280.4; 546/276.1; 546/268.1; 546/272.1; 546/284.4; 546/282.1; 560/183

(58) Field of Classification Search ............... 544/333; 546/250, 268.7, 315, 282.4, 280.4, 276.1, 546/268.1, 284.4, 282.1; 560/183
See application file for complete search history.

(56) References Cited

FOREIGN PATENT DOCUMENTS

| EP | 1340747 | 9/2003 |
|---|---|---|
| JP | 2001158774 | 6/2001 |
| WO | WO 0039094 | 7/2000 |
| WO | WO 0194339 | 12/2001 |

OTHER PUBLICATIONS

Bottorff, E.M.; Jones R.G., Kornfeld, E C; Mann M J: "Pyridine Syntheses I Some Reactions of "Ene Amines" with 1,3,-dicarbonyl derivatives" Journal of the American Chemical Society, vol. 73, 1951, pp. 4380-4383, XP002286147 (last reaction on p. 4383).

*Primary Examiner*—Janet L Andres
*Assistant Examiner*—Binta M Robinson
(74) *Attorney, Agent, or Firm*—William A. Teoli, Jr.

(57) ABSTRACT

The present invention relates to a process for the preparation of compounds of formula (I) wherein the substituents are as defined in claim 1, by reaction of a compound of formula (II) wherein $R_3$ is $C_1$-$C_8$alkyl or $C_3$-$C_6$cycloalkyl and $R_4$ and $R_{05}$ are as defined for formula (I), with a compound of formula (III) wherein R, $R_1$, $R_2$ and $X_1$, are as defined for formula (I) in claim 1, in an inert solvent in the presence of a proton source.

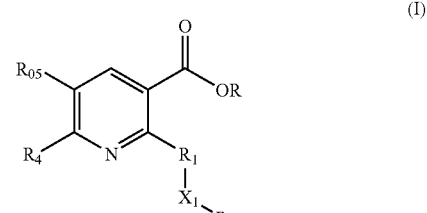

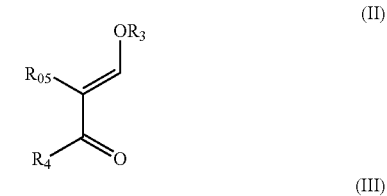

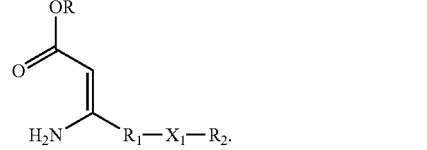

3 Claims, No Drawings

PROCESS FOR THE PRODUCTION OF SUBSTITUTED NICOTINIC ACID ESTERS

This application is a 371 of International Application No. PCT/EP2004/002291 filed Mar. 5, 2004, which claims priority to CH 373/03 filed Mar. 7, 2003, the contents of which are incorporated herein by reference.

The present invention relates to a novel process for the preparation of 6-haloalkyl-3-nicotinic acid esters and also to novel enamine intermediates for use in that process.

6-Haloalkyl-3-nicotinic acid esters are valuable intermediates for the preparation of herbicides such as those described, for example, in WO 01/94339.

From Heterocycles, Vol. 48, No. 4, 1998, pages 779-785 it is known to prepare 6-trifluoro-3-nicotinic acid ethyl esters substituted by aryl in the 4-position, corresponding to formula A, by means of dehydrogenation and subsequent oxidation of the compound of formula B in accordance with the following scheme

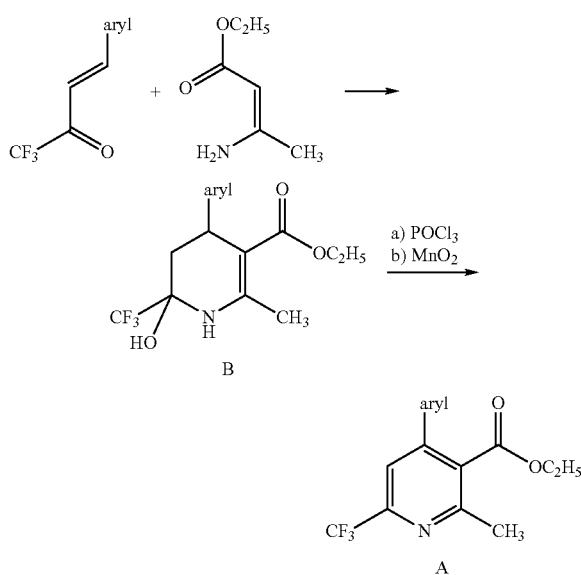

As a result of the uneconomic multi-step procedure, that process is not well suited to the large-scale preparation of 6-haloalkyl-3-nicotinic acid ethyl esters.

According to Heterocycles, Vol. 46, 1997, pages 129-132, 6-trifluoro-3-nicotinic acid methyl esters substituted by phenyl or alkyl in the 2-position, corresponding to formula C,

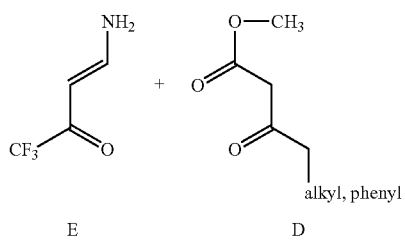

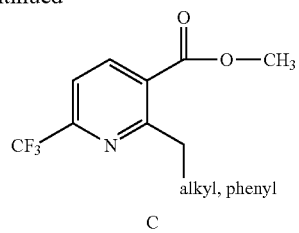

can be prepared by reacting a compound of formula E with a compound of formula D in benzene and in the presence of trifluoroacetic acid. In addition to unsatisfactory yields, that process has the serious disadvantage for large-scale preparation that the quality of the enamine (E) used as starting material continuously deteriorates during storage as a result of polymerisation reactions, making it considerably more difficult to ensure a consistent product quality.

The problem of the present invention is consequently to make available a novel process for the preparation of 6-haloalkyl-3-nicotinic acid esters which makes it possible to prepare those compounds at reasonable cost, in high yields and with good quality.

The present invention accordingly relates to a process for the preparation of compounds of formula I

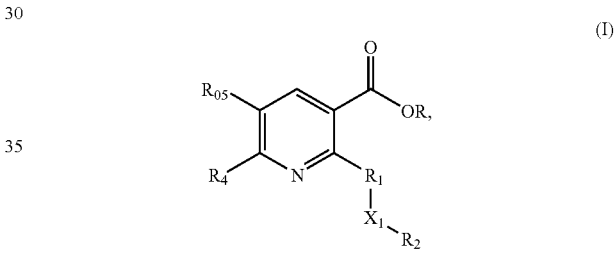

wherein

R is $C_1$-$C_6$alkyl;

$R_{05}$ is Hydrogen, $C_1$-$C_3$alkyl, $C_1$-$C_3$haloalkyl or $C_1$-$C_3$alkyl-$C_1$-$C_3$alkoxy;

$R_1$ is a $C_1$-$C_6$alkylene, $C_3$-$C_6$alkenylene or $C_3$-$C_6$alkynylene chain which may be substituted one or more times by halogen and/or by $R_5$, the unsaturated bonds of the chain not being attached directly to the substituent $X_1$;

$R_4$ is $C_1$-$C_4$haloalkyl;

$X_1$ is oxygen, —O(CO)—, —(CO)O—, —O(CO)O—, —N($R_6$)—O—, —O—N$R_{17}$—, thio, sulfinyl, sulfonyl, —SO$_2$NR$_7$—, —NR$_{18}$SO$_2$—, —N(SO$_2$R$_{18a}$)—, —N(R$_{18b}$)C(O)— or —NR$_8$—;

$R_{18a}$ is $C_1$-$C_6$alkyl;

$R_2$ is hydrogen or $C_1$-$C_8$alkyl, or is a $C_1$-$C_8$alkyl, $C_3$-$C_6$alkenyl or $C_3$-$C_6$alkynyl group which may be substituted one or more times by substituents selected from halogen, hydroxy, amino, formyl, nitro, cyano, mercapto, carbamoyl, $C_1$-$C_6$alkoxy, $C_1$-$C_6$alkoxycarbonyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, halo-substituted $C_3$-$C_6$cycloalkyl, $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkoxy-$C_1$-$C_6$alkoxy-$C_1$-$C_6$alkoxy, $C_1$-$C_6$alkylthio-$C_1$-$C_6$alkoxy, $C_1$-$C_6$alkylsulfinyl-$C_1$-$C_6$alkoxy, $C_1$-$C_6$alkylsulfonyl-$C_1$-

$C_6$alkoxy, $C_1$-$C_6$alkoxycarbonyl-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, oxiranyl (which may in turn be substituted by $C_1$-$C_6$alkyl), (3-oxetanyl)oxy (which may in turn be substituted by $C_1$-$C_6$alkyl), benzyloxy, benzylthio, benzylsulfinyl, benzylsulfonyl, $C_1$-$C_6$alkylamino, di($C_1$-$C_6$alkyl)amino, $R_9$S(O)$_2$O—, $R_{10}$N($R_{11}$)SO$_2$—, rhodano, phenyl, phenoxy, phenylthio, phenylsulfinyl and phenylsulfonyl; it being possible for the phenyl- or benzyl-containing groups to be in turn substituted by one or more $C_1$-$C_6$alkyl, $C_1$-$C_6$haloalkyl, $C_1$-$C_6$alkoxy, $C_1$-$C_6$haloalkoxy, halogen, cyano, hydroxy or nitro groups, or $R_2$ is phenyl which may be substituted one or more times by $C_1$-$C_6$alkyl, $C_1$-$C_6$haloalkyl, $C_1$-$C_6$alkoxy, $C_1$-$C_6$haloalkoxy, halogen, cyano, hydroxy or by nitro; or $R_2$ is $C_3$-$C_6$cycloalkyl, $C_1$-$C_6$alkoxy- or $C_1$-$C_6$alkyl-substituted $C_3$-$C_6$cycloalkyl, 3-oxetanyl or $C_1$-$C_6$alkyl-substituted 3-oxetanyl; or $R_2$ is a three- to ten-membered, monocyclic or fused bicyclic, ring system which may be aromatic, partially saturated or fully saturated and may contain from 1 to 4 hetero atoms selected from nitrogen, oxygen, sulfur, and/or may contain the group —C(=O)—, —C(=S)—, —C(=NR$_{19}$)—, —(N=O)—, —S(=O)— or —SO$_2$—, the ring system being attached to the substituent $X_1$ either directly or by way of a $C_1$-$C_4$alkylene, $C_2$-$C_4$alkenylene, $C_2$-$C_4$alkynylene, —N($R_{12}$)—$C_1$-$C_4$alkylene, —O—$C_1$-$C_4$alkylene, —S—$C_1$-$C_4$alkylene, —SO—$C_1$-$C_4$alkylene or —SO$_2$—$C_1$-$C_4$alkylene group and each ring system containing no more than 2 oxygen atoms and no more than two sulfur atoms, and it being possible for each ring system itself to be substituted one or more times by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, amino, hydroxy, $C_1$-$C_6$alkylthio, $C_1$-$C_6$haloalkylthio, $C_3$-$C_6$-alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$-alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano, nitro or by phenyl, it being possible for the phenyl group to be in turn substituted by hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$-haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano or by nitro, and the substituents on nitrogen in a heterocyclic ring being other than halogen;

$R_5$ is hydroxy, $C_1$-$C_6$alkoxy, $C_3$-$C_6$cycloalkyloxy, $C_1$-$C_6$alkoxy-$C_1$-$C_6$alkoxy, $C_1$-$C_6$alkoxy-$C_1$-$C_6$alkoxy-$C_1$-$C_6$alkoxy or $C_1$-$C_2$alkylsulfonyloxy;

$R_6$, $R_7$, $R_8$, $R_9$, $R_{10}$, $R_{11}$, $R_{12}$, $R_{17}$, $R_{18}$ and $R_{18b}$ are each independently of the others hydrogen, $C_1$-$C_6$alkyl, $C_1$-$C_6$haloalkyl, $C_1$-$C_6$alkoxycarbonyl, $C_1$-$C_6$alkylcarbonyl, $C_1$-$C_6$-alkoxy-$C_1$-$C_6$alkyl, $C_1$-$C_6$alkoxy-$C_1$-$C_6$alkyl substituted by $C_1$-$C_6$alkoxy, benzyl, or phenyl, it being possible for phenyl and benzyl to be in turn substituted one or more times by $C_1$-$C_6$alkyl, $C_1$-$C_6$haloalkyl, $C_1$-$C_6$alkoxy, $C_1$-$C_6$haloalkoxy, halogen, cyano, hydroxy or by nitro; $R_6$ not being hydrogen when $R_9$ is hydrogen, $C_1$-$C_6$alkoxycarbonyl or $C_1$-$C_6$alkylcarbonyl;

or the group —$R_1$—$X_1$—$R_2$ together is $C_1$-$C_6$alkyl, $C_2$-$C_6$alkenyl, $C_2$-$C_6$haloalkenyl, $C_2$-$C_6$-alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkyl, $C_1$-$C_6$haloalkylthio, $C_1$-$C_6$haloalkylsulfinyl, $C_1$-$C_6$haloalkylsulfonyl, $C_1$-$C_6$alkoxycarbonyl, $C_1$-$C_6$alkylcarbonyl, $C_1$-$C_6$alkylamino, di($C_1$-$C_6$alkyl)amino, $C_1$-$C_6$alkylaminosulfonyl, di($C_1$-$C_6$alkyl)aminosulfonyl, —NH—S—$R_{13}$, —N—($C_1$-$C_4$alkylthio)-$R_{13}$, —NH—SO—$R_{14}$, —N—($C_1$-$C_4$alkylsulfonyl)-$R_{14}$, —NH—SO$_2$—$R_{15}$, —N—($C_1$-$C_4$alkylsulfonyl)-$R_{15}$, nitro, cyano, halogen, hydroxy, amino, formyl, rhodano-$C_1$-$C_6$-alkyl, cyano-$C_1$-$C_6$alkyl, oxiranyl, $C_3$-$C_6$alkenyloxy, $C_3$-$C_6$alkynyloxy, $C_1$-$C_6$alkoxy-$C_1$-$C_6$-alkoxy, cyano-$C_1$-$C_6$alkenyloxy, $C_1$-$C_6$alkoxycarbonyloxy-$C_1$-$C_6$alkoxy, $C_3$-$C_6$alkynyloxy, cyano-$C_1$-$C_6$alkoxy, $C_1$-$C_6$alkoxycarbonyl-$C_1$-$C_6$alkoxy, $C_1$-$C_6$alkylthio-$C_1$-$C_6$alkoxy, $C_1$-$C_6$alkoxycarbonyl-$C_1$-$C_6$alkylthio, $C_1$-$C_6$alkoxycarbonyl-$C_1$-$C_6$alkylsulfinyl, $C_1$-$C_6$alkoxycarbonyl-$C_1$-$C_6$alkylsulfonyl, $C_1$-$C_6$alkylsulfonyloxy, $C_1$-$C_6$haloalkylsulfonyloxy, phenyl, benzyl, phenoxy, phenylthio, phenylsulfinyl, phenylsulfonyl, benzylthio, benzylsulfinyl or benzylsulfonyl, it being possible for the phenyl groups to be substituted one or more times by halogen, methyl, ethyl, trifluoromethyl, methoxy or by nitro;

or the group —$R_1$—$X_1$—$R_2$ together is a three- to ten-membered, monocyclic or fused bicyclic, ring system, which may be aromatic, partially saturated or saturated and which may contain from 1 to 4 hetero atoms selected from nitrogen, oxygen and sulfur and/or may contain one or two groups selected from —C(=O)—, —C(=S)—, —C(=NR$_{20}$)—, —(N=O)—, —S(=O)— and —SO$_2$—; the ring system either being attached to the pyridine ring directly via a carbon atom or being attached to the pyridine ring via a carbon atom or via a nitrogen atom by way of a $C_1$-$C_4$alkylene, $C_2$-$C_4$alkenyl or $C_2$-$C_4$alkynyl chain, and it being possible for each ring system to contain no more than 2 oxygen atoms and no more than two sulfur atoms, and it being possible for the ring system itself to be substituted one, two- or three times by substituents selected from $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_6$haloalkynyl, $C_3$-$C_6$cycloalkyl, hydroxy, $C_1$-$C_6$alkoxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_6$alkyl)aminosulfonyl, $C_1$-$C_3$alkylene-$R_{16}$, amino, $C_1$-$C_6$alkylamino, $C_1$-$C_6$alkoxyamino, di($C_1$-$C_6$alkyl)amino, (N—$C_1$-$C_6$alkyl)-$C_1$-$C_6$alkoxyamino, halogen, cyano, nitro, phenyl, benzyloxy and benzylthio, it being possible for phenyl, benzyloxy and benzylthio to be in turn substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on a nitrogen atom in a heterocyclic ring being other than halogen;

$R_{13}$ is $N(H)$—$C_1$-$C_6$alkyl, $N(H)$—$C_1$-$C_6$alkoxy, $N$—($C_1$-$C_6$alkyl)-$C_1$-$C_6$alkyl, $N$—($C_1$-$C_6$alkyl)-$C_1$-$C_6$alkoxy, $C_1$-$C_6$alkoxy, $C_1$-$C_6$haloalkoxy, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_6$haloalkynyl, $C_3$-$C_6$cycloalkyl or phenyl, it being possible for phenyl to be in turn substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_{14}$ is $N(H)$—$C_1$-$C_6$alkyl, $N(H)$—$C_1$-$C_6$alkoxy, $N$—($C_1$-$C_6$alkyl)-$C_1$-$C_6$alkyl, $N$—($C_1$-$C_6$alkyl)-$C_1$-$C_6$alkoxy, $C_1$-$C_6$alkoxy, $C_1$-$C_6$haloalkoxy, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_6$haloalkynyl, $C_3$-$C_6$cycloalkyl or phenyl, it being possible for phenyl to be in turn substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_{15}$ is $N(H)$—$C_1$-$C_6$alkyl, $N(H)$—$C_1$-$C_6$alkoxy, $N$—($C_1$-$C_6$alkyl)-$C_1$-$C_6$alkyl, $N$—($C_1$-$C_6$alkyl)-$C_1$-$C_6$alkoxy, $C_1$-$C_6$alkoxy, $C_1$-$C_6$haloalkoxy, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_6$haloalkynyl, $C_3$-$C_6$cycloalkyl or phenyl, it being possible for phenyl to be in turn substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_{16}$ is $C_1$-$C_3$alkoxy, $C_2$-$C_4$alkoxycarbonyl, $C_1$-$C_3$alkylthio, $C_1$-$C_3$alkylsulfinyl, $C_1$-$C_3$alkylsulfonyl or phenyl, it being possible for phenyl to be in turn substituted by $C_1$-$C_3$alkyl, $C_1$-$C_3$haloalkyl, $C_1$-$C_3$alkoxy, $C_1$-$C_3$haloalkoxy, halogen, cyano or by nitro; and $R_{19}$ and $R_{20}$ are each independently of the other hydrogen, hydroxy, $C_1$-$C_6$alkyl, $C_1$-$C_6$haloalkyl, $C_1$-$C_6$alkoxy, cyano, $C_1$-$C_6$alkylcarbonyl, $C_1$-$C_6$alkoxycarbonyl or $C_1$-$C_6$alkylsulfonyl; which process comprises reacting a compound of formula II

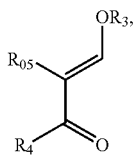

(II)

wherein $R_3$ is $C_1$-$C_8$alkyl or $C_3$-$C_6$cycloalkyl and $R_4$ and $R_{05}$ are as defined for formula I, with a compound of formula III

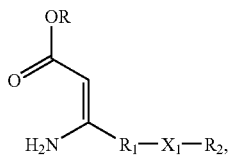

(III)

wherein R, $R_1$, $R_2$ and $X_1$ are as defined for formula I, in an inert solvent in the presence of a proton source.

The alkyl groups appearing in the substituent definitions may be straight-chained or branched and are, for example, methyl, ethyl, n-propyl, isopropyl, n-butyl, sec-butyl, isobutyl, tert-butyl, pentyl, hexyl, heptyl and octyl and also the branched isomers thereof. Alkoxy, alkenyl and alkynyl groups are derived from the mentioned alkyl groups. The alkenyl and alkynyl groups may be mono- or poly-unsaturated.

Halogen is generally fluorine, chlorine, bromine or iodine, preferably fluorine or chlorine. The same is also correspondingly true for halogen in conjunction with other meanings such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl or 2,2,2-trichloroethyl; preferably trichloromethyl, difluorochloromethyl, difluoromethyl, trifluoromethyl or dichlorofluoromethyl.

As haloalkenyl there come into consideration alkenyl groups substituted one or more times by halogen, halogen being fluorine, chlorine, bromine or iodine, especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluoro-but-2-en-1-yl. Among the $C_3$-$C_6$alkenyl groups substituted once, twice or three times by halogen, preference is given to those that have a chain length of from 3 to 5 carbon atoms.

As haloalkynyl there come into consideration alkynyl groups substituted one or more times by halogen, halogen being bromine, iodine or, especially, fluorine or chlorine, for example 3-fluoropropynyl, 3-chloropropynyl, 3-bromopropynyl, 3,3,3-trifluoropropynyl and 4,4,4-trifluoro-but-2-yn-1-yl. Among the alkynyl groups substituted one or more times by halogen, preference is given to those that have a chain length of from 3 to 5 carbon atoms.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or the pentyloxy or hexyloxy isomers; preferably methoxy or ethoxy. Alkylcarbonyl preferably is acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 8 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy; preferably difluoromethoxy, 2-chlorethoxy or trifluoromethoxy. Alkylthio groups preferably have a chain length of from 1 to 8 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl; preferably methylsulfinyl or ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl. Alkoxyalkoxy groups preferably have a chain length of from 1 to 8 carbon atoms. Examples of alkoxyalkoxy are: methoxymethoxy, methoxyethoxy, methoxypropoxy, ethoxymethoxy, ethoxyethoxy, propoxymethoxy and butoxybutoxy. Alkylamino is, for example, methylamino, ethylamino, n-propylamino, isopropylamino or the butylamine isomers. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms. Alkoxyalkyl groups preferably have a chain length of from 2 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl groups preferably have from 2 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. The cycloalkyl groups preferably have from 3 to 8 ring carbon atoms, for example cyclopropyl, cyclobutyl, cyclopentyl, cyclohexyl, cycloheptyl and cyclooctyl. Phenyl, including phenyl as part of a substituent such as phenoxy, benzyl, benzyloxy, benzoyl, phenylthio, phenylalkyl and phenoxyalkyl, may be present in substituted form, in which case the substituents may be in the ortho-, meta- and/or para-position(s). Preferred substituent positions are the positions ortho and para to the ring attachment position.

In accordance with the process according to the invention there are preferably prepared those compounds of formula I wherein $R_4$ is halomethyl or haloethyl;

$R_{05}$ is hydrogen;

$X_1$ is oxygen, —O(CO)—, —(CO)O—, —O(CO)O—, —N($R_6$)—O—, —O—N$R_{17}$—, thio, sulfinyl, sulfonyl, —SO$_2$N$R_7$—, —N$R_{18}$SO$_2$— or —N$R_8$—;

$R_2$ is hydrogen or $C_1$-$C_8$alkyl, or a $C_1$-$C_8$alkyl, $C_3$-$C_6$alkenyl or $C_3$-$C_6$alkynyl group which is substituted one or more times by halogen, hydroxy, amino, formyl, nitro, cyano, mercapto, carbamoyl, $C_1$-$C_6$alkoxy, $C_1$-$C_6$alkoxycarbonyl, $C_2$-$C_6$alkenyl, $C_2$-$C_6$haloalkenyl, $C_2$-$C_6$-alkynyl, $C_2$-$C_6$haloalkynyl, $C_3$-$C_6$cycloalkyl, halo-substituted $C_3$-$C_6$cycloalkyl, or by $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkoxy-$C_1$-$C_6$alkoxy-$C_1$-$C_6$alkoxy, $C_1$-$C_6$-alkylthio-$C_1$-$C_6$alkoxy, $C_1$-$C_6$alkylsulfinyl-$C_1$-$C_6$alkoxy, $C_1$-$C_6$alkylsulfonyl-$C_1$-$C_6$alkoxy, $C_1$-$C_6$-alkoxycarbonyl-$C_1$-$C_6$alkoxy, $C_1$-$C_6$alkoxycarbonyl, $C_1$-$C_6$alkylcarbonyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$-haloalkylsulfonyl, oxiranyl (which may in turn be substituted by $C_1$-$C_6$alkyl), or by (3-oxetanyl)oxy (which may in turn be substituted by $C_1$-$C_6$alkyl), or by benzylthio, benzylsulfinyl, benzylsulfonyl, $C_1$-$C_6$alkylamino, di($C_1$-$C_6$alkyl)amino, $R_9$S(O)$_2$O—, $R_{10}$N($R_{11}$)SO$_2$—, rhodano, phenyl, phenoxy, phenylthio, phenylsulfinyl or by phenylsulfonyl; it being possible for the phenyl- or benzyl-containing groups to be in turn substituted by one or more $C_1$-$C_6$alkyl, $C_1$-$C_6$haloalkyl, $C_1$-$C_6$alkoxy, $C_1$-$C_6$haloalkoxy, halogen, cyano, hydroxy or nitro groups, or $R_2$ is phenyl which may be substituted one or more times by $C_1$-$C_6$alkyl, $C_1$-$C_6$haloalkyl, $C_1$-$C_6$alkoxy, $C_1$-$C_6$haloalkoxy, halogen, cyano, hydroxy or by nitro; or $R_2$ is $C_3$-$C_6$cycloalkyl, $C_1$-$C_6$alkoxy- or $C_1$-$C_6$alkyl-substituted $C_3$-$C_6$cycloalkyl, 3-oxetanyl or $C_1$-$C_6$alkyl-substituted 3-oxetanyl;

or $R_2$ is a five- to ten-membered, monocyclic or fused bicyclic, ring system which may be aromatic, partially saturated or fully saturated and may contain from 1 to 4 hetero atoms selected from nitrogen, oxygen, sulfur, and/or may contain the group —C(=O)—, —C(=S)—, —C(=N$R_{19}$)—, —(N=O)—, —S(=O)— or —SO$_2$—, the ring system being attached to the substituent $X_1$ directly or by way of a $C_1$-$C_4$alkylene, $C_2$-$C_4$alkenyl-$C_1$-$C_4$alkylene, $C_2$-$C_4$alkynyl-$C_1$-$C_4$alkylene, —N($R_{12}$)—$C_1$-$C_4$alkylene, —SO—$C_1$-$C_4$alkylene or —SO$_2$—$C_1$-$C_4$alkylene group and each ring system containing no more than 2 oxygen atoms and no more than two sulfur atoms, and it being possible for each ring system itself to be substituted one or more times by $C_1$-$C_6$alkyl, $C_1$-$C_6$haloalkyl, $C_2$-$C_6$alkenyl, $C_2$-$C_6$haloalkenyl, $C_2$-$C_6$-alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, amino, hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano, nitro or by phenyl, it being possible for the phenyl group to be in turn substituted by hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$-alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano or by nitro, and the substituents on nitrogen in a heterocyclic ring being other than halogen;

$R_6$, $R_7$, $R_8$, $R_9$, $R_{10}$ $R_{11}$, $R_{12}$, $R_{17}$ and $R_{18}$ are each independently of the others hydrogen, $C_1$-$C_6$alkyl, $C_1$-$C_6$haloalkyl, $C_1$-$C_6$alkoxycarbonyl, $C_1$-$C_6$alkylcarbonyl, $C_1$-$C_6$alkoxy-$C_1$-$C_6$alkyl, $C_1$-$C_6$alkoxy-$C_1$-$C_6$alkyl substituted by $C_1$-$C_6$alkoxy, benzyl, or phenyl, it being possible for phenyl and benzyl to be in turn substituted one or more times by $C_1$-$C_6$alkyl, $C_1$-$C_6$haloalkyl, $C_1$-$C_6$alkoxy, $C_1$-$C_6$haloalkoxy, halogen, cyano, hydroxy or by nitro; $R_6$ not being hydrogen when $R_9$ is hydrogen, $C_1$-$C_6$alkoxycarbonyl or $C_1$-$C_6$alkylcarbonyl;

or the group —$R_1$—$X_1$—$R_2$ together is $C_1$-$C_6$alkyl, $C_2$-$C_6$alkenyl, $C_2$-$C_6$haloalkenyl, $C_2$-$C_6$-alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkyl, $C_1$-$C_6$haloalkylthio, $C_1$-$C_6$haloalkylsulfinyl, $C_1$-$C_6$haloalkylsulfonyl, $C_1$-$C_6$alkoxycarbonyl, $C_1$-$C_6$alkylcarbonyl, $C_1$-$C_6$alkylamino, di($C_1$-$C_6$alkyl)amino, $C_1$-$C_6$alkylaminosulfonyl, di($C_1$-$C_6$alkyl)aminosulfonyl, —NH—S—$R_{13}$, —N—($C_1$-$C_4$alkylthio)-$R_{13}$, —NH—SO—$R_{14}$, —N—($C_1$-$C_4$alkylsulfonyl)-$R_{14}$, —NH—SO$_2$—$R_{15}$, —N—($C_1$-$C_4$alkylsulfonyl)-$R_{15}$, nitro, cyano, halogen, hydroxy, amino, formyl, rhodano-$C_1$-$C_6$alkyl; cyano-$C_1$-$C_6$alkyl, oxiranyl, $C_3$-$C_6$alkenyloxy, $C_3$-$C_6$alkynyloxy, $C_1$-$C_6$alkoxy-$C_1$-$C_6$alkoxy, cyano-$C_1$-$C_6$alkenyloxy, $C_1$-$C_6$alkoxycarbonyloxy-$C_1$-$C_6$alkoxy, $C_3$-$C_6$alkynyloxy, cyano-$C_1$-$C_6$alkoxy, $C_1$-$C_6$alkoxycarbonyl-$C_1$-$C_6$alkoxy, $C_1$-$C_6$alkylthio-$C_1$-$C_6$alkoxy, alkoxycarbonyl-$C_1$-$C_6$alkylthio, alkoxycarbonyl-$C_1$-$C_6$alkylsulfinyl, alkoxycarbonyl-$C_1$-$C_6$alkylsulfonyl, $C_1$-$C_6$alkylsulfonyloxy, $C_1$-$C_6$haloalkylsulfonyloxy, phenyl, benzyl, phenoxy, phenylthio, phenylsulfinyl, phenylsulfonyl, benzylthio, benzylsulfinyl or benzylsulfonyl, it being possible for the phenyl groups to be substituted one or more times by halogen, methyl, ethyl, trifluoromethyl, methoxy or by nitro;

or the group —$R_1$—$X_1$—$R_2$ together is a five- to ten-membered, monocyclic or fused bicyclic, ring system, which may be aromatic or partially saturated and which may contain from 1 to 4 hetero atoms selected from nitrogen, oxygen and sulfur, the ring system either being directly attached to the pyridine ring or being attached to the pyridine ring by way of a $C_1$-$C_4$alkylene group, and it being possible for each ring system to contain no more than 2 oxygen atoms and no more than two sulfur atoms, and/or to contain the group —C(=O)—, —C(=S)—, —C(=NR$_{20}$)—, —(N=O)—, —S(=O)— or —SO$_2$—; and the ring system itself may be substituted one, two or three times by $C_1$-$C_6$alkyl, $C_1$-$C_6$-haloalkyl, $C_3$-$C_6$alkenyl, $C_3$-$C_6$haloalkenyl, $C_3$-$C_6$alkynyl, $C_3$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$-haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, $C_2$-$C_4$dialkylaminosulfonyl, $C_1$-$C_3$alkylene-$R_{16}$, N(H)—$C_1$-$C_6$alkyl, N(H)—$C_1$-$C_6$alkoxy, N—($C_1$-$C_6$alkyl)-$C_1$-$C_6$alkyl, N—($C_1$-$C_6$alkyl)-$C_1$-$C_6$alkoxy, halogen, cyano, nitro, phenyl and by benzylthio, it being possible for phenyl and benzylthio to be in turn substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on nitrogen in a heterocyclic ring being other than halogen; and $R_{19}$ and $R_{20}$ are each independently of the other hydrogen, hydroxy, $C_1$-$C_6$alkyl, $C_1$-$C_6$-haloalkyl, $C_1$-$C_6$alkoxy, $C_1$-$C_6$alkylcarbonyl, $C_1$-$C_6$alkoxycarbonyl or $C_1$-$C_6$alkylsulfonyl.

The process according to the invention is especially suitable for the preparation of those compounds of formula I wherein $R_1$ is —$CH_2$—, —$CH_2CH_2$—, —$CH_2CH_2CH_2$—, —$CF_2$—, —CH=CHCH$_2$—, —CH(CH$_3$)— or —C≡CCH$_2$—, but preferably —$CH_2$—, the free valency on the left in each case being attached to the pyridine ring.

Preference is furthermore given to the preparation of those compounds of formula I wherein $X_1$ is oxygen, sulfonyl or a group —NR$_{18}$SO$_2$—, especially oxygen.

In accordance with the process according to the invention, special preference is given to the preparation of those compounds of formula I wherein $R_2$ is $CH_3$, $CH_2CH_3$, $CH_2OCH_3$, $CH_2OCH_2CH_3$, $CH_2CH_2OCH_3$, $CH_2CH_2OCH_2CH_3$, $CH_2CF_3$, propargyl, cyclopropylmethyl, benzyl, $CH_2CH_2SO_2CH_3$ or $CH_2CH_2OCH_2CH_2OCH_3$, but preferably $CH_2CH_2OCH_3$, with very special preference being given to those compounds wherein $X_1$ is oxygen and $R_1$ is —$CH_2$—.

In accordance with the process according to the invention, preference is given to the preparation of those compounds of formula I wherein $R_{05}$ is hydrogen, $CH_3$, $CH_2Cl$, $CH_2Br$ or $CH_2OCH_3$, but especially hydrogen.

From that group, those compounds wherein R is ethoxy or methoxy may be prepared especially advantageously.

Furthermore, in accordance with the process according to the invention there may be advantageously prepared compounds of formula I wherein $R_2$ is

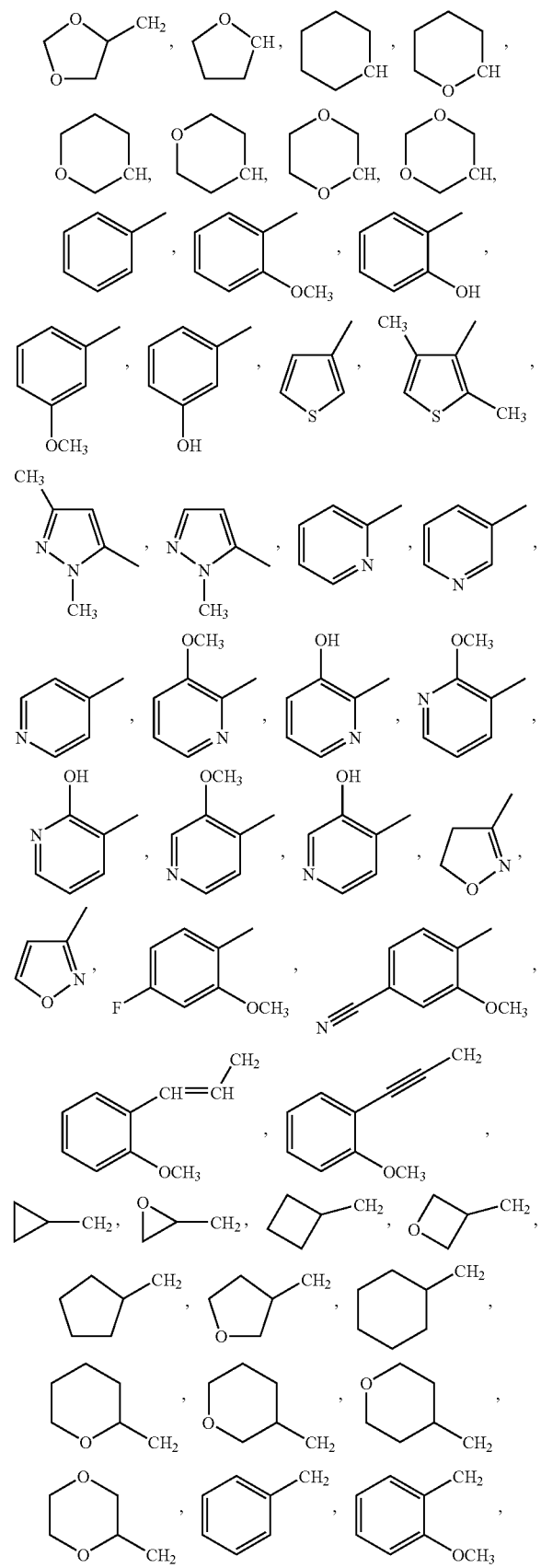

-continued

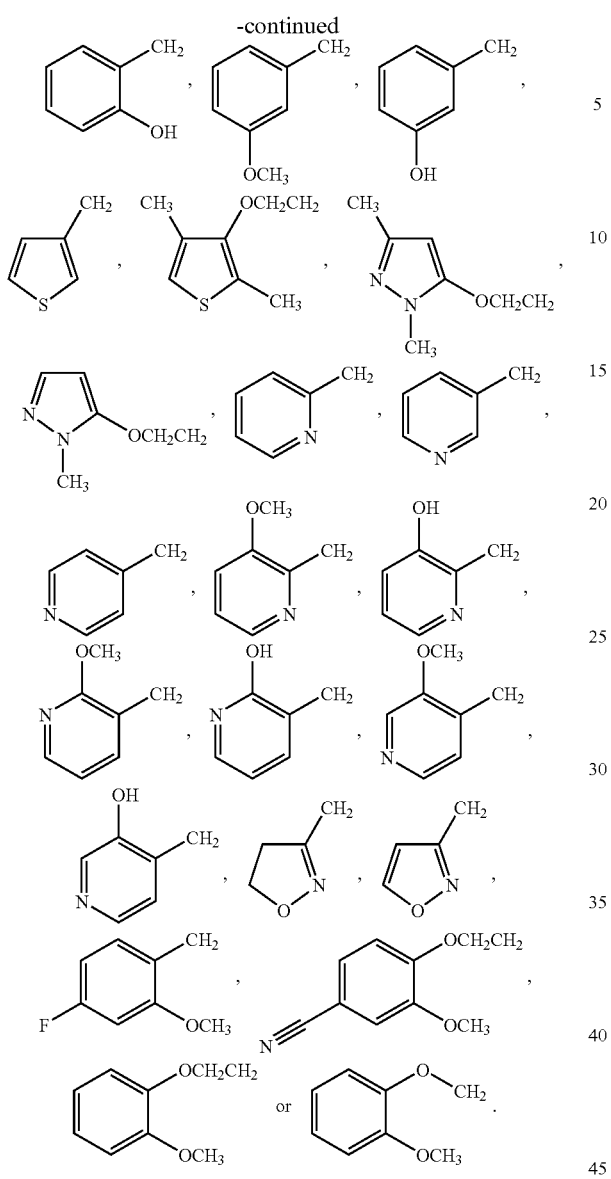

Where no free valency is indicated in those preferred meanings of $R_2$, as in the case of, for example,

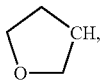

the attachment position is at the carbon atom marked "CH".

Furthermore, there may also be advantageously prepared those compounds wherein the group —$R_1$—$X_1$—$R_2$ together is a four- to ten-membered, monocyclic or fused bicyclic, ring system, which may be aromatic, partially saturated or saturated and contains from 1 to 4 hetero atoms selected from nitrogen, oxygen and sulfur and/or contains one or two groups selected from —C(=O)—, —C(=S)—, —C(=NR$_{20}$)— and —SO$_2$—, the ring system being attached to the pyridine ring via a carbon atom or preferably via a nitrogen atom by way of a $C_1$-$C_4$alkylene chain, especially a methylene chain. Among such ring systems special mention may be made of the following preferred, four- to seven-membered ring systems attached via a nitrogen atom to the methylene group, the attachment position being shown in each case at the bottom left:

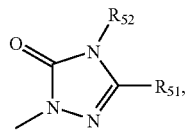 $U_{1.001}$

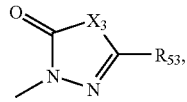 $U_{1.002}$

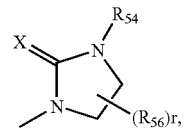 $U_{1.003}$

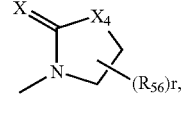 $U_{1.004}$

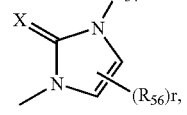 $U_{1.005}$

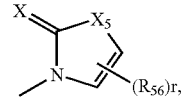 $U_{1.006}$

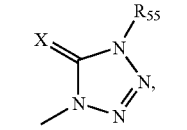 $U_{1.007}$

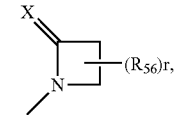 $U_{1.008}$

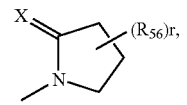 $U_{1.009}$

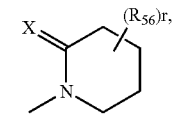 $U_{1.010}$

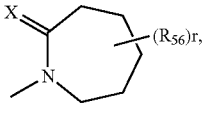 $U_{1.011}$

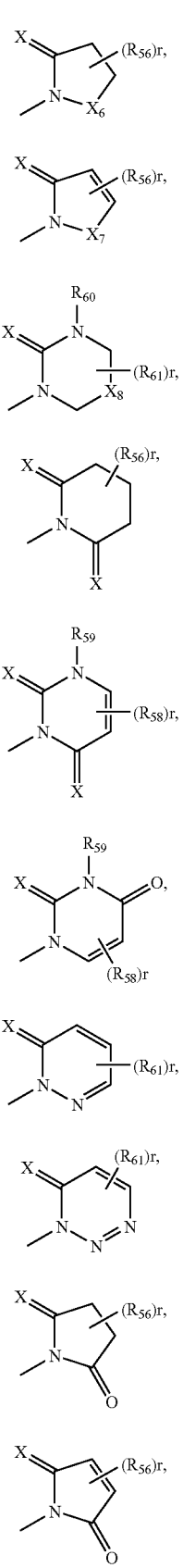
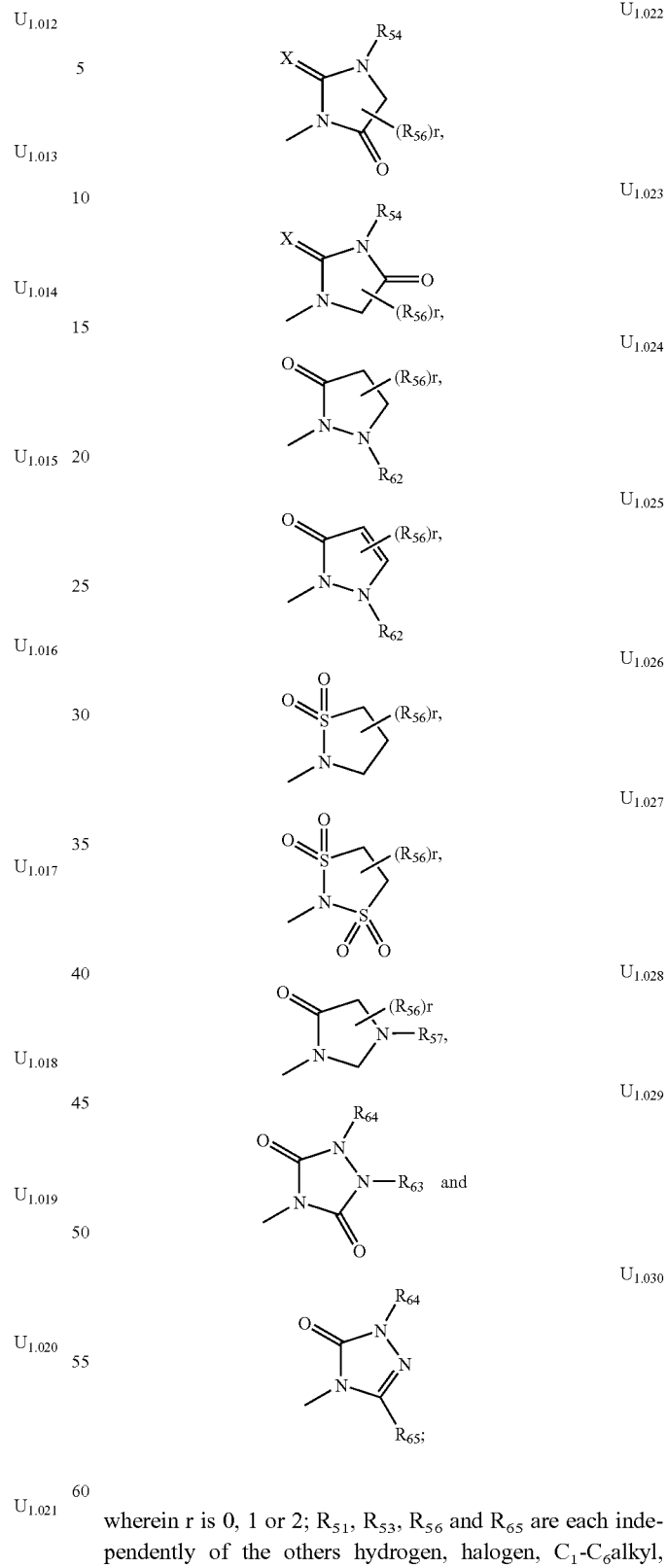
wherein r is 0, 1 or 2; $R_{51}$, $R_{53}$, $R_{56}$ and $R_{65}$ are each independently of the others hydrogen, halogen, $C_1$-$C_6$alkyl, $C_1$-$C_6$haloalkyl, $C_3$-$C_6$cycloalkyl, $C_3$-$C_6$alkenyl, $C_3$-$C_6$alkynyl, $C_1$-$C_3$alkoxy-$C_1$-$C_3$alkyl, $C_1$-$C_6$alkoxy, $C_3$-$C_6$alkenyloxy, $C_3$-$C_6$alkynyloxy, $C_1$-$C_6$alkylthio, $C_1$-$C_6$alkylsulfinyl, $C_1$-$C_6$alkylsulfonyl, $C_3$-$C_6$alkenylthio or $C_3$-$C_6$alkynylthio; $R_{52}$ is hydrogen, $C_1$-$C_6$alkyl, $C_1$-$C_6$haloalkyl, $C_3$-$C_6$cycloalkyl, $C_3$-$C_6$alkenyl, $C_3$-$C_6$alkynyl, $C_1$-$C_6$alkoxy, amino, or phenyl which may in turn be substituted by $R_{70}$; $R_{54}$, $R_{55}$ and $R_{60}$ are each independently of the others hydrogen, $C_1$-$C_6$alkyl, $C_1$-$C_6$haloalkyl, $C_3$-$C_6$alkenyl, $C_3$-$C_6$alkynyl or $C_3$-$C_6$cycloalkyl; $R_{57}$, $R_{63}$, $R_{66}$, $R_{67}$, $R_{68}$ and $R_{69}$ are each independently of the others $C_1$-$C_6$alkyl, or phenyl which may in turn be substituted by $R_{70}$; $R_{64}$ is $C_1$-$C_6$alkyl, $C_1$-$C_6$haloalkyl, $C_3$-$C_6$cycloalkyl, $C_3$-$C_6$alkenyl, $C_3$-$C_6$alkynyl, or phenyl which may in turn be substituted by $R_{70}$; $R_{58}$ and $R_{61}$ are hydrogen, halogen, $C_1$-$C_6$alkyl or $C_1$-$C_6$haloalkyl; $R_{59}$ is $C_1$-$C_6$alkyl, $C_1$-$C_6$haloalkyl, $C_1$-$C_3$alkoxy-$C_1$-$C_3$alkyl, $C_3$-$C_6$alkenyl or $C_3$-$C_6$alkynyl; $R_{62}$ is hydrogen, $C_1$-$C_6$alkyl, $C_1$-$C_4$alkoxycarbonyl or $C_1$-$C_4$alkylthiocarbonyl; or $R_{51}$ together with $R_{52}$, or $R_{54}$ together with an adjacent group $R_{56}$, or $R_{58}$ together with an adjacent group $R_{59}$, or $R_{60}$ together with an adjacent group $R_{61}$, or, when r is 2, two adjacent groups $R_{56}$ or two adjacent groups $R_{61}$ together may form a saturated or unsaturated $C_1$-$C_5$alkylene or $C_3$-$C_4$alkenylene bridge, which may in turn be substituted by a group $R_{70}$ or interrupted by oxygen, sulfur or nitrogen; each $R_{70}$ is independently halogen, $C_1$-$C_3$alkyl, $C_1$-$C_3$haloalkyl, hydroxy, $C_1$-$C_3$alkoxy, $C_1$-$C_3$haloalkoxy, cyano or nitro; X is oxygen, sulfur or $NR_6$; $X_3$, $X_4$ and $X_5$ are oxygen or sulfur; $X_6$ and $X_7$ are oxygen, sulfur, S(O) or $SO_2$; and $X_8$ is $CH_2$, oxygen, sulfur, S(O), $SO_2$ or $NR_{71}$, wherein $R_{71}$ is hydrogen or $C_1$-$C_6$alkyl.

In the context of the present invention, preference is given to the group $R_1$—$X_1$—$R_2$ together being $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy or $C_1$-$C_6$alkylthio, e.g. methyl, ethyl, n-propyl, isopropyl, cyclopropyl, n-butyl, fluoromethyl, 2-fluoroethyl, difluoroethyl, trifluoroethyl, vinyl, 1-propenyl, methoxy, ethoxy, methylthio or ethylthio.

In the context of the present invention, preference is given to R being methyl, ethyl, n-propyl or isopropyl, especially ethyl.

$R_3$ is preferably methyl or ethyl, very especially ethyl.

$R_4$ is preferably trifluoromethyl, difluoromethyl, chlorodifluoromethyl, pentafluoroethyl, 2,2,2-trifluoroethyl, especially trifluoromethyl, chlorodifluoromethyl or difluoromethyl.

As inert solvents for the method according to the invention there are suitable, for example, aromatic solvents such as benzene, chlorobenzene, fluorobenzene, xylenes, toluene, or alcohols such as methanol or ethanol, and also ethyl acetate, acetonitrile, dimethyl sulfoxide, dimethylformamide, dimethylacetamide, N-methyl-2-pyrrolidone, acetone, butanone, halogenated solvents such as, for example, methylene chloride, trichloromethane, dichloroethylene or trichlorethane, ethers such as tetrahydrofuran, diethyl ether, 1,2-dimethoxyethane, dioxane or methyl tert-butyl ether. Ethanol and toluene are especially preferred.

Organic or mineral acids are suitable as the proton source. Examples of suitable proton sources are HCl, HBr, $H_2SO_4$, carboxylic acids such as acetic acid and derivatives thereof such as trifluoroacetic acid and trichloroacetic acid, sulfonic acids such as methanesulfonic acid or p-toluenesulfonic acid and also carbonic acid. As the proton source for the process according to the invention special preference is given to trifluoroacetic acid.

The reactions can be carried out at ambient temperature or at elevated temperature. In general, addition of the reactants is carried out at a temperature from ambient temperature to the boiling point of the solvent, especially from 20 to 140° C., preferably from 40 to 120° C., with subsequent heating of the reaction mixture, advantageously to the boiling point of the solvent.

The compounds of formula II are known or are accessible by known methods. Processes for the preparation of compounds of formula II are described, for example, in J. Org Chem. (1995) vol 95, 3523, in H. Amil, T. Kobayashi, H. Terasawa, K. Uneyama, Org. Lett. 3(20), 3103-3105 (2001) and also A. Colla, G. Clar, S. Krimmer, P. Fischer, M. A. P. Martins, Synthesis-Stuttgart (6),483-486 (1991).

Some of the compounds of formula III are known. The preparation of such compounds is described in H. G. O. Becker, J. Prakt. Chem. (1961), Vol 12, 294., in WO 00/24714 and also in D. H. Wu, W. Wang, J. Labelled Compd. Rad 39(2),105-107(1997).

The compounds of formula III wherein —$R_1$—$X_1$—$R_2$ is —$CH_2$—O—$CH_2$—$CH_2$—O—$CH_3$, that is to say compounds of formula IIIa

(IIIa)

wherein R is as defined for formula III, are novel and were developed specifically for the preparation of compounds of formula I, and the present invention accordingly relates thereto. In a preferred compound of formula IIIa, R is methyl or ethyl.

Compounds of formula III can be prepared using processes known to the person skilled in the art, for example by reacting the unsaturated ketones on which they are based with ammonia gas as described in Preparation Example P1 hereinbelow.

In a preferred embodiment of the process according to the invention, the starting compounds of formula III are prepared from the 3-oxo-carboxylic acid esters on which they are based by introducing ammonia gas and then, without further isolation, reacting directly with the compounds of formula II. That process is especially advantageous for the large-scale preparation of compounds of formula I.

The compounds of formula I either may be used directly in the reaction mixture for further reactions or alternatively may be isolated. Isolation of the compounds of formula I can be carried out, for example, by extraction of the reaction mixture and subsequent removal of the solvent from the product-containing phase by customary methods.

The process according to the invention will be explained in greater detail in the following Preparation Examples:

EXAMPLE P1

Preparation of
3-amino-4-methoxyethoxy-but-2-enoic acid ethyl ester

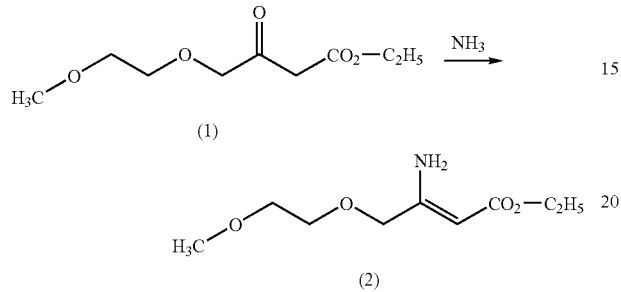

A mixture of 1.37 g (6 mmol) of 3-oxo-4-methoxyethoxy-butanoic acid ethyl ester (1) in 13 ml of ethanol is introduced into a reaction vessel and cooled to a temperature of 0° C. using an ice/water bath.

Ammonia gas is then introduced for a period of 30 minutes, with stirring, and the reaction mixture is stirred for a further 20 minutes at a temperature of 0° C. After removing the cooling bath, the reaction mixture is allowed to warm up to a temperature of 20° C. and ammonia gas is then introduced for a further hour. The reaction mixture is then stirred for 20 hours.

After removal of the solvent in vacuo, there are obtained 1.3 g (95% of theory) of 3-amino-4-methoxyethoxy-but-2-enoic acid ethyl ester (2) in the form of an orange-coloured oil.

$^1$H NMR (CDCl$_3$): 1.30 (t, 3H, C$\underline{H}_3$CH$_2$O—), 3.40 (s, 3H, C$\underline{H}_3$O—), 3.55 (m, 2H, OC$\underline{H}_2$CH$_2$O), 3.60 (m, 2H, OCH$_2$CH$\underline{H}_2$O), 4.10 (s, 2H, C=CC$\underline{H}_2$O—), 4.15 (q, 2H, CH$_3$C$\underline{H}_2$O—), 4.50 (s, 1H, C$\underline{H}$=CNH$_2$).

$^{13}$C NMR (CDCl$_3$): 14.7 (CH$_3$), 58.9 (CH$_2$), 59.2 (CH$_3$), 70.0 (CH$_2$), 71.0 (CH$_2$), 71.8 (CH$_2$), 81.9 (CH), 159.7 (C), 170.3 (C).

MS: 203 (M$^+$), 158, 157, 144, 129, 114, 100, 98, 83, 71, 59, 45.

EXAMPLE P2

Preparation of 2-methoxyethoxymethyl-3-ethoxycarbonyl-6-trifluoromethyl-pyridine (4)

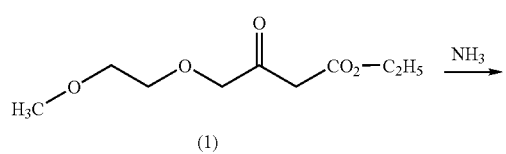

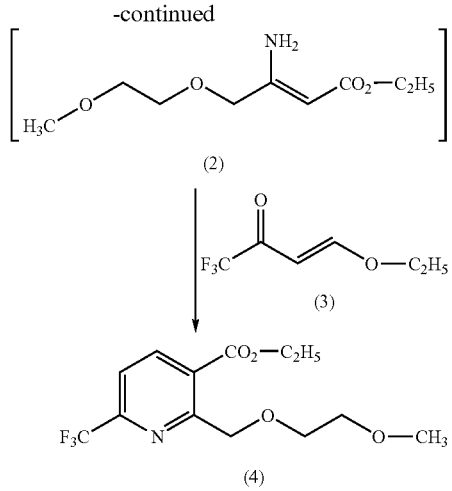

A mixture of 52.3 g (0.24 mol) of 3-oxo-4-methoxyethoxy-butanoic acid ethyl ester (1) in 150 ml of toluene is introduced into a reaction vessel equipped with a water separator.

Ammonia gas is then introduced into the reaction mixture for 2 hours, with stirring. Refluxing is then carried out for 30 minutes and the water is collected in the separator. After cooling the reaction mixture to a temperature of 20° C., the procedure is repeated. Ammonia gas is again introduced for 1.5 hours, with stirring, and the reaction mixture is then refluxed in order to separate off the water.

After cooling the reaction mixture, which contains 3-amino-4-methoxyethoxy-but-2-enoic acid ethyl ester (2), to a temperature of 20° C., 48 g (0.248 mol) of 1-ethoxy-3-oxo-4-trifluorobutene (3) are added and stirring is carried out at a temperature of 20° C. for 18 hours. 1.5 ml of trifluoroacetic acid are then added, stirring is carried out at a temperature of 20° C. for 2 hours and refluxing is carried out for a further 2 hours.

The reaction mixture is then allowed to cool down to a temperature of 20° C. and is then washed with 100 ml of 1M NaHCO$_3$. The aqueous phase is separated off and is then extracted with 150 ml of toluene and the combined organic phases are then dried over MgSO$_4$.

After removal of the solvent in vacuo, there are obtained 65.4 g (62% of theory) of 2-methoxyethoxymethyl-3-ethoxycarbonyl-6-trifluoromethylpyridine in the form of a dark-brown oil.

$^1$H NMR (CDCl$_3$): 1.40 (t, 3H, C$\underline{H}_3$CH$_2$O—), 3.35 (s, 3H, C$\underline{H}_3$O—), 3.55 (m, 2H, OC$\underline{H}_2$CH$_2$O), 3.70 (m, 2H, OCH$_2$C$\underline{H}_2$O), 4.45 (q, 2H, CH$_3$C$\underline{H}_2$O—), 5.00 (s, 2H, ArC$\underline{H}_2$O—), 7.70 (s, 1H, Ar$\underline{H}$), 8.30 (s, 1H, Ar$\underline{H}$).

MS: 307 (M$^+$), 262, 248, 233, 204, 202, 161, 128, 109, 59, 45

The other compounds listed in Table 1 can also be prepared in that manner.

In the following Table, the valency on the left of the radical R$_1$ is attached to the pyridine ring. When no free valency is indicated in the case of the substituent R$_2$, as in the case of, for example,

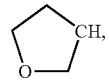

the attachment position is at the carbon atom marked "CH".

TABLE 1
Compounds of formula Ia

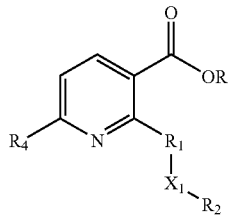

(Ib)

wherein R is methyl or ethyl:

| Comp. no. | $R_4$ | $R_1$ | $R_2$ | $X_1$ |
|---|---|---|---|---|
| A1 | $CF_3$ | $CH_2$ | $CH_3$ | O |
| A2 | $CF_3$ | $CH_2$ | $CH_2CH_3$ | O |
| A3 | $CF_3$ | $CH_2$ | $(CH_3)_2CH$ | O |
| A4 | $CF_3$ | $CH_2$ | $PhCH_2$ | O |
| A5 | $CF_3$ | $CH_2$ | $CH_3$ | S |
| A6 | $CF_3$ | $CH_2$ | $CH_3$ | SO |
| A7 | $CF_3$ | $CH_2$ | $CH_3$ | $SO_2$ |
| A8 | $CF_3$ | $CH_2$ | $CH_3OCH_2$ | O |
| A9 | $CF_3$ | $CH_2$ | $CH_3CH_2OCH_2$ | O |
| A10 | $CF_3$ | $CH_2$ | $CH_3OCH_2CH_2$ | O |
| A11 | $CF_3$ | $CH_2$ | $CH_3CH_2OCH_2CH_2$ | O |
| A12 | $CF_3$ | $CH_2$ | $CH_3OC(CH_3)_2CH_2$ | O |
| A13 | $CF_3$ | $CH_2$ | $CH_3OCH(CH_3)CH_2$ | O |
| A14 | $CF_3$ | $CH_2$ | $CH_3OCH_2CH(CH_3)$ | O |
| A15 | $CF_3$ | $CH_2$ | $CH_3OCH_2C(CH_3)_2$ | O |
| A16 | $CF_3$ | $CH_2$ | $CH_3OCH(CH_3)$ | O |
| A17 | $CF_3$ | $CH_2$ | $CH_3OC(CH_3)_2$ | O |
| A18 | $CF_3$ | $CH_2$ | $HC\equiv CH_2$ | O |
| A19 | $CF_3$ | $CH_2$ | $H_2C=CHCH_2$ | O |
| A20 | $CF_3$ | $CH_2$ | $CH_3C\equiv CCH_2$ | O |
| A21 | $CF_3$ | $CH_2$ | cyclopropyl-CH | O |
| A22 | $CF_3$ | $CH_2CH_2CH_2$ | cyclopropyl-CH | O |
| A23 | $CF_3$ | $CH_2$ | cyclobutyl-CH | O |
| A24 | $CF_3$ | $CH_2$ | oxetanyl-CH | O |
| A25 | $CF_3$ | $CH_2$ | cyclopentyl-CH | O |
| A26 | $CF_3$ | $CH_2$ | tetrahydrofuranyl-CH | O |
| A27 | $CF_3$ | $CH_2$ | cyclohexyl-CH | O |
| A28 | $CF_3$ | $CH_2$ | tetrahydropyranyl-CH | O |

-continued
| | | | | |
|---|---|---|---|---|
| A29 | CF₃ | CH₂ | 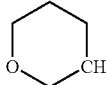 | O |
| A30 | CF₃ | CH₂ | 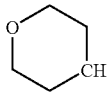 | O |
| A31 | CF₃ | CH₂ | 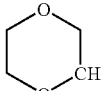 | O |
| A32 | CF₃ | CH₂ | 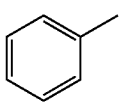 | O |
| A33 | CF₃ | CH₂ | 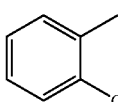 | O |
| A34 | CF₃ | CH₂ | 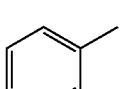 | O |
| A35 | CF₃ | CH₂ | 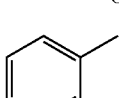 | O |
| A36 | CF₃ | CH₂ | 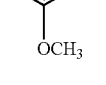 | O |
| A37 | CF₃ | CH₂ | 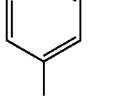 | O |
| A38 | CF₃ | CH₂ |  | O |
| A39 | CF₃ | CH₂ | 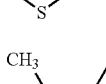 | O |
| A40 | CF₃ | CH₂ | 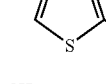 | O |

-continued
| | | | | |
|---|---|---|---|---|
| A41 | CF₃ | CH₂ | 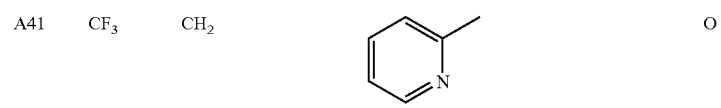 | O |
| A42 | CF₃ | CH₂ | 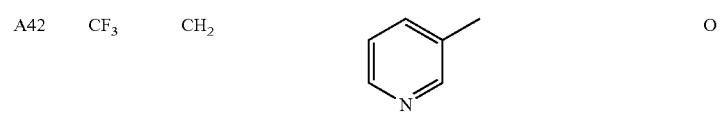 | O |
| A43 | CF₃ | CH₂ | 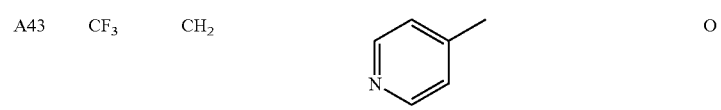 | O |
| A44 | CF₃ | CH₂ | 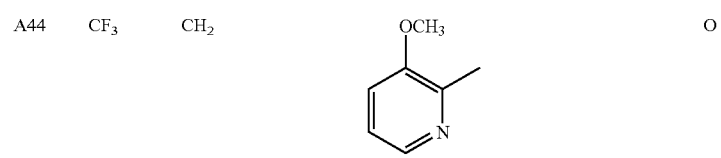 | O |
| A45 | CF₃ | CH₂ | 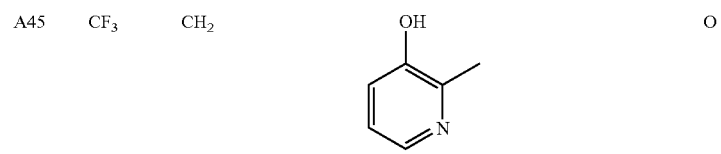 | O |
| A46 | CF₃ | CH₂ | 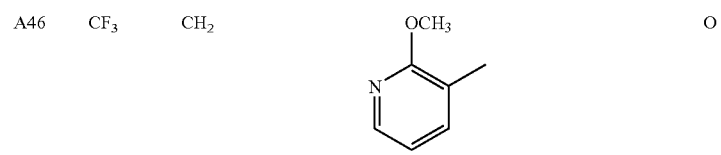 | O |
| A47 | CF₃ | CH₂ | 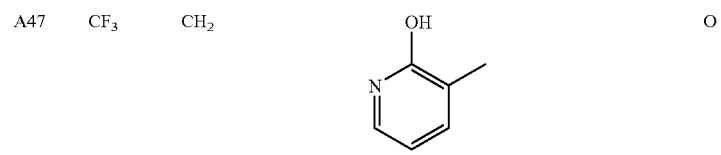 | O |
| A48 | CF₃ | CH₂ | 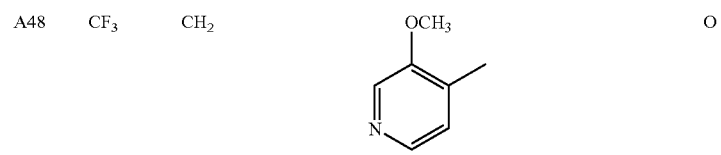 | O |
| A49 | CF₃ | CH₂ | 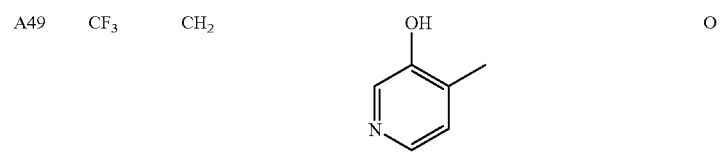 | O |
| A50 | CF₃ | CH₂ | 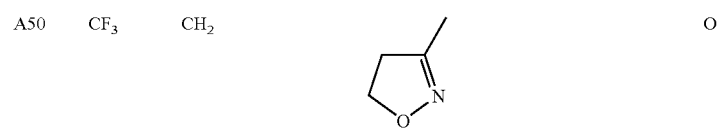 | O |
| A51 | CF₃ | CH₂ | 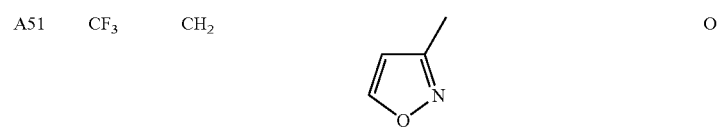 | O |

-continued
| | | | | | |
|---|---|---|---|---|---|
| A52 | CF$_3$ | CH$_2$ | 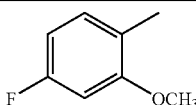 | O | |
| A53 | CF$_3$ | CH$_2$ | 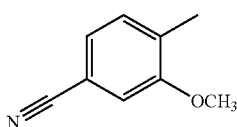 | O | |
| A54 | CF$_3$ | CH$_2$ | 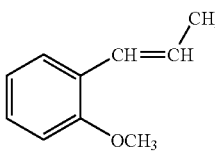 | O | |
| A55 | CF$_3$ | CH$_2$ | 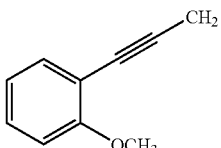 | O | |
| A56 | CF$_3$ | CH$_2$ | 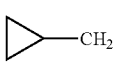 | O | |
| A57 | CF$_3$ | CH$_2$ | 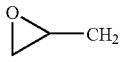 | O | |
| A58 | CF$_3$ | CH$_2$ | 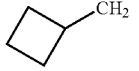 | O | |
| A59 | CF$_3$ | CH$_2$ |  | O | |
| A60 | CF$_3$ | CH$_2$ | 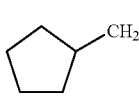 | O | |
| A61 | CF$_3$ | CH$_2$ | 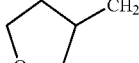 | O | |
| A62 | CF$_3$ | CH$_2$ | 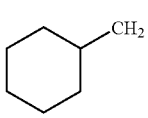 | O | |
| A63 | CF$_3$ | CH$_2$ | 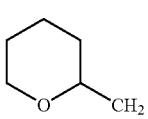 | O | |
| A64 | CF$_3$ | CH$_2$ | 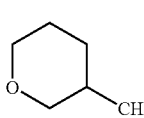 | O | |
| A65 | CF$_3$ | CH$_2$ | 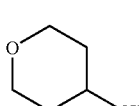 | O | |

-continued
| | | | | |
|---|---|---|---|---|
| A66 | CF₃ | CH₂ | 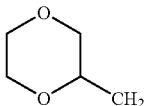 | O |
| A67 | CF₃ | CH₂ | 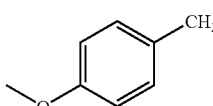 | O |
| A68 | CF₃ | CH₂ | 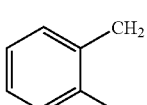 | O |
| A69 | CF₃ | CH₂ | 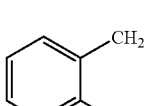 | O |
| A70 | CF₃ | CH₂ | 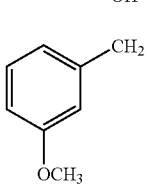 | O |
| A71 | CF₃ | CH₂ | 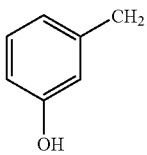 | O |
| A72 | CF₃ | CH₂ | 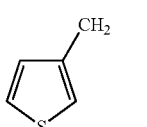 | O |
| A73 | CF₃ | CH₂ | 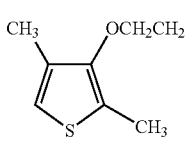 | O |
| A74 | CF₃ | CH₂ | 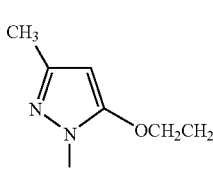 | O |
| A75 | CF₃ | CH₂ | 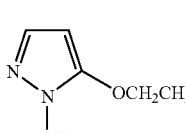 | O |
| A76 | CF₃ | CH₂ | 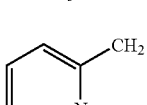 | O |

-continued
| | | | | | |
|---|---|---|---|---|---|
| A77 | CF$_3$ | CH$_2$ | 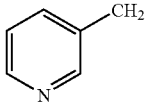 3-pyridyl-CH$_2$ | O | |
| A78 | CF$_3$ | CH$_2$ | 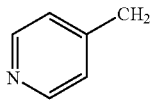 4-pyridyl-CH$_2$ | O | |
| A79 | CF$_3$ | CH$_2$ | 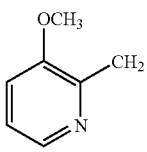 3-OCH$_3$-pyridin-2-yl-CH$_2$ | O | |
| A80 | CF$_3$ | CH$_2$ | 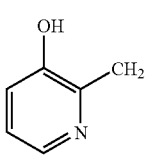 3-OH-pyridin-2-yl-CH$_2$ | O | |
| A81 | CF$_3$ | CH$_2$ | 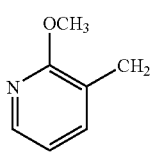 2-OCH$_3$-pyridin-3-yl-CH$_2$ | O | |
| A82 | CF$_3$ | CH$_2$ | 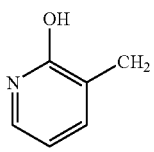 2-OH-pyridin-3-yl-CH$_2$ | O | |
| A83 | CF$_3$ | CH$_2$ | 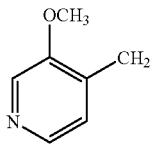 3-OCH$_3$-pyridin-4-yl-CH$_2$ | O | |
| A84 | CF$_3$ | CH$_2$ | 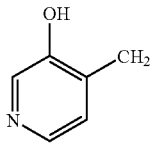 3-OH-pyridin-4-yl-CH$_2$ | O | |
| A85 | CF$_3$ | CH$_2$ | 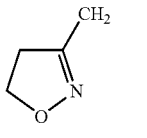 isoxazolin-3-yl-CH$_2$ | O | |
| A86 | CF$_3$ | CH$_2$ | 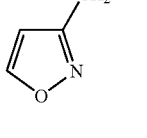 isoxazol-3-yl-CH$_2$ | O | |
| A87 | CF$_3$ | CH$_2$ | 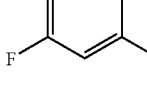 4-F-2-OCH$_3$-phenyl-CH$_2$ | O | |

-continued

| | | | | |
|---|---|---|---|---|
| A88 | $CF_3$ | $CH_2$ | 4-($OCH_2CH_2$)-3-($OCH_3$)-phenyl-CN | O |
| A89 | $CF_3$ | $CH_2$ | 2-($OCH_3$)-phenyl-$OCH_2CH_2$ | O |
| A90 | $CF_3$ | $CH_2$ | 2-($OCH_3$)-phenyl-$OCH_2$ | O |
| A91 | $CF_3$ | $CH_2CH_2$ | $CH_3$ | O |
| A92 | $CF_3$ | $CH_2CH_2$ | $CH_3CH_2$ | O |
| A93 | $CF_3$ | $CH_2CH_2$ | $(CH_3)_2CH$ | O |
| A94 | $CF_3$ | $CH_2CH_2$ | $PhCH_2$ | O |
| A95 | $CF_3$ | $CH_2CH_2$ | $CH_3$ | S |
| A96 | $CF_3$ | $CH_2CH_2$ | $CH_3$ | SO |
| A97 | $CF_3$ | $CH_2CH_2$ | $CH_3$ | $SO_2$ |
| A98 | $CF_3$ | $CH_2CH_2$ | $(CH_3)_2CHCH_2$ | O |
| A99 | $CF_3$ | $CH_2CH_2$ | $CH_3OCH_2$ | O |
| A100 | $CF_3$ | $CH_2CH_2$ | $CH_3CH_2OCH_2$ | O |
| A101 | $CF_3$ | $CH_2CH_2$ | $CH_3OCH_2CH_2$ | O |
| A102 | $CF_3$ | $CH_2CH_2$ | $CH_3CH_2OCH_2CH_2$ | O |
| A103 | $CF_3$ | $CH_2CH_2$ | $CH_3OC(CH_3)_2CH_2$ | O |
| A104 | $CF_3$ | $CH_2CH_2$ | $CH_3OCH(CH_3)CH_2$ | O |
| A105 | $CF_3$ | $CH_2CH_2$ | $CH_3OCH_2CH(CH_3)$ | O |
| A106 | $CF_3$ | $CH_2CH_2$ | $CH_3OCH_2C(CH_3)_2$ | O |
| A107 | $CF_3$ | $CH_2CH_2$ | $CH_3OCH(CH_3)$ | O |
| A108 | $CF_3$ | $CH_2CH_2$ | $CH_3OC(CH_3)_2$ | O |
| A109 | $CF_3$ | $CH_2CH_2$ | $HC{\equiv}CH_2$ | O |
| A110 | $CF_3$ | $CH_2CH_2$ | $H_2C{=}CHCH_2$ | O |
| A111 | $CF_3$ | $CH_2CH_2$ | $CH_3C{\equiv}CCH_2$ | O |
| A112 | $CF_3$ | $CH_2CH_2$ | cyclopropyl-CH | O |
| A113 | $CF_3$ | $CH_2CH_2CH_2$ | cyclopropyl-CH | O |
| A114 | $CF_3$ | $CH_2CH_2$ | cyclobutyl-CH | O |
| A115 | $CF_3$ | $CH_2CH_2$ | oxetanyl-CH | O |
| A116 | $CF_3$ | $CH_2CH_2$ | cyclopentyl-CH | O |
| A117 | $CF_3$ | $CH_2CH_2$ | tetrahydrofuranyl-CH | O |
| A118 | $CF_3$ | $CH_2CH_2$ | cyclohexyl-CH | O |
| A119 | $CF_3$ | $CH_2CH_2$ | tetrahydropyranyl-CH | O |

| | | | -continued | |
|---|---|---|---|---|
| A120 | CF₃ | CH₂CH₂ | tetrahydropyran-4-yl (O in ring, CH at 4-position) | O |
| A121 | CF₃ | CH₂CH₂ | tetrahydropyran-4-yl | O |
| A122 | CF₃ | CH₂CH₂ | 1,3-dioxan-2-yl | O |
| A123 | CF₃ | CH₂CH₂ | phenyl | O |
| A124 | CF₃ | CH₂CH₂ | 2-methoxyphenyl | O |
| A125 | CF₃ | CH₂CH₂ | 2-hydroxyphenyl | O |
| A126 | CF₃ | CH₂CH₂ | 3-methoxyphenyl | O |
| A127 | CF₃ | CH₂CH₂ | 3-hydroxyphenyl | O |
| A128 | CF₃ | CH₂CH₂ | thiophen-3-yl | O |
| A129 | CF₃ | CH₂CH₂ | 2,3-dimethylthiophen-4-yl | O |
| A130 | CF₃ | CH₂CH₂ | 1,3-dimethyl-1H-pyrazol-5-yl | O |
| A131 | CF₃ | CH₂CH₂ | 1-methyl-1H-pyrazol-5-yl | O |

-continued
| | | | | | |
|---|---|---|---|---|---|
| A132 | CF$_3$ | CH$_2$CH$_2$ | 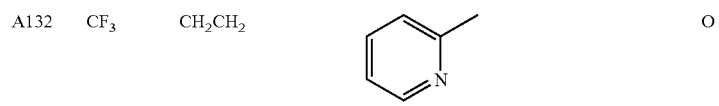 | | O |
| A133 | CF$_3$ | CH$_2$CH$_2$ | 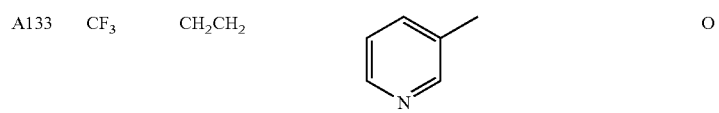 | | O |
| A134 | CF$_3$ | CH$_2$CH$_2$ | 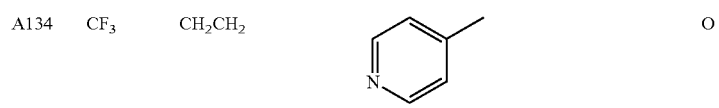 | | O |
| A135 | CF$_3$ | CH$_2$CH$_2$ | 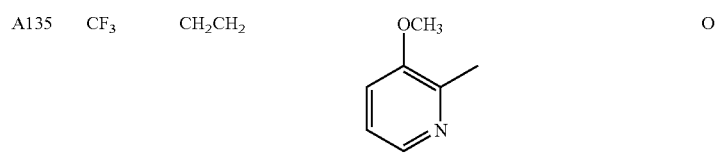 | | O |
| A136 | CF$_3$ | CH$_2$CH$_2$ | 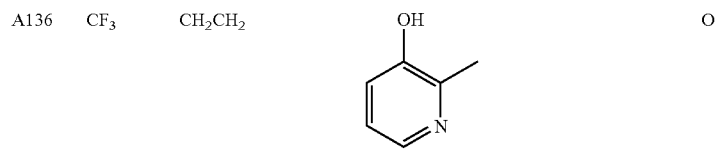 | | O |
| A137 | CF$_3$ | CH$_2$CH$_2$ | 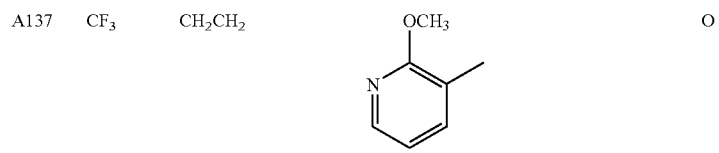 | | O |
| A138 | CF$_3$ | CH$_2$CH$_2$ | 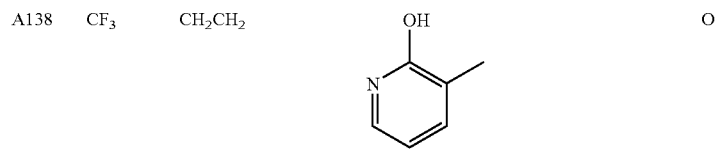 | | O |
| A139 | CF$_3$ | CH$_2$CH$_2$ | 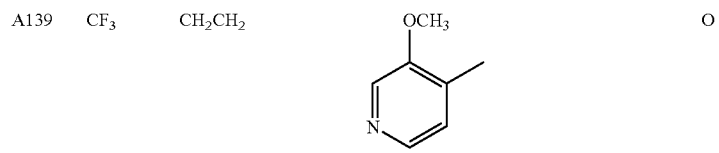 | | O |
| A140 | CF$_3$ | CH$_2$CH$_2$ | 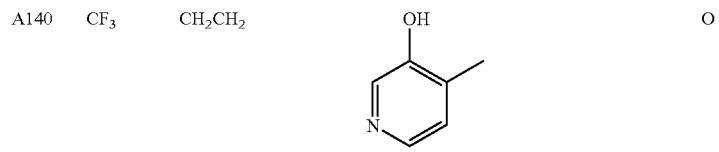 | | O |
| A141 | CF$_3$ | CH$_2$CH$_2$ | 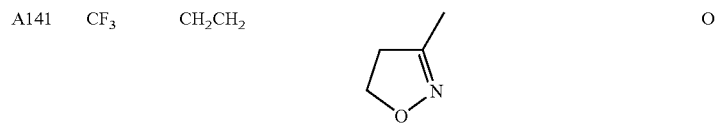 | | O |
| A142 | CF$_3$ | CH$_2$CH$_2$ | 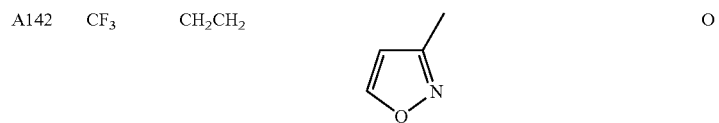 | | O |

-continued
| | | | | | |
|---|---|---|---|---|---|
| A143 | CF$_3$ | CH$_2$CH$_2$ | 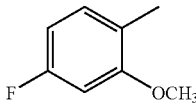 | O | |
| A144 | CF$_3$ | CH$_2$CH$_2$ | 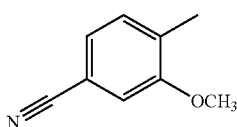 | O | |
| A145 | CF$_3$ | CH$_2$CH$_2$ | 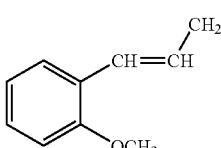 | O | |
| A146 | CF$_3$ | CH$_2$CH$_2$ | 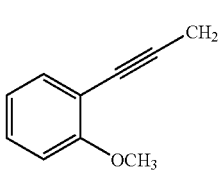 | O | |
| A147 | CF$_3$ | CH$_2$CH$_2$ | 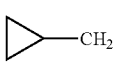 | O | |
| A148 | CF$_3$ | CH$_2$CH$_2$ | 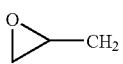 | O | |
| A149 | CF$_3$ | CH$_2$CH$_2$ | 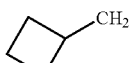 | O | |
| A150 | CF$_3$ | CH$_2$CH$_2$ | 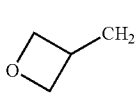 | O | |
| A151 | CF$_3$ | CH$_2$CH$_2$ | 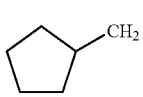 | O | |
| A152 | CF$_3$ | CH$_2$CH$_2$ | 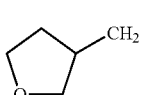 | O | |
| A153 | CF$_3$ | CH$_2$CH$_2$ | 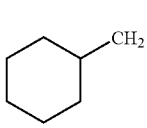 | O | |
| A154 | CF$_3$ | CH$_2$CH$_2$ | 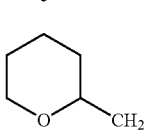 | O | |
| A155 | CF$_3$ | CH$_2$CH$_2$ | 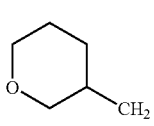 | O | |
| A156 | CF$_3$ | CH$_2$CH$_2$ | 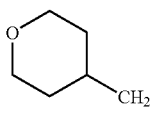 | O | |

-continued
| | | | | |
|---|---|---|---|---|
| A157 | CF₃ | CH₂CH₂ | 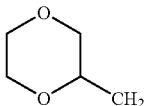 | O |
| A158 | CF₃ | CH₂CH₂ | 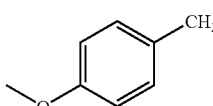 | O |
| A159 | CF₃ | CH₂CH₂ | 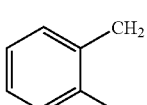 | O |
| A160 | CF₃ | CH₂CH₂ | 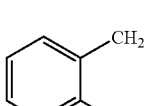 | O |
| A161 | CF₃ | CH₂CH₂ | 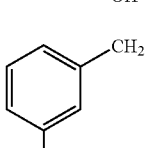 | O |
| A162 | CF₃ | CH₂CH₂ | 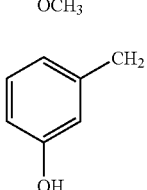 | O |
| A163 | CF₃ | CH₂CH₂ | 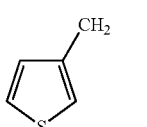 | O |
| A164 | CF₃ | CH₂CH₂ | 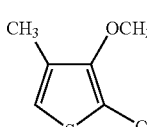 | O |
| A165 | CF₃ | CH₂CH₂ | 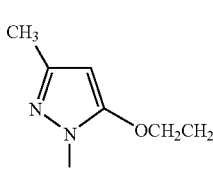 | O |
| A166 | CF₃ | CH₂CH₂ | 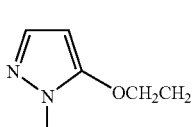 | O |
| A167 | CF₃ | CH₂CH₂ | 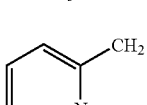 | O |

-continued
| | | | | | |
|---|---|---|---|---|---|
| A168 | CF$_3$ | CH$_2$CH$_2$ | 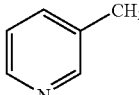 | O | |
| A169 | CF$_3$ | CH$_2$CH$_2$ | 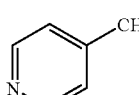 | O | |
| A170 | CF$_3$ | CH$_2$CH$_2$ | 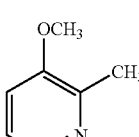 | O | |
| A171 | CF$_3$ | CH$_2$CH$_2$ | 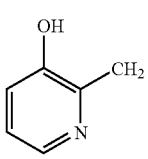 | O | |
| A172 | CF$_3$ | CH$_2$CH$_2$ | 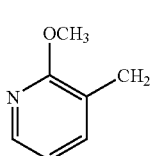 | O | |
| A173 | CF$_3$ | CH$_2$CH$_2$ | 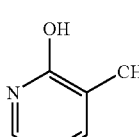 | O | |
| A174 | CF$_3$ | CH$_2$CH$_2$ | 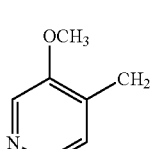 | O | |
| A175 | CF$_3$ | CH$_2$CH$_2$ | 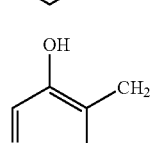 | O | |
| A176 | CF$_3$ | CH$_2$CH$_2$ | 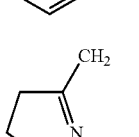 | O | |
| A177 | CF$_3$ | CH$_2$CH$_2$ | 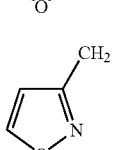 | O | |
| A178 | CF$_3$ | CH$_2$CH$_2$ | 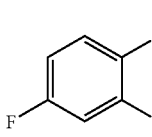 | O | |

-continued

| | | | | | |
|---|---|---|---|---|---|
| A179 | CF$_3$ | CH$_2$CH$_2$ | 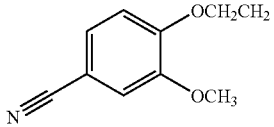 | O |
| A180 | CF$_3$ | CH$_2$CH$_2$ | 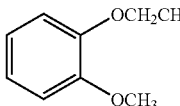 | O |
| A181 | CF$_3$ | CH$_2$CH$_2$ | 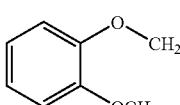 | O |
| A182 | CF$_3$ | CH(OCH$_3$)CH$_2$ | CH$_3$ | O |
| A183 | CF$_3$ | CH(OCH$_3$)CH$_2$ | CH$_3$CH$_2$ | O |
| A184 | CF$_3$ | CH(OCH$_3$)CH$_2$ | (CH$_3$)$_2$CH | O |
| A185 | CF$_3$ | CH(OCH$_3$)CH$_2$ | PhCH$_2$ | O |
| A186 | CF$_3$ | CH(OCH$_3$)CH$_2$ | CH$_3$ | S |
| A187 | CF$_3$ | CH(OCH$_3$)CH$_2$ | CH$_3$ | SO |
| A188 | CF$_3$ | CH(OCH$_3$)CH$_2$ | CH$_3$ | SO$_2$ |
| A189 | CF$_3$ | CH(OCH$_3$)CH$_2$ | CH$_3$CH$_2$CH$_2$ | O |
| A190 | CF$_3$ | CH(OCH$_3$)CH$_2$ | CH$_3$OCH$_2$ | O |
| A191 | CF$_3$ | CH(OCH$_3$)CH$_2$ | CH$_3$CH$_2$OCH$_2$ | O |
| A192 | CF$_3$ | CH(OCH$_3$)CH$_2$ | CH$_3$OCH$_2$CH$_2$ | O |
| A193 | CF$_3$ | CH(OCH$_3$)CH$_2$ | CH$_3$CH$_2$OCH$_2$CH$_2$ | O |
| A194 | CF$_3$ | CH(OCH$_3$)CH$_2$ | CH$_3$OC(CH$_3$)$_2$CH$_2$ | O |
| A195 | CF$_3$ | CH(OCH$_3$)CH$_2$ | CH$_3$OCH(CH$_3$)CH$_2$ | O |
| A196 | CF$_3$ | CH(OCH$_3$)CH$_2$ | CH$_3$OCH$_2$CH(CH$_3$) | O |
| A197 | CF$_3$ | CH(OCH$_3$)CH$_2$ | CH$_3$OCH$_2$C(CH$_3$)$_2$ | O |
| A198 | CF$_3$ | CH(OCH$_3$)CH$_2$ | CH$_3$OCH(CH$_3$) | O |
| A199 | CF$_3$ | CH(OCH$_3$)CH$_2$ | CH$_3$OC(CH$_3$)$_2$ | O |
| A200 | CF$_3$ | CH(OCH$_3$)CH$_2$ | HC≡CH$_2$ | O |
| A201 | CF$_3$ | CH(OCH$_3$)CH$_2$ | H$_2$C═CHCH$_2$ | O |
| A202 | CF$_3$ | CH(OCH$_3$)CH$_2$ | CH$_3$C≡CCH$_2$ | O |
| A203 | CF$_3$ | CH(OCH$_3$)CH$_2$ |  | O |
| A204 | CF$_3$ | CH$_2$CH$_2$CH$_2$ |  | O |
| A205 | CF$_3$ | CH(OCH$_3$)CH$_2$ |  | O |
| A206 | CF$_3$ | CH(OCH$_3$)CH$_2$ |  | O |
| A207 | CF$_3$ | CH(OCH$_3$)CH$_2$ |  | O |
| A208 | CF$_3$ | CH(OCH$_3$)CH$_2$ |  | O |
| A209 | CF$_3$ | CH(OCH$_3$)CH$_2$ |  | O |
| A210 | CF$_3$ | CH(OCH$_3$)CH$_2$ |  | O |

-continued
| | | | | |
|---|---|---|---|---|
| A211 | CF$_3$ | CH(OCH$_3$)CH$_2$ | 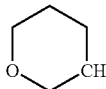 | O |
| A212 | CF$_3$ | CH(OCH$_3$)CH$_2$ | 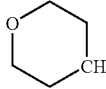 | O |
| A213 | CF$_3$ | CH(OCH$_3$)CH$_2$ | 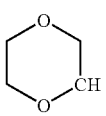 | O |
| A214 | CF$_3$ | CH(OCH$_3$)CH$_2$ | 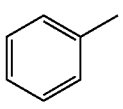 | O |
| A215 | CF$_3$ | CH(OCH$_3$)CH$_2$ | 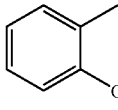 | O |
| A216 | CF$_3$ | CH(OCH$_3$)CH$_2$ | 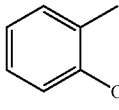 | O |
| A217 | CF$_3$ | CH(OCH$_3$)CH$_2$ | 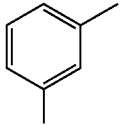 | O |
| A218 | CF$_3$ | CH(OCH$_3$)CH$_2$ | 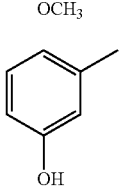 | O |
| A219 | CF$_3$ | CH(OCH$_3$)CH$_2$ | 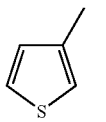 | O |
| A220 | CF$_3$ | CH(OCH$_3$)CH$_2$ | 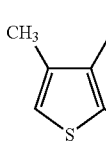 | O |
| A221 | CF$_3$ | CH(OCH$_3$)CH$_2$ | 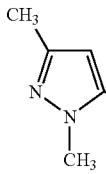 | O |
| A222 | CF$_3$ | CH(OCH$_3$)CH$_2$ | 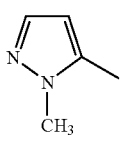 | O |

-continued
| | | | | | |
|---|---|---|---|---|---|
| A223 | CF₃ | CH(OCH₃)CH₂ | 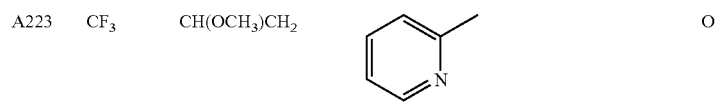 | | O |
| A224 | CF₃ | CH(OCH₃)CH₂ | 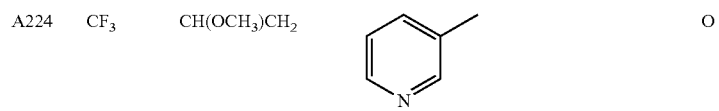 | | O |
| A225 | CF₃ | CH(OCH₃)CH₂ | 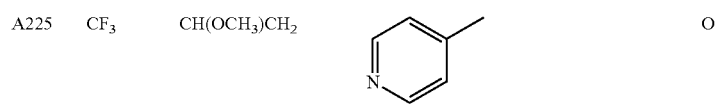 | | O |
| A226 | CF₃ | CH(OCH₃)CH₂ | 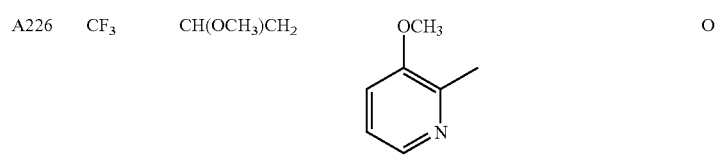 | | O |
| A227 | CF₃ | CH(OCH₃)CH₂ | 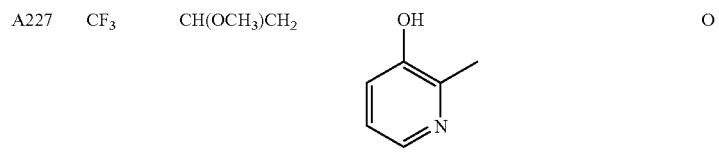 | | O |
| A228 | CF₃ | CH(OCH₃)CH₂ | 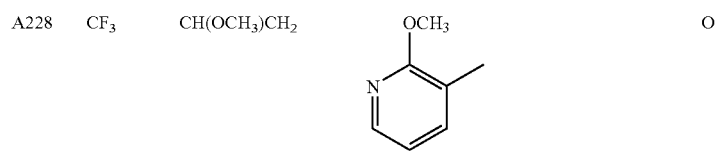 | | O |
| A229 | CF₃ | CH(OCH₃)CH₂ | 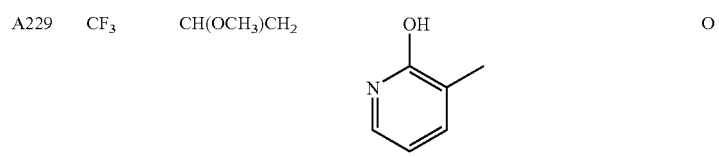 | | O |
| A230 | CF₃ | CH(OCH₃)CH₂ | 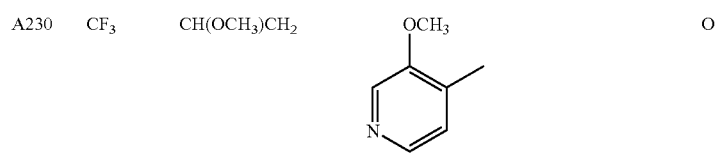 | | O |
| A231 | CF₃ | CH(OCH₃)CH₂ | 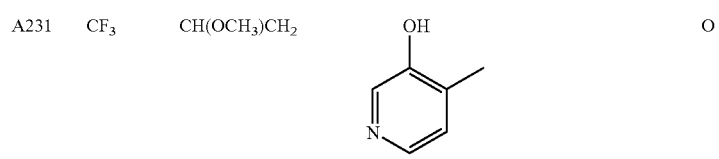 | | O |
| A232 | CF₃ | CH(OCH₃)CH₂ | 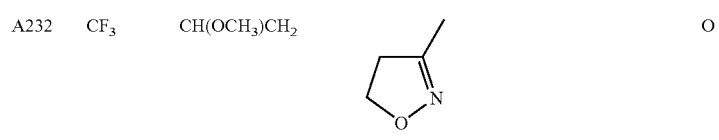 | | O |
| A233 | CF₃ | CH(OCH₃)CH₂ | 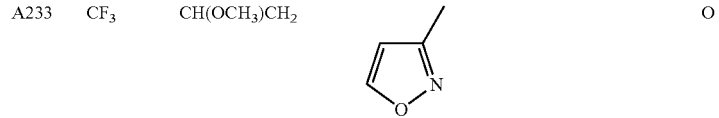 | | O |

-continued
| | | | | |
|---|---|---|---|---|
| A234 | CF$_3$ | CH(OCH$_3$)CH$_2$ | 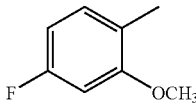 | O |
| A235 | CF$_3$ | CH(OCH$_3$)CH$_2$ | 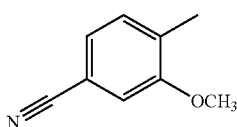 | O |
| A236 | CF$_3$ | CH(OCH$_3$)CH$_2$ | 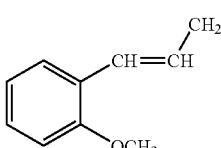 | O |
| A237 | CF$_3$ | CH(OCH$_3$)CH$_2$ | 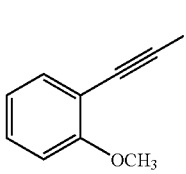 | O |
| A238 | CF$_3$ | CH(OCH$_3$)CH$_2$ | 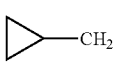 | O |
| A239 | CF$_3$ | CH(OCH$_3$)CH$_2$ | 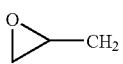 | O |
| A240 | CF$_3$ | CH(OCH$_3$)CH$_2$ | 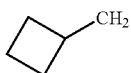 | O |
| A241 | CF$_3$ | CH(OCH$_3$)CH$_2$ | 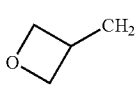 | O |
| A242 | CF$_3$ | CH(OCH$_3$)CH$_2$ | 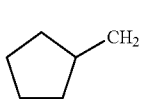 | O |
| A243 | CF$_3$ | CH(OCH$_3$)CH$_2$ | 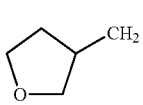 | O |
| A244 | CF$_3$ | CH(OCH$_3$)CH$_2$ | 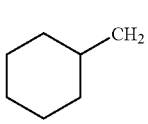 | O |
| A245 | CF$_3$ | CH(OCH$_3$)CH$_2$ | 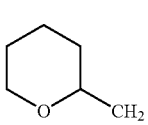 | O |
| A246 | CF$_3$ | CH(OCH$_3$)CH$_2$ | 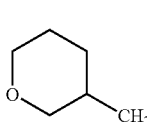 | O |
| A247 | CF$_3$ | CH(OCH$_3$)CH$_2$ | 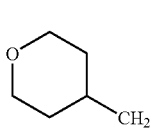 | O |

-continued
| | | | | |
|---|---|---|---|---|
| A248 | CF₃ | CH(OCH₃)CH₂ | 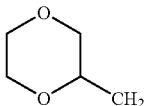 | O |
| A249 | CF₃ | CH(OCH₃)CH₂ | 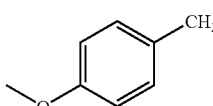 | O |
| A250 | CF₃ | CH(OCH₃)CH₂ | 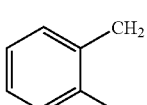 | O |
| A251 | CF₃ | CH(OCH₃)CH₂ | 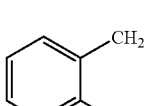 | O |
| A252 | CF₃ | CH(OCH₃)CH₂ | 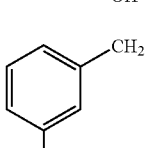 | O |
| A253 | CF₃ | CH(OCH₃)CH₂ | 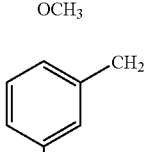 | O |
| A254 | CF₃ | CH(OCH₃)CH₂ | 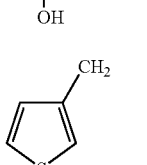 | O |
| A255 | CF₃ | CH(OCH₃)CH₂ | 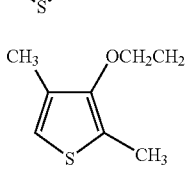 | O |
| A256 | CF₃ | CH(OCH₃)CH₂ | 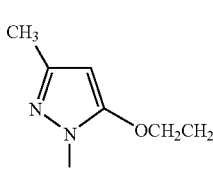 | O |
| A257 | CF₃ | CH(OCH₃)CH₂ | 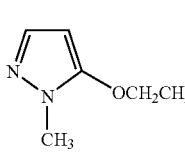 | O |
| A258 | CF₃ | CH(OCH₃)CH₂ | 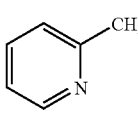 | O |

-continued
| | | | | | |
|---|---|---|---|---|---|
| A259 | CF₃ | CH(OCH₃)CH₂ | 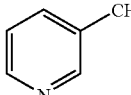 | | O |
| A260 | CF₃ | CH(OCH₃)CH₂ | 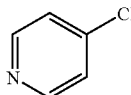 | | O |
| A261 | CF₃ | CH(OCH₃)CH₂ | 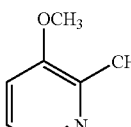 | | O |
| A262 | CF₃ | CH(OCH₃)CH₂ | 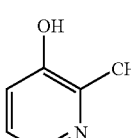 | | O |
| A263 | CF₃ | CH(OCH₃)CH₂ | 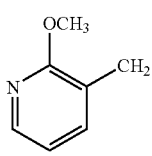 | | O |
| A264 | CF₃ | CH(OCH₃)CH₂ | 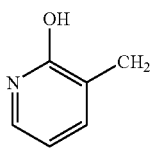 | | O |
| A265 | CF₃ | CH(OCH₃)CH₂ | 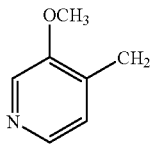 | | O |
| A266 | CF₃ | CH(OCH₃)CH₂ | 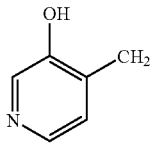 | | O |
| A267 | CF₃ | CH(OCH₃)CH₂ | 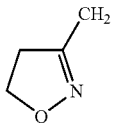 | | O |
| A268 | CF₃ | CH(OCH₃)CH₂ | 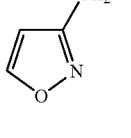 | | O |
| A269 | CF₃ | CH(OCH₃)CH₂ | 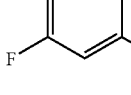 | | O |

-continued

| | | | | |
|---|---|---|---|---|
| A270 | CF₃ | CH(OCH₃)CH₂ | 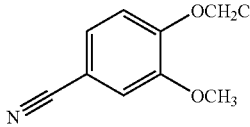 | O |
| A271 | CF₃ | CH(OCH₃)CH₂ | 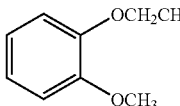 | O |
| A272 | CF₃ | CH(OCH₃)CH₂ | 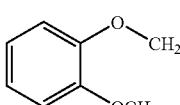 | O |
| A273 | CF₃ | CH₂CH(OCH₃)CH₂ | CH₃ | O |
| A274 | CF₃ | CH₂CH(OCH₃)CH₂ | CH₃CH₂ | O |
| A275 | CF₃ | CH₂CH(OCH₃)CH₂ | (CH₃)₂CH | O |
| A276 | CF₃ | CH₂CH(OCH₃)CH₂ | PhCH₂ | O |
| A277 | CF₃ | CH₂CH(OCH₃)CH₂ | CH₃ | S |
| A278 | CF₃ | CH₂CH(OCH₃)CH₂ | CH₃ | SO |
| A279 | CF₃ | CH₂CH(OCH₃)CH₂ | CH₃ | SO₂ |
| A280 | CF₃ | CH₂CH(OCH₃)CH₂ | CH₃CH₂CH₂ | O |
| A281 | CF₃ | CH₂CH(OCH₃)CH₂ | CH₃OCH₂ | O |
| A282 | CF₃ | CH₂CH(OCH₃)CH₂ | CH₃CH₂OCH₂ | O |
| A283 | CF₃ | CH₂CH(OCH₃)CH₂ | CH₃OCH₂CH₂ | O |
| A284 | CF₃ | CH₂CH(OCH₃)CH₂ | CH₃CH₂OCH₂CH₂ | O |
| A285 | CF₃ | CH₂CH(OCH₃)CH₂ | CH₃OC(CH₃)₂CH₂ | O |
| A286 | CF₃ | CH₂CH(OCH₃)CH₂ | CH₃OCH(CH₃)CH₂ | O |
| A287 | CF₃ | CH₂CH(OCH₃)CH₂ | CH₃OCH₂CH(CH₃) | O |
| A288 | CF₃ | CH₂CH(OCH₃)CH₂ | CH₃OCH₂C(CH₃)₂ | O |
| A289 | CF₃ | CH₂CH(OCH₃)CH₂ | CH₃OCH(CH₃) | O |
| A290 | CF₃ | CH₂CH(OCH₃)CH₂ | CH₃OC(CH₃)₂ | O |
| A291 | CF₃ | CH₂CH(OCH₃)CH₂ | HC≡CH₂ | O |
| A292 | CF₃ | CH₂CH(OCH₃)CH₂ | H₂C=CHCH₂ | O |
| A293 | CF₃ | CH₂CH(OCH₃)CH₂ | CH₃C≡CCH₂ | O |
| A294 | CF₃ | CH₂CH(OCH₃)CH₂ |  | O |
| A295 | CF₃ | CH₂CH₂CH₂ |  | O |
| A296 | CF₃ | CH₂CH(OCH₃)CH₂ |  | O |
| A297 | CF₃ | CH₂CH(OCH₃)CH₂ |  | O |
| A298 | CF₃ | CH₂CH(OCH₃)CH₂ |  | O |
| A299 | CF₃ | CH₂CH(OCH₃)CH₂ |  | O |
| A300 | CF₃ | CH₂CH(OCH₃)CH₂ |  | O |
| A301 | CF₃ | CH₂CH(OCH₃)CH₂ |  | O |

-continued

| A302 | CF$_3$ | CH$_2$CH(OCH$_3$)CH$_2$ | tetrahydropyran-4-yl (O at 1, CH at 4) | O |
| A303 | CF$_3$ | CH$_2$CH(OCH$_3$)CH$_2$ | tetrahydropyran-4-yl | O |
| A304 | CF$_3$ | CH$_2$CH(OCH$_3$)CH$_2$ | 1,3-dioxan-2-yl | O |
| A305 | CF$_3$ | CH$_2$CH(OCH$_3$)CH$_2$ | phenyl | O |
| A306 | CF$_3$ | CH$_2$CH(OCH$_3$)CH$_2$ | 2-methoxyphenyl | O |
| A307 | CF$_3$ | CH$_2$CH(OCH$_3$)CH$_2$ | 2-hydroxyphenyl | O |
| A308 | CF$_3$ | CH$_2$CH(OCH$_3$)CH$_2$ | 3-methoxyphenyl | O |
| A309 | CF$_3$ | CH$_2$CH(OCH$_3$)CH$_2$ | 3-hydroxyphenyl | O |
| A310 | CF$_3$ | CH$_2$CH(OCH$_3$)CH$_2$ | 3-methylthiophen-yl | O |
| A311 | CF$_3$ | CH$_2$CH(OCH$_3$)CH$_2$ | 2,3-dimethylthiophen-4-yl | O |
| A312 | CF$_3$ | CH$_2$CH(OCH$_3$)CH$_2$ | 1,3-dimethylpyrazol-5-yl | O |
| A313 | CF$_3$ | CH$_2$CH(OCH$_3$)CH$_2$ | 1,5-dimethylpyrazol-3-yl | O |

-continued
| | | | | | |
|---|---|---|---|---|---|
| A314 | CF₃ | CH₂CH(OCH₃)CH₂ | 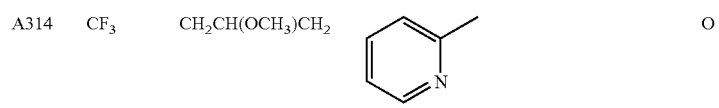 | | O |
| A315 | CF₃ | CH₂CH(OCH₃)CH₂ | 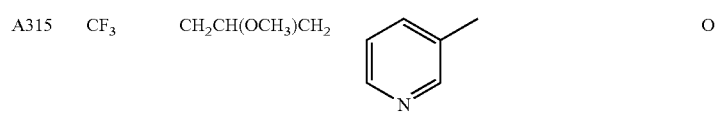 | | O |
| A316 | CF₃ | CH₂CH(OCH₃)CH₂ | 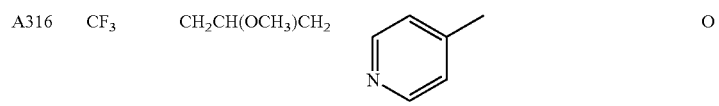 | | O |
| A317 | CF₃ | CH₂CH(OCH₃)CH₂ | 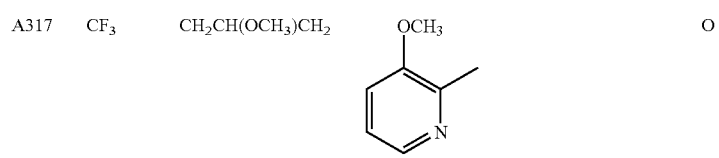 | | O |
| A318 | CF₃ | CH₂CH(OCH₃)CH₂ | 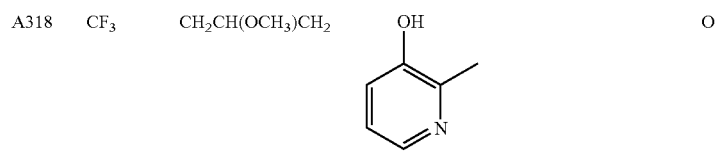 | | O |
| A319 | CF₃ | CH₂CH(OCH₃)CH₂ | 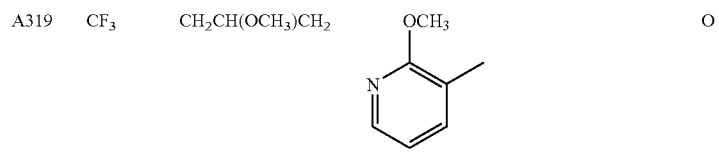 | | O |
| A320 | CF₃ | CH₂CH(OCH₃)CH₂ | 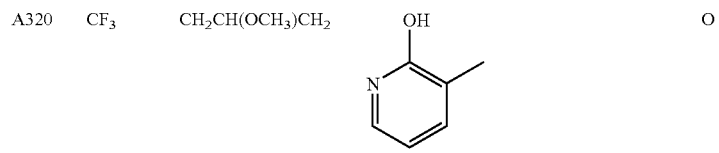 | | O |
| A321 | CF₃ | CH₂CH(OCH₃)CH₂ | 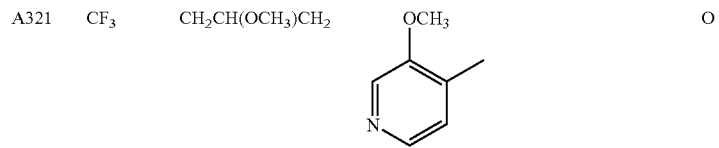 | | O |
| A322 | CF₃ | CH₂CH(OCH₃)CH₂ | 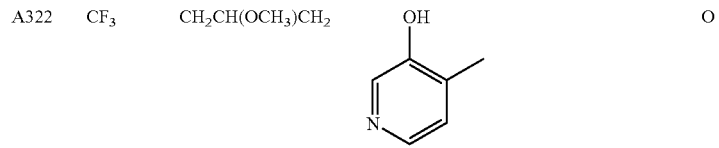 | | O |
| A323 | CF₃ | CH₂CH(OCH₃)CH₂ | 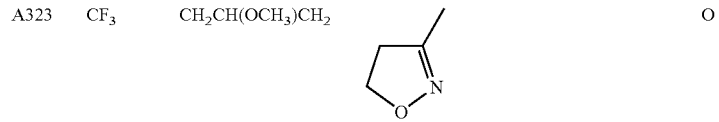 | | O |
| A324 | CF₃ | CH₂CH(OCH₃)CH₂ | 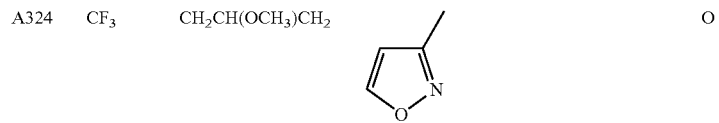 | | O |

| | | | | | |
|---|---|---|---|---|---|
| A325 | CF₃ | CH₂CH(OCH₃)CH₂ | 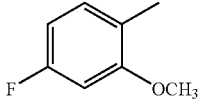 | O |
| A326 | CF₃ | CH₂CH(OCH₃)CH₂ | 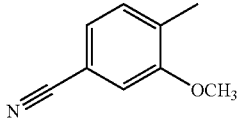 | O |
| A327 | CF₃ | CH₂CH(OCH₃)CH₂ | 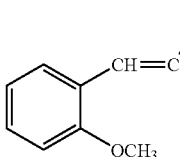 | O |
| A328 | CF₃ | CH₂CH(OCH₃)CH₂ | 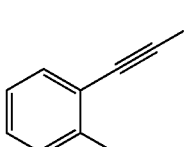 | O |
| A329 | CF₃ | CH₂CH(OCH₃)CH₂ | 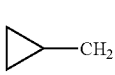 | O |
| A330 | CF₃ | CH₂CH(OCH₃)CH₂ | 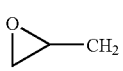 | O |
| A331 | CF₃ | CH₂CH(OCH₃)CH₂ |  | O |
| A332 | CF₃ | CH₂CH(OCH₃)CH₂ | 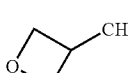 | O |
| A333 | CF₃ | CH₂CH(OCH₃)CH₂ | 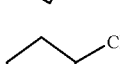 | O |
| A334 | CF₃ | CH₂CH(OCH₃)CH₂ | 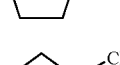 | O |
| A335 | CF₃ | CH₂CH(OCH₃)CH₂ | 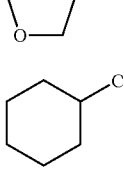 | O |
| A336 | CF₃ | CH₂CH(OCH₃)CH₂ | 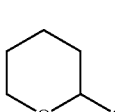 | O |
| A337 | CF₃ | CH₂CH(OCH₃)CH₂ | 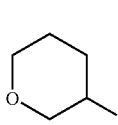 | O |
| A338 | CF₃ | CH₂CH(OCH₃)CH₂ | 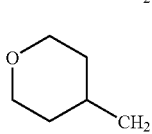 | O |

-continued
| | | | | |
|---|---|---|---|---|
| A339 | CF₃ | CH₂CH(OCH₃)CH₂ | 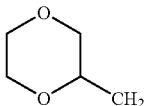 | O |
| A340 | CF₃ | CH₂CH(OCH₃)CH₂ | 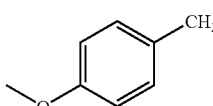 | O |
| A341 | CF₃ | CH₂CH(OCH₃)CH₂ | 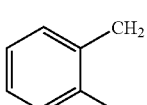 | O |
| A342 | CF₃ | CH₂CH(OCH₃)CH₂ | 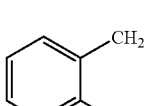 | O |
| A343 | CF₃ | CH₂CH(OCH₃)CH₂ | 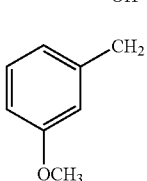 | O |
| A344 | CF₃ | CH₂CH(OCH₃)CH₂ | 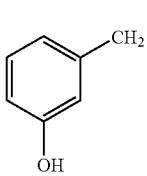 | O |
| A345 | CF₃ | CH₂CH(OCH₃)CH₂ | 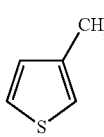 | O |
| A346 | CF₃ | CH₂CH(OCH₃)CH₂ | 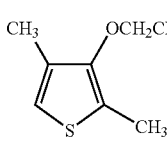 | O |
| A347 | CF₃ | CH₂CH(OCH₃)CH₂ | 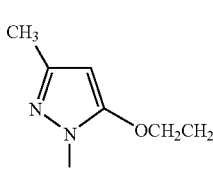 | O |
| A348 | CF₃ | CH₂CH(OCH₃)CH₂ | 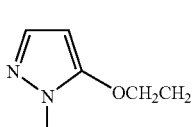 | O |
| A349 | CF₃ | CH₂CH(OCH₃)CH₂ | 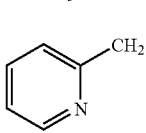 | O |

-continued
| | | | | | |
|---|---|---|---|---|---|
| A350 | CF₃ | CH₂CH(OCH₃)CH₂ | 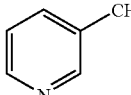 | | O |
| A351 | CF₃ | CH₂CH(OCH₃)CH₂ | 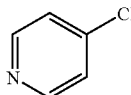 | | O |
| A352 | CF₃ | CH₂CH(OCH₃)CH₂ | 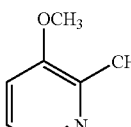 | | O |
| A353 | CF₃ | CH₂CH(OCH₃)CH₂ | 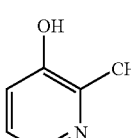 | | O |
| A354 | CF₃ | CH₂CH(OCH₃)CH₂ | 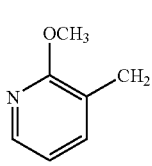 | | O |
| A355 | CF₃ | CH₂CH(OCH₃)CH₂ | 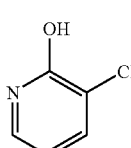 | | O |
| A356 | CF₃ | CH₂CH(OCH₃)CH₂ | 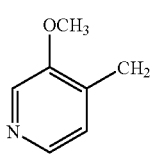 | | O |
| A357 | CF₃ | CH₂CH(OCH₃)CH₂ | 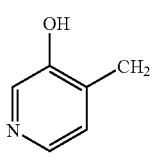 | | O |
| A358 | CF₃ | CH₂CH(OCH₃)CH₂ | 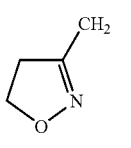 | | O |
| A359 | CF₃ | CH₂CH(OCH₃)CH₂ | 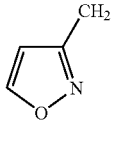 | | O |
| A360 | CF₃ | CH₂CH(OCH₃)CH₂ | 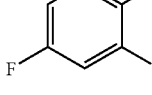 | | O |

-continued

| | | | | |
|---|---|---|---|---|
| A361 | CF₃ | CH₂CH(OCH₃)CH₂ | 4-OCH₂CH₃-3-OCH₃-phenyl with CN | O |
| A362 | CF₃ | CH₂CH(OCH₃)CH₂ | 2-OCH₂CH₃-3-OCH₃-phenyl | O |
| A363 | CF₃ | CH₂CH(OCH₃)CH₂ | 2-OCH₂-3-OCH₃-phenyl | O |
| A364 | CF₃ | CH=CHCH₂ | CH₃ | O |
| A365 | CF₃ | CH=CHCH₂ | CH₃CH₂ | O |
| A366 | CF₃ | CH=CHCH₂ | (CH₃)₂CH | O |
| A367 | CF₃ | CH=CHCH₂ | PhCH₂ | O |
| A368 | CF₃ | CH=CHCH₂ | CH₃ | S |
| A369 | CF₃ | CH=CHCH₂ | CH₃ | SO |
| A370 | CF₃ | CH=CHCH₂ | CH₃ | SO₂ |
| A371 | CF₃ | CH=CHCH₂ | CH₃CH₂CH₂ | O |
| A372 | CF₃ | CH=CHCH₂ | CH₃OCH₂ | O |
| A373 | CF₃ | CH=CHCH₂ | CH₃CH₂OCH₂ | O |
| A374 | CF₃ | CH=CHCH₂ | CH₃OCH₂CH₂ | O |
| A375 | CF₃ | CH=CHCH₂ | CH₃CH₂OCH₂CH₂ | O |
| A376 | CF₃ | CH=CHCH₂ | CH₃OC(CH₃)₂CH₂ | O |
| A377 | CF₃ | CH=CHCH₂ | CH₃OCH(CH₃)CH₂ | O |
| A378 | CF₃ | CH=CHCH₂ | CH₃OCH₂CH(CH₃) | O |
| A379 | CF₃ | CH=CHCH₂ | CH₃OCH₂C(CH₃)₂ | O |
| A380 | CF₃ | CH=CHCH₂ | CH₃OCH(CH₃) | O |
| A381 | CF₃ | CH=CHCH₂ | CH₃OC(CH₃)₂ | O |
| A382 | CF₃ | CH=CHCH₂ | HC≡CCH₂ | O |
| A383 | CF₃ | CH=CHCH₂ | H₂C=CHCH₂ | O |
| A384 | CF₃ | CH=CHCH₂ | CH₃C≡CCH₂ | O |
| A385 | CF₃ | CH=CHCH₂ | cyclopropyl-CH | O |
| A386 | CF₃ | CH=CHCH₂ | oxiranyl-CH (2 isomers) | O |
| A387 | CF₃ | CH=CHCH₂ | cyclobutyl-CH | O |
| A388 | CF₃ | CH=CHCH₂ | oxetanyl-CH | O |
| A389 | CF₃ | CH=CHCH₂ | cyclopentyl-CH | O |
| A390 | CF₃ | CH=CHCH₂ | tetrahydrofuranyl-CH | O |
| A391 | CF₃ | CH=CHCH₂ | cyclohexyl-CH | O |
| A392 | CF₃ | CH=CHCH₂ | tetrahydropyranyl-CH | O |

-continued

| | | | | |
|---|---|---|---|---|
| A393 | CF₃ | CH=CHCH₂ | tetrahydropyran-2-yl | O |
| A394 | CF₃ | CH=CHCH₂ | tetrahydropyran-4-yl | O |
| A395 | CF₃ | CH=CHCH₂ | 1,3-dioxan-2-yl | O |
| A396 | CF₃ | CH=CHCH₂ | phenyl | O |
| A397 | CF₃ | CH=CHCH₂ | 2-methoxyphenyl | O |
| A398 | CF₃ | CH=CHCH₂ | 2-hydroxyphenyl | O |
| A399 | CF₃ | CH=CHCH₂ | 3-methoxyphenyl | O |
| A400 | CF₃ | CH=CHCH₂ | 3-hydroxyphenyl | O |
| A401 | CF₃ | CH=CHCH₂ | thiophen-3-yl | O |
| A402 | CF₃ | CH=CHCH₂ | 2,3-dimethylthiophen-4-yl | O |
| A403 | CF₃ | CH=CHCH₂ | 1,3-dimethyl-1H-pyrazol-5-yl | O |
| A404 | CF₃ | CH=CHCH₂ | 1-methyl-1H-pyrazol-5-yl | O |

-continued
| | | | | | |
|---|---|---|---|---|---|
| A405 | CF$_3$ | CH=CH$_2$ | 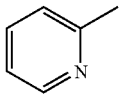 | | O |
| A406 | CF$_3$ | CH=CH$_2$ | 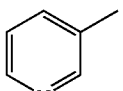 | | O |
| A407 | CF$_3$ | CH=CH$_2$ | 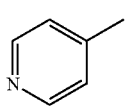 | | O |
| A408 | CF$_3$ | CH=CH$_2$ | 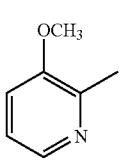 | | O |
| A409 | CF$_3$ | CH=CH$_2$ | 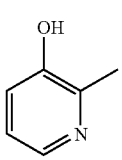 | | O |
| A410 | CF$_3$ | CH=CH$_2$ | 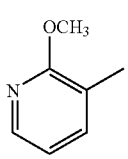 | | O |
| A411 | CF$_3$ | CH=CH$_2$ | 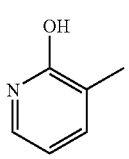 | | O |
| A412 | CF$_3$ | CH=CH$_2$ | 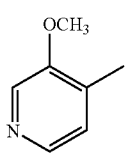 | | O |
| A413 | CF$_3$ | CH=CH$_2$ | 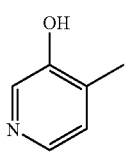 | | O |
| A414 | CF$_3$ | CH=CH$_2$ | 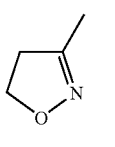 | | O |
| A415 | CF$_3$ | CH=CH$_2$ | 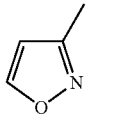 | | O |

-continued
| | | | | |
|---|---|---|---|---|
| A416 | CF$_3$ | CH=CHCH$_2$ | 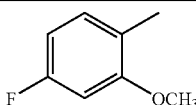 | O |
| A417 | CF$_3$ | CH=CHCH$_2$ | 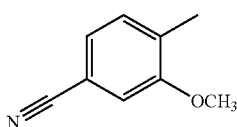 | O |
| A418 | CF$_3$ | CH=CHCH$_2$ | 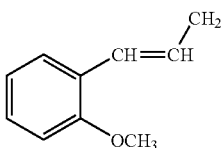 | O |
| A419 | CF$_3$ | CH=CHCH$_2$ | 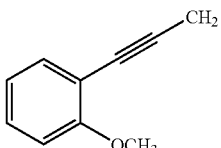 | O |
| A420 | CF$_3$ | CH=CHCH$_2$ | 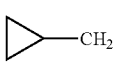 | O |
| A421 | CF$_3$ | CH=CHCH$_2$ | 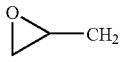 | O |
| A422 | CF$_3$ | CH=CHCH$_2$ |  | O |
| A423 | CF$_3$ | CH=CHCH$_2$ |  | O |
| A424 | CF$_3$ | CH=CHCH$_2$ | 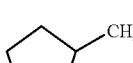 | O |
| A425 | CF$_3$ | CH=CHCH$_2$ | 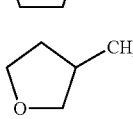 | O |
| A426 | CF$_3$ | CH=CHCH$_2$ | 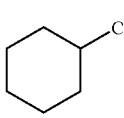 | O |
| A427 | CF$_3$ | CH=CHCH$_2$ | 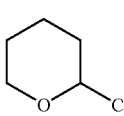 | O |
| A428 | CF$_3$ | CH=CHCH$_2$ | 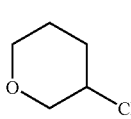 | O |
| A429 | CF$_3$ | CH=CHCH$_2$ | 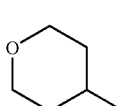 | O |

-continued
| | | | | |
|---|---|---|---|---|
| A430 | CF₃ | CH=CHCH₂ | 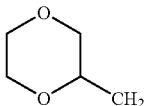 | O |
| A431 | CF₃ | CH=CHCH₂ | 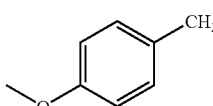 | O |
| A432 | CF₃ | CH=CHCH₂ | 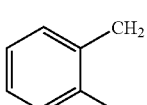 | O |
| A433 | CF₃ | CH=CHCH₂ | 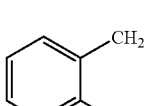 | O |
| A434 | CF₃ | CH=CHCH₂ | 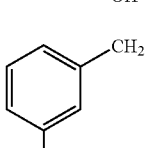 | O |
| A435 | CF₃ | CH=CHCH₂ | 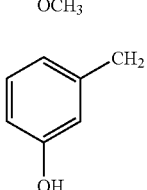 | O |
| A436 | CF₃ | CH=CHCH₂ | 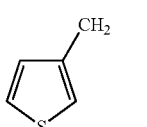 | O |
| A437 | CF₃ | CH=CHCH₂ | 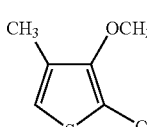 | O |
| A438 | CF₃ | CH=CHCH₂ | 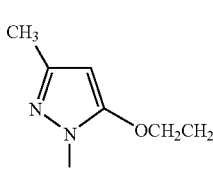 | O |
| A439 | CF₃ | CH=CHCH₂ | 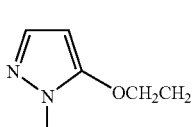 | O |
| A440 | CF₃ | CH=CHCH₂ | 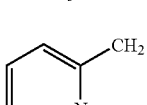 | O |

-continued
| | | | | | |
|---|---|---|---|---|---|
| A441 | CF$_3$ | CH=CHCH$_2$ | 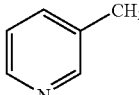 | O | |
| A442 | CF$_3$ | CH=CHCH$_2$ | 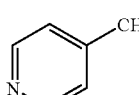 | O | |
| A443 | CF$_3$ | CH=CHCH$_2$ | 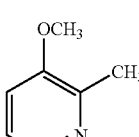 | O | |
| A444 | CF$_3$ | CH=CHCH$_2$ | 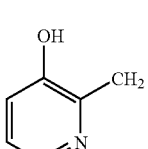 | O | |
| A445 | CF$_3$ | CH=CHCH$_2$ | 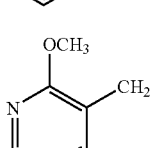 | O | |
| A446 | CF$_3$ | CH=CHCH$_2$ | 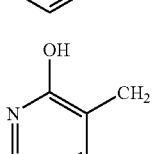 | O | |
| A447 | CF$_3$ | CH=CHCH$_2$ | 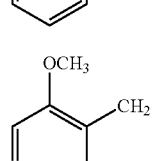 | O | |
| A448 | CF$_3$ | CH=CHCH$_2$ | 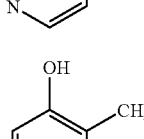 | O | |
| A449 | CF$_3$ | CH=CHCH$_2$ | 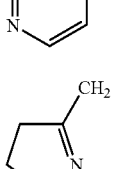 | O | |
| A450 | CF$_3$ | CH=CHCH$_2$ | 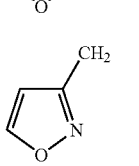 | O | |
| A451 | CF$_3$ | CH=CHCH$_2$ | 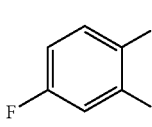 | O | |

-continued

| | | | | | |
|---|---|---|---|---|---|
| A452 | CF$_3$ | CH=CHCH$_2$ | 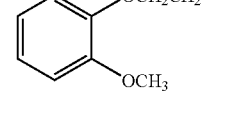 | | O |
| A453 | CF$_3$ | CH=CHCH$_2$ | 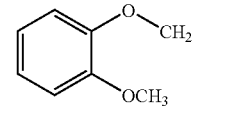 | | O |
| A454 | CF$_3$ | CH=CHCH$_2$ | 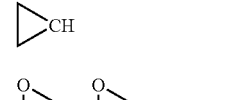 | | O |
| A455 | CF$_3$ | C≡CCH$_2$ | CH$_3$ | | O |
| A456 | CF$_3$ | C≡CCH$_2$ | CH$_3$CH$_2$ | | O |
| A457 | CF$_3$ | C≡CCH$_2$ | (CH$_3$)$_2$CH | | O |
| A458 | CF$_3$ | C≡CCH$_2$ | PhCH$_2$ | | O |
| A459 | CF$_3$ | C≡CCH$_2$ | CH$_3$ | | S |
| A460 | CF$_3$ | C≡CCH$_2$ | CH$_3$ | | SO |
| A461 | CF$_3$ | C≡CCH$_2$ | CH$_3$ | | SO$_2$ |
| A462 | CF$_3$ | C≡CCH$_2$ | CH$_3$CH$_2$CH$_2$ | | O |
| A463 | CF$_3$ | C≡CCH$_2$ | CH$_3$OCH$_2$ | | O |
| A464 | CF$_3$ | C≡CCH$_2$ | CH$_3$CH$_2$OCH$_2$ | | O |
| A465 | CF$_3$ | C≡CCH$_2$ | CH$_3$OCH$_2$CH$_2$ | | O |
| A466 | CF$_3$ | C≡CCH$_2$ | CH$_3$CH$_2$OCH$_2$CH$_2$ | | O |
| A467 | CF$_3$ | C≡CCH$_2$ | CH$_3$OC(CH$_3$)$_2$CH$_2$ | | O |
| A468 | CF$_3$ | C≡CCH$_2$ | CH$_3$OCH(CH$_3$)CH$_2$ | | O |
| A469 | CF$_3$ | C≡CCH$_2$ | CH$_3$OCH$_2$CH(CH$_3$) | | O |
| A470 | CF$_3$ | C≡CCH$_2$ | CH$_3$OCH$_2$C(CH$_3$)$_2$ | | O |
| A471 | CF$_3$ | C≡CCH$_2$ | CH$_3$OCH(CH$_3$) | | O |
| A472 | CF$_3$ | C≡CCH$_2$ | CH$_3$OC(CH$_3$)$_2$ | | O |
| A473 | CF$_3$ | C≡CCH$_2$ | HC≡CCH$_2$ | | O |
| A474 | CF$_3$ | C≡CCH$_2$ | H$_2$C=CHCH$_2$ | | O |
| A475 | CF$_3$ | C≡CCH$_2$ | CH$_3$C≡CCH$_2$ | | O |
| A476 | CF$_3$ | C≡CCH$_2$ | 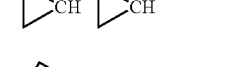 | | O |
| A477 | CF$_3$ | C≡CCH$_2$ |  | | O |
| A478 | CF$_3$ | C≡CCH$_2$ |  | | O |
| A479 | CF$_3$ | C≡CCH$_2$ |  | | O |
| A480 | CF$_3$ | C≡CCH$_2$ |  | | O |
| A481 | CF$_3$ | C≡CCH$_2$ |  | | O |
| A482 | CF$_3$ | C≡CCH$_2$ |  | | O |
| A483 | CF$_3$ | C≡CCH$_2$ | | | O |

-continued

| | | | | |
|---|---|---|---|---|
| A484 | CF$_3$ | C≡CH$_2$ | tetrahydropyran-4-yl (CH at 4-position) | O |
| A485 | CF$_3$ | C≡CH$_2$ | tetrahydropyran-4-yl | O |
| A486 | CF$_3$ | C≡CH$_2$ | 1,3-dioxan-2-yl | O |
| A487 | CF$_3$ | C≡CH$_2$ | phenyl | O |
| A488 | CF$_3$ | C≡CH$_2$ | 2-methoxyphenyl | O |
| A489 | CF$_3$ | C≡CH$_2$ | 2-hydroxyphenyl | O |
| A490 | CF$_3$ | C≡CH$_2$ | 3-methoxyphenyl | O |
| A491 | CF$_3$ | C≡CH$_2$ | 3-hydroxyphenyl | O |
| A492 | CF$_3$ | C≡CH$_2$ | thiophen-3-yl | O |
| A493 | CF$_3$ | C≡CH$_2$ | 2,3-dimethylthiophen-4-yl | O |
| A494 | CF$_3$ | C≡CH$_2$ | 1,3-dimethyl-1H-pyrazol-5-yl | O |
| A495 | CF$_3$ | C≡CH$_2$ | 1-methyl-1H-pyrazol-5-yl | O |

-continued
| A496 | CF₃ | C≡CCH₂ | 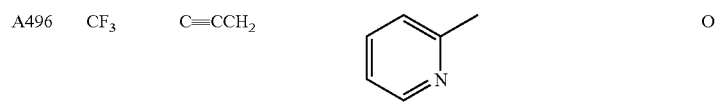 | O |
| A497 | CF₃ | C≡CCH₂ | 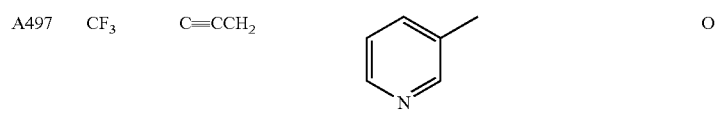 | O |
| A498 | CF₃ | C≡CCH₂ | 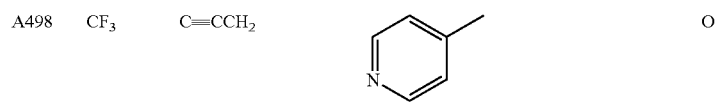 | O |
| A499 | CF₃ | C≡CCH₂ | 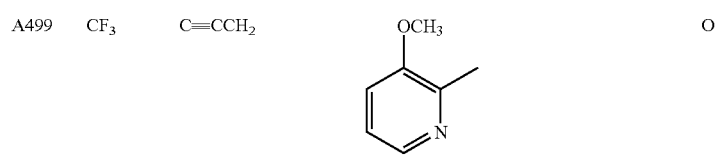 | O |
| A500 | CF₃ | C≡CCH₂ | 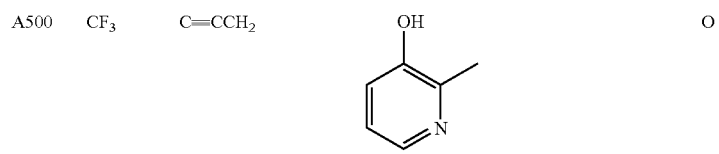 | O |
| A501 | CF₃ | C≡CCH₂ | 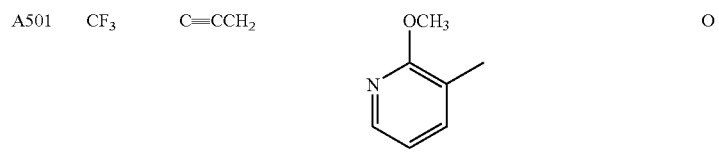 | O |
| A502 | CF₃ | C≡CCH₂ | 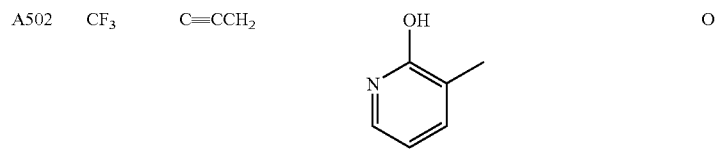 | O |
| A503 | CF₃ | C≡CCH₂ | 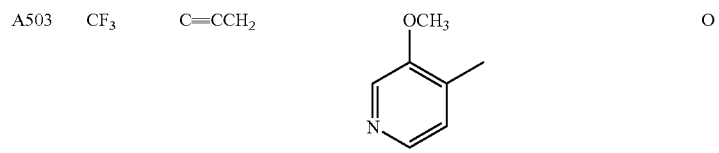 | O |
| A504 | CF₃ | C≡CCH₂ | 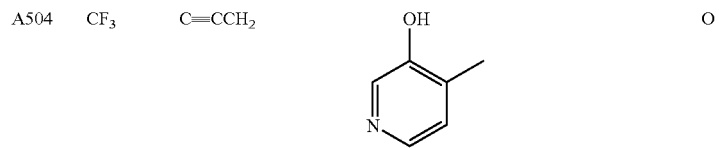 | O |
| A505 | CF₃ | C≡CCH₂ | 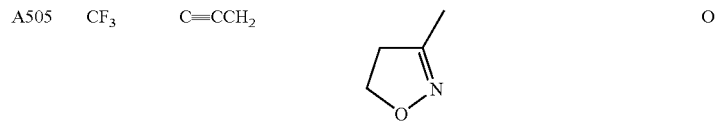 | O |
| A506 | CF₃ | C≡CCH₂ | 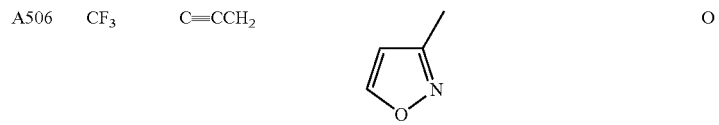 | O |

-continued
| | | | | |
|---|---|---|---|---|
| A507 | CF$_3$ | C≡CH$_2$ | 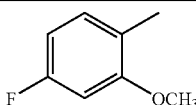 | O |
| A508 | CF$_3$ | C≡CH$_2$ | 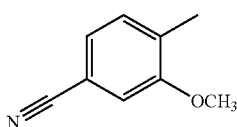 | O |
| A509 | CF$_3$ | C≡CH$_2$ | 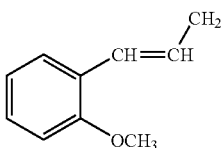 | O |
| A510 | CF$_3$ | C≡CH$_2$ | 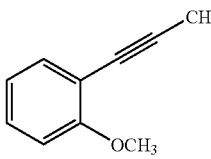 | O |
| A511 | CF$_3$ | C≡CH$_2$ | 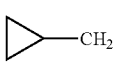 | O |
| A512 | CF$_3$ | C≡CH$_2$ | 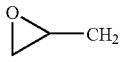 | O |
| A513 | CF$_3$ | C≡CH$_2$ |  | O |
| A514 | CF$_3$ | C≡CH$_2$ |  | O |
| A515 | CF$_3$ | C≡CH$_2$ | 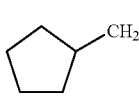 | O |
| A516 | CF$_3$ | C≡CH$_2$ | 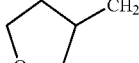 | O |
| A517 | CF$_3$ | C≡CH$_2$ | 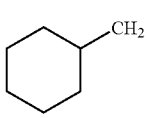 | O |
| A518 | CF$_3$ | C≡CH$_2$ | 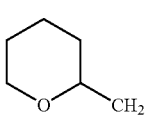 | O |
| A519 | CF$_3$ | C≡CH$_2$ | 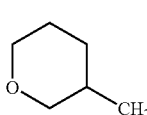 | O |
| A520 | CF$_3$ | C≡CH$_2$ | 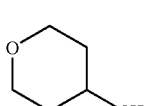 | O |

-continued
| | | | | |
|---|---|---|---|---|
| A521 | CF$_3$ | C≡CH$_2$ | 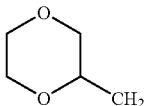 | O |
| A521a | CF$_3$ | C≡CH$_2$ | 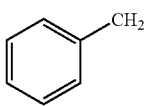 | O |
| A522 | CF$_3$ | C≡CH$_2$ | 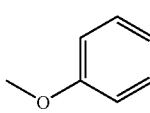 | O |
| A523 | CF$_3$ | C≡CH$_2$ | 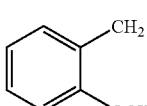 | O |
| A524 | CF$_3$ | C≡CH$_2$ | 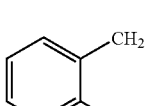 | O |
| A525 | CF$_3$ | C≡CH$_2$ | 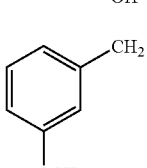 | O |
| A526 | CF$_3$ | C≡CH$_2$ | 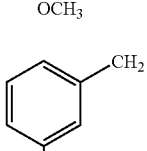 | O |
| A527 | CF$_3$ | C≡CH$_2$ | 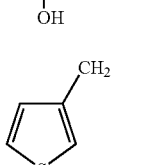 | O |
| A528 | CF$_3$ | C≡CH$_2$ | 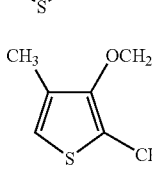 | O |
| A529 | CF$_3$ | C≡CH$_2$ | 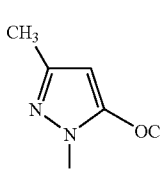 | O |
| A530 | CF$_3$ | C≡CH$_2$ | 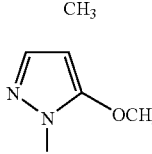 | O |

-continued
| | | | | |
|---|---|---|---|---|
| A531 | CF₃ | C≡CH₂ | 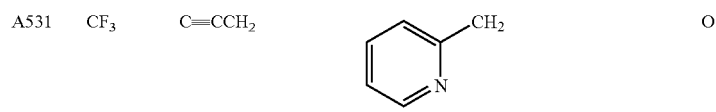 | O |
| A532 | CF₃ | C≡CH₂ | 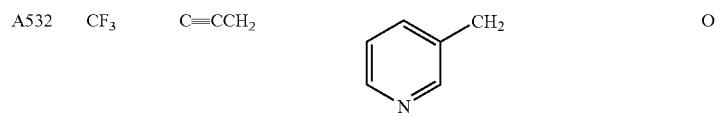 | O |
| | | | | |
|---|---|---|---|---|
| A533 | CF₃ | C≡CH₂ | 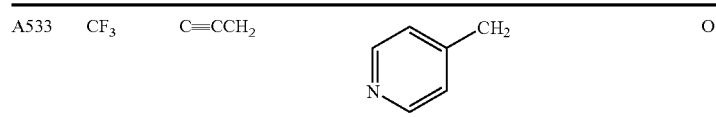 | O |
| A534 | CF₃ | C≡CH₂ | 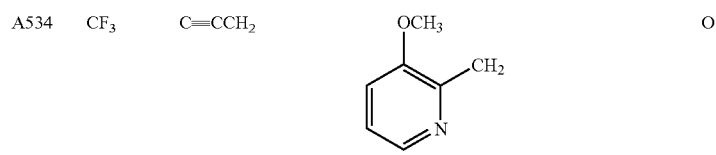 | O |
| A535 | CF₃ | C≡CH₂ | 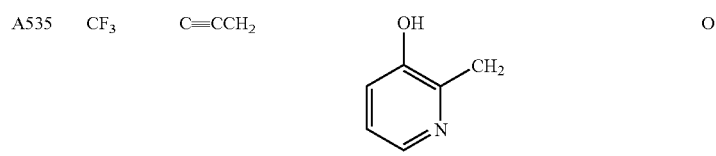 | O |
| A536 | CF₃ | C≡CH₂ | 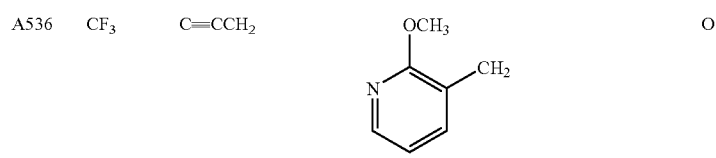 | O |
| A537 | CF₃ | C≡CH₂ | 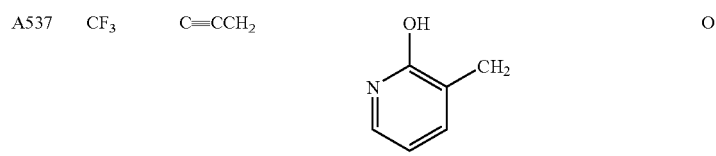 | O |
| A538 | CF₃ | C≡CH₂ | 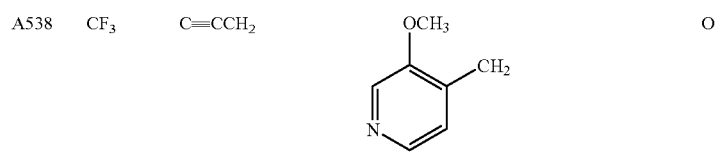 | O |
| A539 | CF₃ | C≡CH₂ | 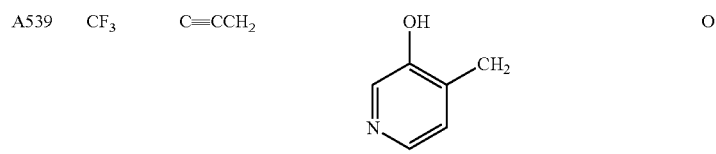 | O |
| A540 | CF₃ | C≡CH₂ | 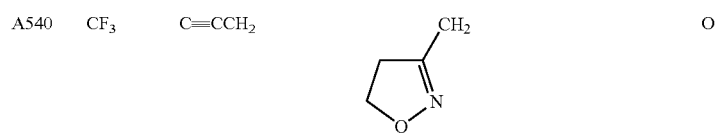 | O |

-continued

| | | | | | |
|---|---|---|---|---|---|
| A541 | CF₃ | C≡CCH₂ | 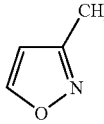 | | O |
| A542 | CF₃ | C≡CCH₂ | 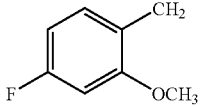 | | O |
| A543 | CF₃ | C≡CCH₂ | 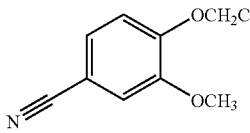 | | O |
| A544 | CF₃ | C≡CCH₂ | 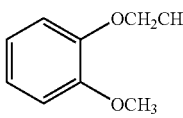 | | O |
| A545 | CF₃ | C≡CCH₂ | 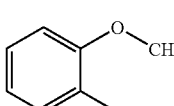 | | O |
| A546 | CF₂Cl | CH₂ | CH₃ | | O |
| A547 | CF₂Cl | CH₂ | CH₃CH₂ | | O |
| A548 | CF₂Cl | CH₂ | (CH₃)₂CH | | O |
| A549 | CF₂Cl | CH₂ | PhCH₂ | | O |
| A550 | CF₂Cl | CH₂ | CH₃ | | S |
| A551 | CF₂Cl | CH₂ | CH₃ | | SO |
| A552 | CF₂Cl | CH₂ | CH₃ | | SO₂ |
| A553 | CF₂Cl | CH₂ | CH₃CH₂CH₂ | | O |
| A554 | CF₂Cl | CH₂ | CH₃OCH₂ | | O |
| A555 | CF₂Cl | CH₂ | CH₃CH₂OCH₂ | | O |
| A556 | CF₂Cl | CH₂ | CH₃OCH₂CH₂ | | O |
| A557 | CF₂Cl | CH₂ | CH₃CH₂OCH₂CH₂ | | O |
| A558 | CF₂Cl | CH₂ | CH₃OC(CH₃)₂CH₂ | | O |
| A559 | CF₂Cl | CH₂ | CH₃OCH(CH₃)CH₂ | | O |
| A560 | CF₂Cl | CH₂ | CH₃OCH₂CH(CH₃) | | O |
| A561 | CF₂Cl | CH₂ | CH₃OCH₂C(CH₃)₂ | | O |
| A562 | CF₂Cl | CH₂ | CH₃OCH(CH₃) | | O |
| A563 | CF₂Cl | CH₂ | CH₃OC(CH₃)₂ | | O |
| A564 | CF₂Cl | CH₂ | HC≡CCH₂ | | O |
| A565 | CF₂Cl | CH₂ | H₂C=CHCH₂ | | O |
| A566 | CF₂Cl | CH₂ | CH₃C≡CCH₂ | | O |
| A567 | CF₂Cl | CH₂ |  | | O |
| A568 | CF₂Cl | CH₂ |  | | O |
| A569 | CF₂Cl | CH₂ |  | | O |
| A570 | CF₂Cl | CH₂ |  | | O |
| A571 | CF₂Cl | CH₂ |  | | O |
| A572 | CF₂Cl | CH₂ |  | | O |

-continued
| | | | | |
|---|---|---|---|---|
| A573 | CF$_2$Cl | CH$_2$ | 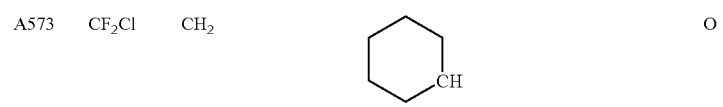 | O |
| A574 | CF$_2$Cl | CH$_2$ | 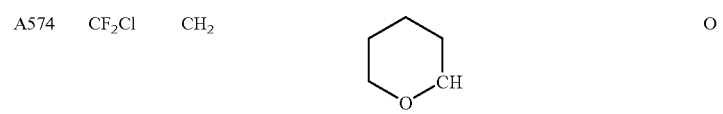 | O |
| A575 | CF$_2$Cl | CH$_2$ | 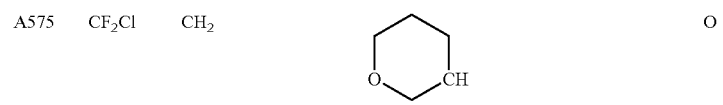 | O |
| A576 | CF$_2$Cl | CH$_2$ | 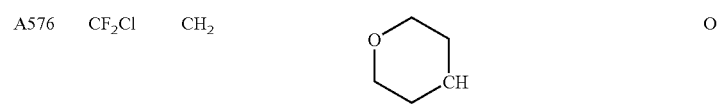 | O |
| A577 | CF$_2$Cl | CH$_2$ | 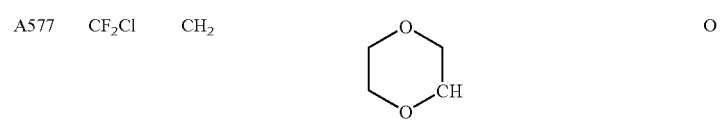 | O |
| A578 | CF$_2$Cl | CH$_2$ | 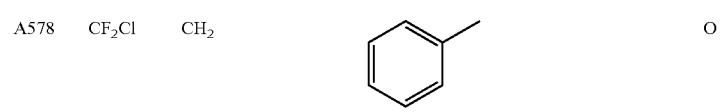 | O |
| A579 | CF$_2$Cl | CH$_2$ | 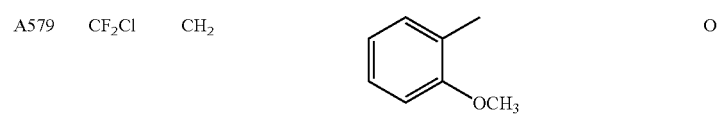 | O |
| A580 | CF$_2$Cl | CH$_2$ | 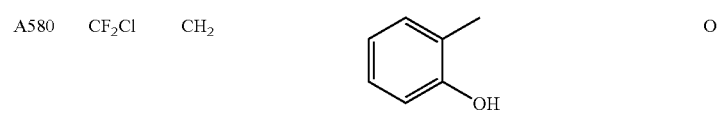 | O |
| A581 | CF$_2$Cl | CH$_2$ | 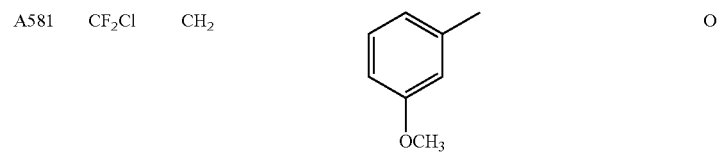 | O |
| A582 | CF$_2$Cl | CH$_2$ | 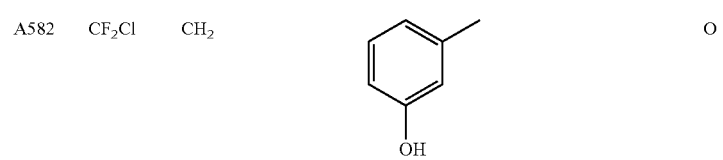 | O |
| A583 | CF$_2$Cl | CH$_2$ | 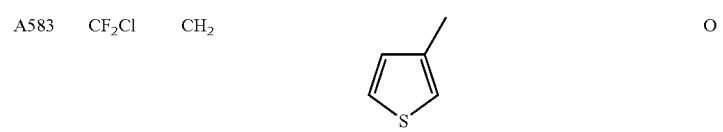 | O |
| A584 | CF$_2$Cl | CH$_2$ | 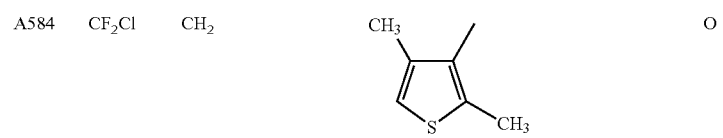 | O |

-continued
| | | | | |
|---|---|---|---|---|
| A585 | CF$_2$Cl | CH$_2$ | 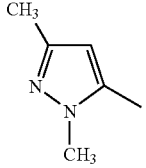 | O |
| A586 | CF$_2$Cl | CH$_2$ | 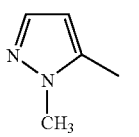 | O |
| A587 | CF$_2$Cl | CH$_2$ | 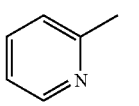 | O |
| A588 | CF$_2$Cl | CH$_2$ | 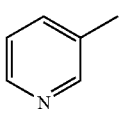 | O |
| A589 | CF$_2$Cl | CH$_2$ | 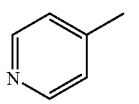 | O |
| A590 | CF$_2$Cl | CH$_2$ | 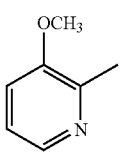 | O |
| A591 | CF$_2$Cl | CH$_2$ | 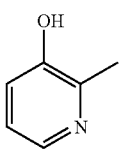 | O |
| A592 | CF$_2$Cl | CH$_2$ | 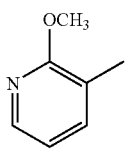 | O |
| A593 | CF$_2$Cl | CH$_2$ | 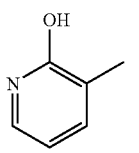 | O |
| A594 | CF$_2$Cl | CH$_2$ | 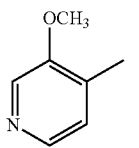 | O |
| A595 | CF$_2$Cl | CH$_2$ | 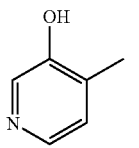 | O |

-continued
| | | | | | |
|---|---|---|---|---|---|
| A596 | CF$_2$Cl | CH$_2$ | 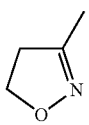 | | O |
| A597 | CF$_2$Cl | CH$_2$ | 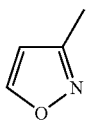 | | O |
| A598 | CF$_2$Cl | CH$_2$ | 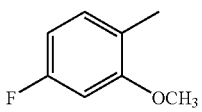 | | O |
| A599 | CF$_2$Cl | CH$_2$ | 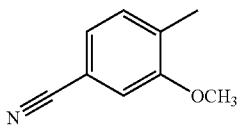 | | O |
| A600 | CF$_2$Cl | CH$_2$ | 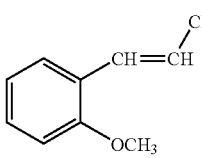 | | O |
| A601 | CF$_2$Cl | CH$_2$ | 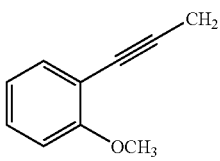 | | O |
| A602 | CF$_2$Cl | CH$_2$ | 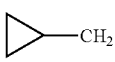 | | O |
| A603 | CF$_2$Cl | CH$_2$ | 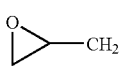 | | O |
| A604 | CF$_2$Cl | CH$_2$ |  | | O |
| A605 | CF$_2$Cl | CH$_2$ |  | | O |
| A606 | CF$_2$Cl | CH$_2$ | 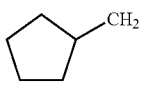 | | O |
| A607 | CF$_2$Cl | CH$_2$ | 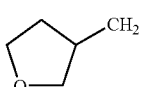 | | O |
| A608 | CF$_2$Cl | CH$_2$ | 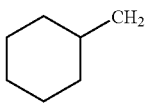 | | O |

-continued
| | | | | | |
|---|---|---|---|---|---|
| A609 | CF$_2$Cl | CH$_2$ | 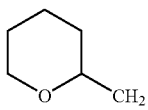 | O | |
| A610 | CF$_2$Cl | CH$_2$ | 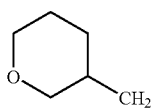 | O | |
| A611 | CF$_2$Cl | CH$_2$ | 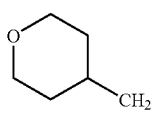 | O | |
| A612 | CF$_2$Cl | CH$_2$ | 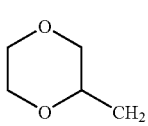 | O | |
| A613 | CF$_2$Cl | CH$_2$ | 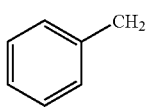 | O | |
| A614 | CF$_2$Cl | CH$_2$ | 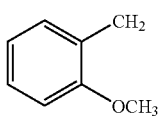 | O | |
| A615 | CF$_2$Cl | CH$_2$ | 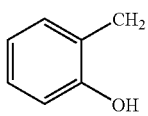 | O | |
| A616 | CF$_2$Cl | CH$_2$ | 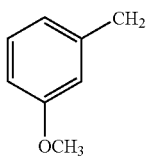 | O | |
| A617 | CF$_2$Cl | CH$_2$ | 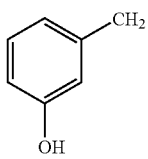 | O | |
| A618 | CF$_2$Cl | CH$_2$ | 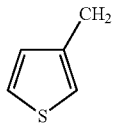 | O | |
| A619 | CF$_2$Cl | CH$_2$ | 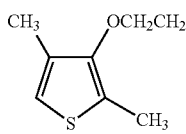 | O | |

-continued
| | | | | |
|---|---|---|---|---|
| A620 | CF$_2$Cl | CH$_2$ | 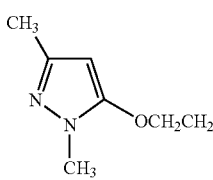 | O |
| A621 | CF$_2$Cl | CH$_2$ | 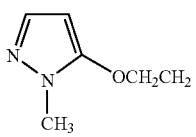 | O |
| A622 | CF$_2$Cl | CH$_2$ | 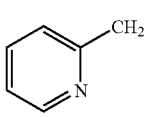 | O |
| A623 | CF$_2$Cl | CH$_2$ | 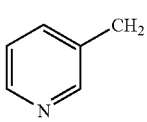 | O |
| A624 | CF$_2$Cl | CH$_2$ | 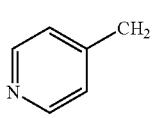 | O |
| A625 | CF$_2$Cl | CH$_2$ | 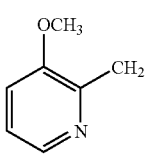 | O |
| A626 | CF$_2$Cl | CH$_2$ | 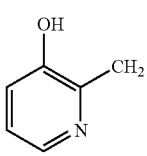 | O |
| A627 | CF$_2$Cl | CH$_2$ | 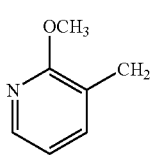 | O |
| A628 | CF$_2$Cl | CH$_2$ | 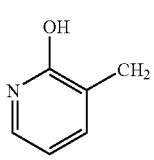 | O |
| A629 | CF$_2$Cl | CH$_2$ | 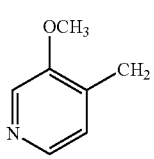 | O |

-continued

| | | | | |
|---|---|---|---|---|
| A630 | CF₂Cl | CH₂ | 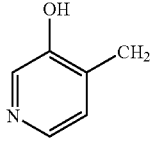 | O |
| A631 | CF₂Cl | CH₂ | 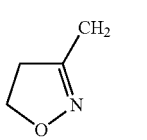 | O |
| A632 | CF₂Cl | CH₂ | 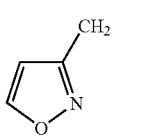 | O |
| A633 | CF₂Cl | CH₂ | 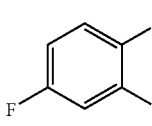 | O |
| A634 | CF₂Cl | CH₂ | 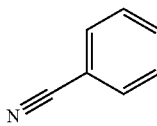 | O |
| A635 | CF₂Cl | CH₂ | 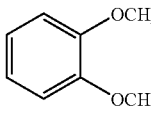 | O |
| A636 | CF₂Cl | CH₂ | 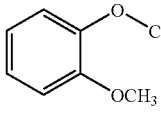 | O |
| A637 | CF₂Cl | CH₂ | CH₃ | O |
| A638 | CF₂Cl | CH₂ | CH₂CH₃ | O |
| A639 | CF₂Cl | CH₂ | (CH₃)₂CH | O |
| A640 | CF₂Cl | CH₂ | PhCH₂ | O |
| A641 | CF₂Cl | CH₂ | CH₃ | S |
| A642 | CF₂Cl | CH₂ | CH₃ | O |
| A643 | CF₂Cl | CH₂ | CH₃ | O |
| A644 | CF₂Cl | CH₂ | CH₃OCH₂ | O |
| A645 | CF₂Cl | CH₂ | CH₃CH₂OCH₂ | O |
| A646 | CF₂Cl | CH₂ | CH₃OCH₂CH₂ | O |
| A647 | CF₂Cl | CH₂ | CH₃CH₂OCH₂CH₂ | O |
| A648 | CF₂Cl | CH₂ | CH₃OC(CH₃)₂CH₂ | O |
| A649 | CF₂Cl | CH₂ | CH₃OCH(CH₃)CH₂ | O |
| A650 | CF₂Cl | CH₂ | CH₃OCH₂CH(CH₃) | O |
| A651 | CF₂Cl | CH₂ | CH₃OCH₂C(CH₃)₂ | O |
| A652 | CF₂Cl | CH₂ | CH₃OCH(CH₃) | O |
| A653 | CF₂Cl | CH₂ | CH₃OC(CH₃)₂ | O |
| A654 | CF₂Cl | CH₂ | HC≡CCH₂ | O |
| A655 | CF₂Cl | CH₂ | H₂C=CHCH₂ | O |
| A656 | CF₂Cl | CH₂ | CH₃C≡CCH₂ | O |
| A657 | CF₂Cl | CH₂ |  | O |
| A658 | CF₂Cl | CH₂ |  | O |
| A659 | CF₂Cl | CH₂ | 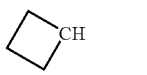 | O |

-continued
| | | | | |
|---|---|---|---|---|
| A660 | CF$_2$Cl | CH$_2$ |  | O |
| A661 | CF$_2$Cl | CH$_2$ |  | O |
| A662 | CF$_2$Cl | CH$_2$ |  | O |
| A663 | CF$_2$Cl | CH$_2$ | 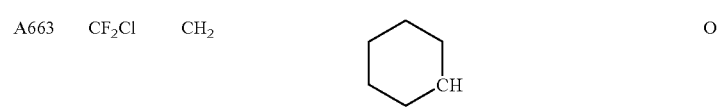 | O |
| A664 | CF$_2$Cl | CH$_2$ | 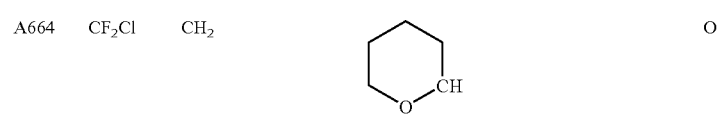 | O |
| A665 | CF$_2$Cl | CH$_2$ | 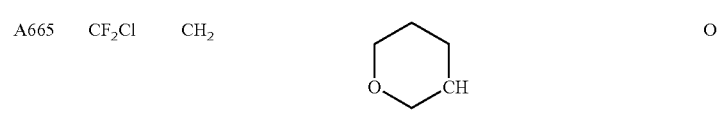 | O |
| A666 | CF$_2$Cl | CH$_2$ | 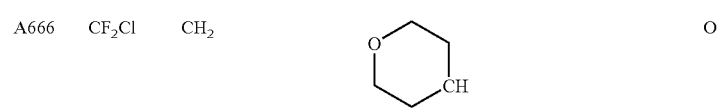 | O |
| A667 | CF$_2$Cl | CH$_2$ | 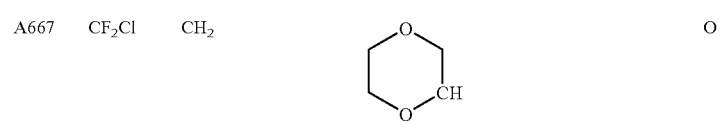 | O |
| A668 | CF$_2$Cl | CH$_2$ | 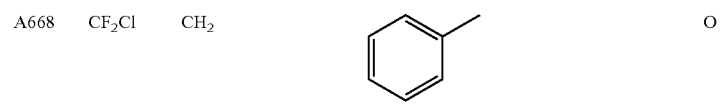 | O |
| A669 | CF$_2$Cl | CH$_2$ | 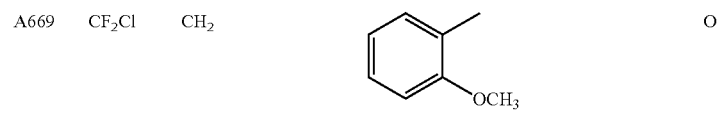 | O |
| A670 | CF$_2$Cl | CH$_2$ | 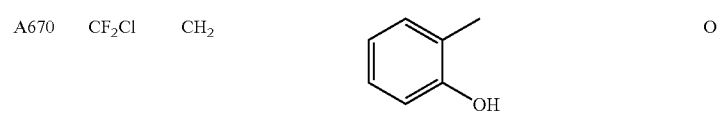 | O |
| A671 | CF$_2$Cl | CH$_2$ | 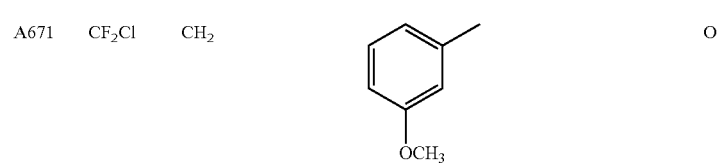 | O |
| A672 | CF$_2$Cl | CH$_2$ | 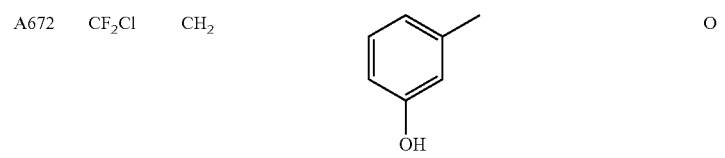 | O |

| | | | | |
|---|---|---|---|---|
| A673 | CF$_2$Cl | CH$_2$ | 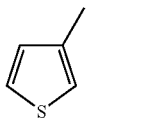 | O |
| A674 | CF$_2$Cl | CH$_2$ | 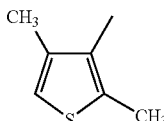 | O |
| A675 | CF$_2$Cl | CH$_2$ | 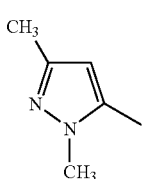 | O |
| A676 | CF$_2$Cl | CH$_2$ | 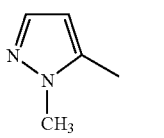 | O |
| A677 | CF$_2$Cl | CH$_2$ | 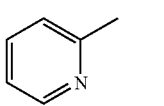 | O |
| A678 | CF$_2$Cl | CH$_2$ | 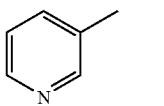 | O |
| A679 | CF$_2$Cl | CH$_2$ | 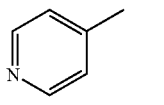 | O |
| A680 | CF$_2$Cl | CH$_2$ | 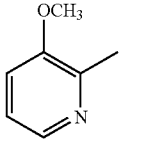 | O |
| A681 | CF$_2$Cl | CH$_2$ | 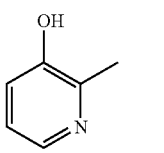 | O |
| A682 | CF$_2$Cl | CH$_2$ | 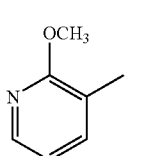 | S |
| A683 | CF$_2$Cl | CH$_2$ | 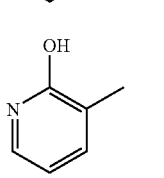 | SO |

-continued

| | | | | |
|---|---|---|---|---|
| A684 | CF₂Cl | CH₂ | 3-methoxy-4-methylpyridine | SO₂ |
| A685 | CF₂Cl | CH₂ | 3-hydroxy-4-methylpyridine | O |
| A686 | CF₂Cl | CH₂ | 3-methyl-4,5-dihydroisoxazole | O |
| A687 | CF₂Cl | CH₂ | 3-methylisoxazole | O |
| A688 | CF₂Cl | CH₂ | 4-fluoro-2-methoxy-1-methylbenzene | O |
| A689 | CF₂Cl | CH₂ | 3-methoxy-4-methylbenzonitrile | O |
| A690 | CF₂Cl | CH₂ | 1-(2-methoxyphenyl)allyl | O |
| A691 | CF₂Cl | CH₂ | 3-(2-methoxyphenyl)prop-2-ynyl | O |
| A692 | CF₂Cl | CH₂ | cyclopropylmethyl | O |
| A693 | CF₂Cl | CH₂ | oxiranylmethyl | O |
| A694 | CF₂Cl | CH₂ | cyclobutylmethyl | O |
| A695 | CF₂Cl | CH₂ | oxetan-3-ylmethyl | O |
| A696 | CF₂Cl | CH₂ | cyclopentylmethyl | O |

-continued
| | | | | | |
|---|---|---|---|---|---|
| A697 | CF$_2$Cl | CH$_2$ | 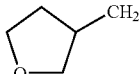 | O | |
| A698 | CF$_2$Cl | CH$_2$ | 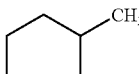 | O | |
| A699 | CF$_2$Cl | CH$_2$ | 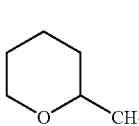 | O | |
| A700 | CF$_2$Cl | CH$_2$ | 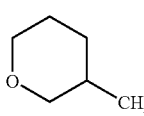 | O | |
| A701 | CF$_2$Cl | CH$_2$ | 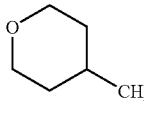 | O | |
| A702 | CF$_2$Cl | CH$_2$ | 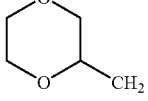 | O | |
| A703 | CF$_2$Cl | CH$_2$ | 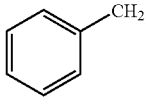 | O | |
| A704 | CF$_2$Cl | CH$_2$ | 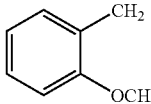 | O | |
| A705 | CF$_2$Cl | CH$_2$ | 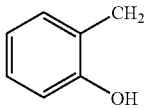 | O | |
| A706 | CF$_2$Cl | CH$_2$ | 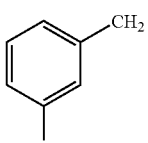 | O | |
| A707 | CF$_2$Cl | CH$_2$ | 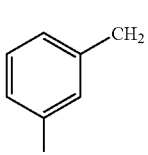 | O | |
| A708 | CF$_2$Cl | CH$_2$ | 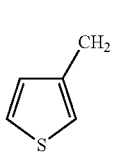 | O | |

-continued
| | | | | | |
|---|---|---|---|---|---|
| A709 | CF$_2$Cl | CH$_2$ | 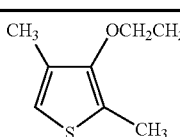 | O |
| A710 | CF$_2$Cl | CH$_2$ | 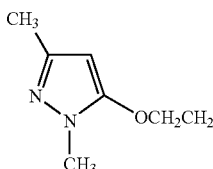 | O |
| A711 | CF$_2$Cl | CH$_2$ | 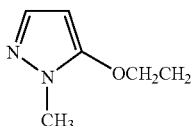 | O |
| A712 | CF$_2$Cl | CH$_2$ | 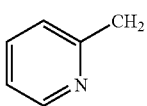 | O |
| A713 | CF$_2$Cl | CH$_2$ | 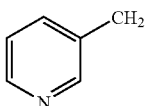 | O |
| A714 | CF$_2$Cl | CH$_2$ | 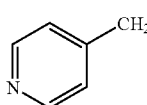 | O |
| A715 | CF$_2$Cl | CH$_2$ | 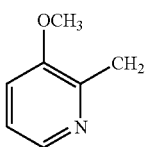 | O |
| A716 | CF$_2$Cl | CH$_2$ | 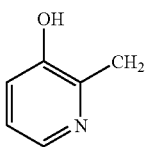 | O |
| A717 | CF$_2$Cl | CH$_2$ | 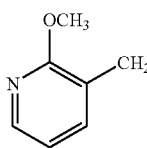 | O |
| A718 | CF$_2$Cl | CH$_2$ | 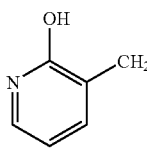 | O |
| A719 | CF$_2$Cl | CH$_2$ | 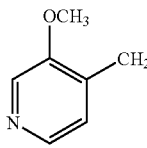 | O |

| | | | | |
|---|---|---|---|---|
| A720 | CF₂Cl | CH₂ | 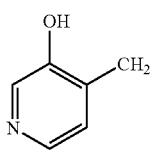 | O |
| A721 | CF₂Cl | CH₂ | 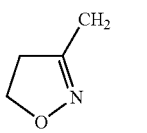 | O |
| A722 | CF₂Cl | CH₂ | 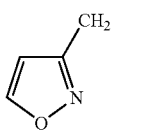 | O |
| A723 | CF₂Cl | CH₂ | 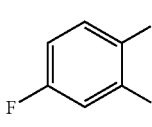 | O |
| A724 | CF₂Cl | CH₂ | 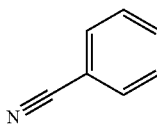 | O |
| A725 | CF₂Cl | CH₂ | 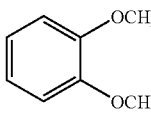 | O |
| A726 | CF₂Cl | CH₂ | 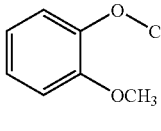 | O |
| A727 | CF₂Cl | CH₂ | CH₃ | O |
| A728 | CF₂Cl | CH₂ | CH₂CH₃ | O |
| A729 | CF₂Cl | CH₂ | (CH₃)₂CH | O |
| A730 | CF₂Cl | CH₂ | PhCH₂ | O |
| A731 | CF₂Cl | CH₂ | CH₃ | S |
| A732 | CF₂Cl | CH₂ | CH₃ | SO |
| A733 | CF₂Cl | CH₂ | CH₃ | SO₂ |
| A734 | CF₂Cl | CH₂ | CH₃OCH₂ | O |
| A735 | CF₂Cl | CH₂ | CH₃CH₂OCH₂ | O |
| A736 | CF₂Cl | CH₂ | CH₃OCH₂CH₂ | O |
| A737 | CF₂Cl | CH₂ | CH₃CH₂OCH₂CH₂ | O |
| A738 | CF₂Cl | CH₂ | CH₃OC(CH₃)₂CH₂ | O |
| A739 | CF₂Cl | CH₂ | CH₃OCH(CH₃)CH₂ | O |
| A740 | CF₂Cl | CH₂ | CH₃OCH₂CH(CH₃) | O |
| A741 | CF₂Cl | CH₂ | CH₃OCH₂C(CH₃)₂ | O |
| A742 | CF₂Cl | CH₂ | CH₃OCH(CH₃) | O |
| A743 | CF₂Cl | CH₂ | CH₃OC(CH₃)₂ | O |
| A744 | CF₂Cl | CH₂ | HC≡CCH₂ | O |
| A745 | CF₂Cl | CH₂ | H₂C=CHCH₂ | O |
| A746 | CF₂Cl | CH₂ | CH₃C≡CCH₂ | O |
| A747 | CF₂Cl | CH₂ |  | O |
| A748 | CF₂Cl | CH₂ |  | O |

-continued
| | | | | |
|---|---|---|---|---|
| A749 | CF$_2$Cl | CH$_2$ |  | O |
| A750 | CF$_2$Cl | CH$_2$ |  | O |
| A751 | CF$_2$Cl | CH$_2$ |  | O |
| A752 | CF$_2$Cl | CH$_2$ |  | O |
| A753 | CF$_2$Cl | CH$_2$ |  | O |
| A754 | CF$_2$Cl | CH$_2$ |  | O |
| A755 | CF$_2$Cl | CH$_2$ |  | O |
| A756 | CF$_2$Cl | CH$_2$ |  | O |
| A757 | CF$_2$Cl | CH$_2$ |  | O |
| A758 | CF$_2$Cl | CH$_2$ | 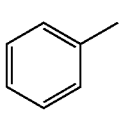 | O |
| A759 | CF$_2$Cl | CH$_2$ | 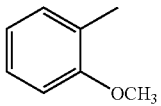 | O |
| A760 | CF$_2$Cl | CH$_2$ | 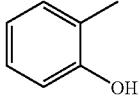 | O |
| A761 | CF$_2$Cl | CH$_2$ | 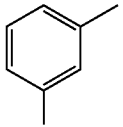 | O |
| A762 | CF$_2$Cl | CH$_2$ | 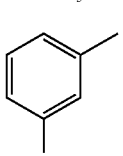 | O |

-continued
| | | | | |
|---|---|---|---|---|
| A763 | CF₂Cl | CH₂ | 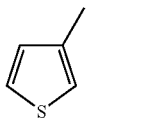 | O |
| A764 | CF₂Cl | CH₂ | 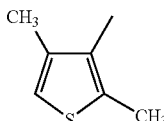 | O |
| A765 | CF₂Cl | CH₂ | 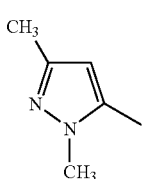 | O |
| A766 | CF₂Cl | CH₂ | 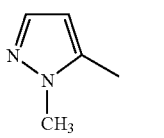 | O |
| A767 | CF₂Cl | CH₂ | 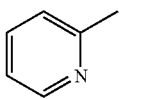 | O |
| A768 | CF₂Cl | CH₂ | 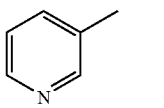 | O |
| A769 | CF₂Cl | CH₂ | 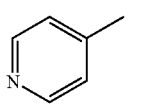 | O |
| A770 | CF₂Cl | CH₂ | 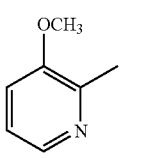 | O |
| A771 | CF₂Cl | CH₂ | 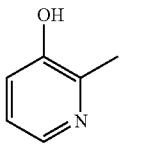 | O |
| A772 | CF₂Cl | CH₂ | 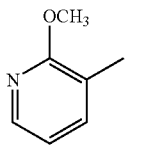 | O |
| A773 | CF₂Cl | CH₂ | 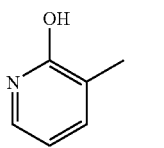 | O |

-continued

| | | | | |
|---|---|---|---|---|
| A774 | CF₂Cl | CH₂ | 3-methoxy-4-methylpyridin-yl | O |
| A775 | CF₂Cl | CH₂ | 3-hydroxy-4-methylpyridin-yl | O |
| A776 | CF₂Cl | CH₂ | 3-methyl-4,5-dihydroisoxazol-yl | O |
| A777 | CF₂Cl | CH₂ | 3-methylisoxazol-yl | O |
| A778 | CF₂Cl | CH₂ | 4-fluoro-2-methoxy-methylphenyl | O |
| A779 | CF₂Cl | CH₂ | 3-methoxy-4-methyl-benzonitrile-yl | O |
| A780 | CF₂Cl | CH₂ | 2-(2-methoxyphenyl)allyl | O |
| A781 | CF₂Cl | CH₂ | 3-(2-methoxyphenyl)prop-2-ynyl | O |
| A782 | CF₂Cl | CH₂ | cyclopropylmethyl | O |
| A783 | CF₂Cl | CH₂ | oxiranylmethyl | O |
| A784 | CF₂Cl | CH₂ | cyclobutylmethyl | O |
| A785 | CF₂Cl | CH₂ | oxetan-3-ylmethyl | O |
| A786 | CF₂Cl | CH₂ | cyclopentylmethyl | O |

-continued
| | | | | | |
|---|---|---|---|---|---|
| A787 | CF₂Cl | CH₂ | 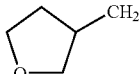 | O | |
| A788 | CF₂Cl | CH₂ | 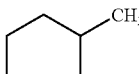 | O | |
| A789 | CF₂Cl | CH₂ | 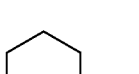 | O | |
| A790 | CF₂Cl | CH₂ | 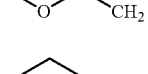 | O | |
| A791 | CF₂Cl | CH₂ | 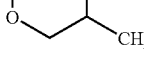 | O | |
| A792 | CF₂Cl | CH₂ | 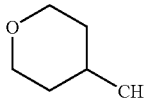 | O | |
| A793 | CF₂Cl | CH₂ | 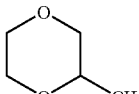 | O | |
| A794 | CF₂Cl | CH₂ | 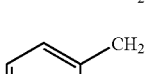 | O | |
| A795 | CF₂Cl | CH₂ | 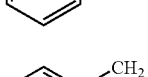 | O | |
| A796 | CF₂Cl | CH₂ | 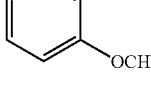 | O | |
| A797 | CF₂Cl | CH₂ | 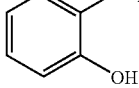 | O | |
| A798 | CF₂Cl | CH₂ | 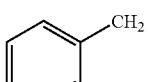 | O | |

-continued
| | | | | | |
|---|---|---|---|---|---|
| A799 | CF$_2$Cl | CH$_2$ | 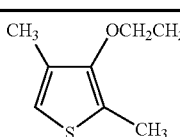 | | O |
| A800 | CF$_2$Cl | CH$_2$ | 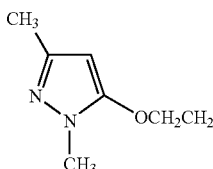 | | O |
| A801 | CF$_2$Cl | CH$_2$ | 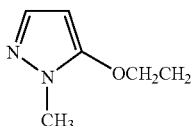 | | O |
| A802 | CF$_2$Cl | CH$_2$ | 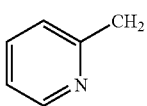 | | O |
| A803 | CF$_2$Cl | CH$_2$ | 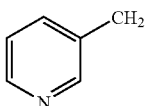 | | O |
| A804 | CF$_2$Cl | CH$_2$ | 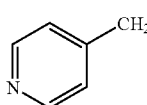 | | O |
| A805 | CF$_2$Cl | CH$_2$ | 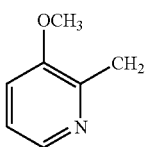 | | O |
| A806 | CF$_2$Cl | CH$_2$ | 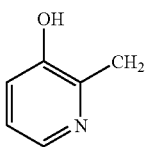 | | O |
| A807 | CF$_2$Cl | CH$_2$ | 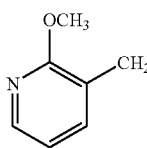 | | O |
| A808 | CF$_2$Cl | CH$_2$ | 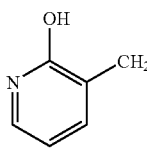 | | O |
| A809 | CF$_2$Cl | CH$_2$ | 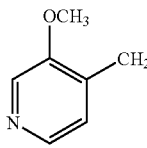 | | O |

-continued

| | | | | |
|---|---|---|---|---|
| A810 | CF₂Cl | CH₂ | 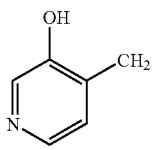 | O |
| A811 | CF₂Cl | CH₂ | 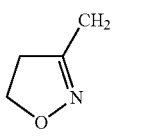 | O |
| A812 | CF₂Cl | CH₂ | 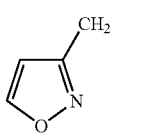 | O |
| A813 | CF₂Cl | CH₂ | 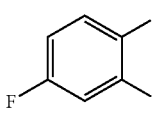 | O |
| A814 | CF₂Cl | CH₂ | 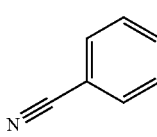 | O |
| A815 | CF₂Cl | CH₂ | 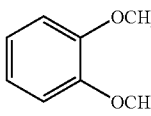 | O |
| A816 | CF₂Cl | CH₂ | 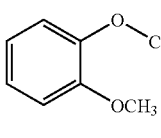 | O |
| A817 | CF₃ | CH₂ | CH₃SCH₂CH₂ | O |
| A818 | CF₃ | CH₂ | CH₃SOCH₂CH₂ | O |
| A819 | CF₃ | CH₂ | CH₃SO₂CH₂CH₂ | O |
| A820 | CF₃ | CH₂ | CH₃OCH₂CH₂ | O |
| A821 | CF₃ | CH₂ | CH₃OCH₂CH₂ | O |
| A822 | CF₃ | CH₂ | CH₃OCH₂CH₂ | O |
| A823 | CF₃ | CH₂ | CH₃OCH₂CH₂ | O |
| A824 | CF₃ | CH₂ | CH₃OCH₂CH₂ | O |
| A825 | CF₃ | CH₂ | CH₃OCH₂CH₂ | S |
| A826 | CF₃ | CH₂ | CH₃OCH₂CH₂ | SO |
| A827 | CF₃ | CH₂ | CH₃OCH₂CH₂ | SO₂ |
| A828 | CF₃ | CH₂ | CH₃SO₂CH₂CH₂ | O |
| A829 | CF₃ | CH₂ | 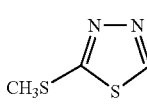 | S |
| A830 | CF₃ | CH₂ | 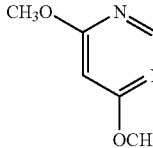 | S |

-continued

| | | | | |
|---|---|---|---|---|
| A831 | CF$_3$ | CH$_2$ | 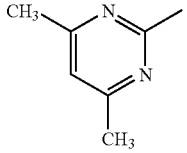 | S |
| A832 | CF$_3$ | CH$_2$ | 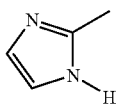 | S |
| A833 | CF$_3$ | CH$_2$ | CH$_3$C(O) | O |
| A834 | CF$_3$ | CH$_2$ | CF$_3$CH$_2$ | O |
| A835 | CF$_3$ | CH$_2$ | CH$_3$OCH$_2$CH$_2$OCH$_2$ | O |
| A836 | CF$_3$ | CH$_2$ | HC≡CCH$_2$ | O |
| A837 | CF$_3$ | CH$_2$ |  | O |
| A838 | CF$_3$ | CH$_2$ | CH$_3$CH$_2$C(OCH$_3$)HOCH$_2$CH$_2$ | O |
| A839 | CF$_3$ | CH$_2$ | (CH$_3$)$_3$CC(O) | O |
| A840 | CF$_3$ | CH$_2$ | CH$_2$=CHCH$_2$OCH$_2$ | O |
| A841 | CF$_3$ | CH$_2$ | CH$_3$CH$_2$CH$_2$OCH$_2$ | O |
| A842 | CF$_3$ | CH$_2$ | 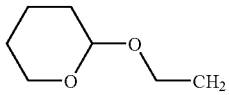 | O |
| A843 | CF$_3$ | CH$_2$ | n-heptyl-C(O) | O |
| A844 | CF$_3$ | CH$_2$ | phenyl-C(O) | O |
| A845 | CF$_3$ | CH$_2$ | CF$_3$CH$_2$OCH$_2$CH$_2$ | O |
| A846 | CF$_3$ | CH$_2$ | CH$_3$OCH$_2$CH$_2$ | O |
| A847 | CF$_3$ | CH$_2$ | HOCH$_2$CH$_2$ | O |
| A848 | CF$_3$ | CH$_2$ | 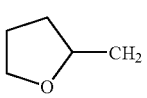 | O |
| A849 | CF$_3$ | CH$_2$ | N≡CCH$_2$CH$_2$ | O |
| A850 | CF$_3$ | CH$_2$ | ClCH$_2$CH$_2$ | O |
| A851 | CF$_3$ | CH$_2$ | 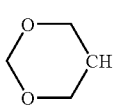 | O |
| A852 | CF$_3$ | CH$_2$ | 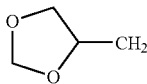 | O |
| A853 | CF$_3$ | CH$_2$ | CH$_3$OCH$_2$C(Br)HCH$_2$ | O |
| A854 | CF$_3$ | CH$_2$ | 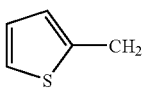 | O |
| A855 | CF$_3$ | CH$_2$ | 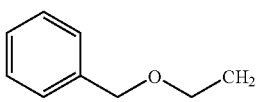 | O |
| A856 | CF$_3$ | CH$_2$ | HOCH$_2$CH$_2$ | O |
| A857 | CF$_3$ | CH$_2$ | 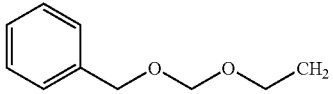 | O |

-continued

| | | | | |
|---|---|---|---|---|
| A858 | CF₃ | CH₂ | CH₃(OCH₂CH₂)₃ | O |
| A859 | CF₃ | CH₂ | CH₃CH₂OC(CH₃)HOCH₂CH₂ | O |
| A860 | CF₃ | CH₂ | n-heptyl-C(O)OCH₂CH₂ | O |
| A861 | CF₃ | CH₂ | CH₃C(O)OCH₂CH₂ | O |
| A862 | CF₃ | CH₂ | CH₃SO₂OCH₂CH₂ | O |
| A863 | CF₃ | CH₂ | 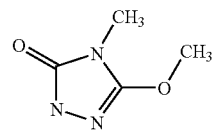 | O |
| A864 | CF₃ | CH₂ | CH₃ | —N(CH₃)SO₂— |
| A865 | CF₃ | CH₂ | HOCH₂C(OH)HCH₂ | O |
| A866 | CF₃ | CH₂ | phenyl-C(O)OCH₂CH₂ | O |
| A867 | CF₃ | CH₂ | tert-butyl-C(O)OCH₂CH₂ | O |
| A868 | CF₃ | CH₂ | CH₃OC(O)CH₂ | O |
| A869 | CF₃ | CH₂CH₂CH₂ | CH₃ | O |
| A870 | CF₃ | CH₂CH₂CH₂ | CH₂CH₃ | O |
| A871 | CF₂Cl | CH₂CH₂CH₂ | CH₃ | O |
| A872 | CF₂Cl | CH₂CH₂CH₂ | CH₂CH₃ | O |

The process according to the invention can be used especially advantageously for the preparation of the following compounds of Table 2:

In Table 2 which follows, the attachment position of the individual structures of the heterocycles of the group R₂ to the substituent R₁—X₁—, or to the C₁-C₄alkylene, C₂-C₄alkenyl-C₁-C₄alkylene, C₂-C₄alkynyl-C₁-C₄alkylene, —N(R₁₂)—C₁-C₄alkylene, —SO—C₁-C₄alkylene or —SO₂—C₁-C₄alkylene groups which connect the heterocycle of R₂ to the basic structure of formula I, is that nitrogen atom which is located at the same geometric position as is indicated in the Example below.

For example, the attachment position of the group

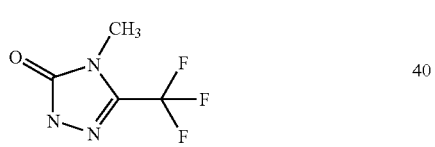

in the case of compound A 1.001 is the position indicated by an arrow:

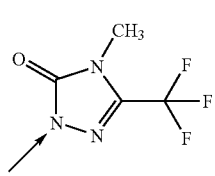

The free valencies in those structures represent terminal CH₃ groups, as in the case of, for example, the structure

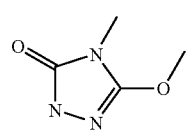

which may also be depicted as follows:

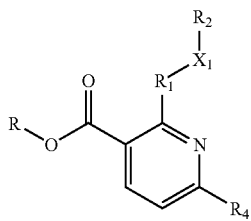

TABLE 2

Compounds of formula Ia wherein R is either methyl or ethyl:

(Ia)

| Comp. no. | R₄ | —R₁— | —X₁—R₂ |
|---|---|---|---|
| A1.001 | CF₂Cl | CH₂ | 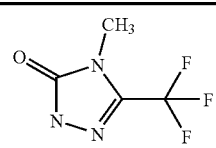 |
| A1.002 | CF₂H | CH₂ | 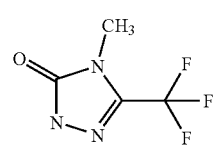 |
| A1.003 | CF₃ | CH₂ | 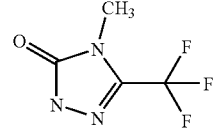 |

TABLE 2-continued

Compounds of formula Ia wherein R is either methyl or ethyl:

(Ia)

| Comp. no. | R$_4$ | —R$_1$— | —X$_1$—R$_2$ |
|---|---|---|---|
| A1.004 | CF$_3$ | CH$_2$OCH$_2$CH$_2$ | 4-methyl-5-(trifluoromethyl)-2,4-dihydro-3H-1,2,4-triazol-3-one |
| A1.005 | CF$_2$Cl | CH$_2$OCH$_2$CH$_2$ | 4-methyl-5-(trifluoromethyl)-2,4-dihydro-3H-1,2,4-triazol-3-one |
| A1.006 | CHF$_2$ | CH$_2$OCH$_2$CH$_2$ | 4-methyl-5-(trifluoromethyl)-2,4-dihydro-3H-1,2,4-triazol-3-one |
| A1.007 | CF$_3$ | CH$_2$ | 4,5-dimethyl-2,4-dihydro-3H-1,2,4-triazol-3-one |
| A1.008 | CF$_2$Cl | CH$_2$ | 4,5-dimethyl-2,4-dihydro-3H-1,2,4-triazol-3-one |
| A1.009 | CHF$_2$ | CH$_2$ | 4,5-dimethyl-2,4-dihydro-3H-1,2,4-triazol-3-one |
| A1.010 | CF$_3$ | CH$_2$OCH$_2$CH$_2$ | 4,5-dimethyl-2,4-dihydro-3H-1,2,4-triazol-3-one |
| A1.011 | CF$_2$Cl | CH$_2$OCH$_2$CH$_2$ | 4,5-dimethyl-2,4-dihydro-3H-1,2,4-triazol-3-one |
| A1.012 | CHF$_2$ | CH$_2$OCH$_2$CH$_2$ | 4,5-dimethyl-2,4-dihydro-3H-1,2,4-triazol-3-one |
| A1.013 | CF$_3$ | CH$_2$ | 5-ethyl-4-methyl-2,4-dihydro-3H-1,2,4-triazol-3-one |
| A1.014 | CF$_2$Cl | CH$_2$ | 5-ethyl-4-methyl-2,4-dihydro-3H-1,2,4-triazol-3-one |
| A1.015 | CHF$_2$ | CH$_2$ | 5-ethyl-4-methyl-2,4-dihydro-3H-1,2,4-triazol-3-one |
| A1.016 | CF$_3$ | CH$_2$OCH$_2$CH$_2$ | 5-ethyl-4-methyl-2,4-dihydro-3H-1,2,4-triazol-3-one |
| A1.017 | CF$_2$Cl | CH$_2$OCH$_2$CH$_2$ | 5-ethyl-4-methyl-2,4-dihydro-3H-1,2,4-triazol-3-one |
| A1.018 | CHF$_2$ | CH$_2$OCH$_2$CH$_2$ | 5-ethyl-4-methyl-2,4-dihydro-3H-1,2,4-triazol-3-one |
| A1.019 | CF$_3$ | CH$_2$ | 5-methoxy-4-methyl-2,4-dihydro-3H-1,2,4-triazol-3-one |

TABLE 2-continued

Compounds of formula Ia wherein R is either methyl or ethyl:

(Ia)

| Comp. no. | R₄ | —R₁— | —X₁—R₂ |
|---|---|---|---|
| A1.020 | CF₂Cl | CH₂ | (4-methyl-5-methoxy-1,2,4-triazol-3(4H)-one) |
| A1.021 | CHF₂ | CH₂ | (4-methyl-5-methoxy-1,2,4-triazol-3(4H)-one) |
| A1.022 | CF₃ | CH₂OCH₂ | (4-methyl-5-methoxy-1,2,4-triazol-3(4H)-one) |
| A1.023 | CF₂Cl | CH₂OCH₂ | (4-methyl-5-methoxy-1,2,4-triazol-3(4H)-one) |
| A1.024 | CHF₂ | CH₂OCH₂ | (4-methyl-5-methoxy-1,2,4-triazol-3(4H)-one) |
| A1.025 | CF₃ | CH₂ | (4-ethyl-5-methoxy-1,2,4-triazol-3(4H)-one) |
| A1.026 | CF₂Cl | CH₂ | (4-ethyl-5-methoxy-1,2,4-triazol-3(4H)-one) |
| A1.027 | CHF₂ | CH₂ | (4-ethyl-5-methoxy-1,2,4-triazol-3(4H)-one) |
| A1.028 | CF₃ | CH₂OCH₂ | (4-ethyl-5-methoxy-1,2,4-triazol-3(4H)-one) |
| A1.029 | CF₂Cl | CH₂OCH₂ | (4-ethyl-5-methoxy-1,2,4-triazol-3(4H)-one) |
| A1.030 | CHF₂ | CH₂OCH₂ | (4-ethyl-5-methoxy-1,2,4-triazol-3(4H)-one) |
| A1.031 | CF₃ | CH₂ | (4-cyclopropyl-5-methoxy-1,2,4-triazol-3(4H)-one) |
| A1.032 | CF₂Cl | CH₂ | (4-cyclopropyl-5-methoxy-1,2,4-triazol-3(4H)-one) |
| A1.033 | CHF₂ | CH₂ | (4-cyclopropyl-5-methoxy-1,2,4-triazol-3(4H)-one) |
| A1.034 | CF₃ | CH₂OCH₂ | (4-cyclopropyl-5-methoxy-1,2,4-triazol-3(4H)-one) |

TABLE 2-continued

Compounds of formula Ia wherein R is either methyl or ethyl:

(Ia)

| Comp. no. | R₄ | —R₁— | —X₁—R₂ |
|---|---|---|---|
| A1.035 | CF₂Cl | CH₂OCH₂CH₂ | 4-cyclopropyl-5-methoxy-2,4-dihydro-3H-1,2,4-triazol-3-one |
| A1.036 | CHF₂ | CH₂OCH₂CH₂ | 4-cyclopropyl-5-methoxy-2,4-dihydro-3H-1,2,4-triazol-3-one |
| A1.037 | CF₃ | CH₂ | 5-ethoxy-4-methyl-2,4-dihydro-3H-1,2,4-triazol-3-one |
| A1.038 | CF₂Cl | CH₂ | 5-ethoxy-4-methyl-2,4-dihydro-3H-1,2,4-triazol-3-one |
| A1.039 | CHF₂ | CH₂ | 5-ethoxy-4-methyl-2,4-dihydro-3H-1,2,4-triazol-3-one |
| A1.040 | CF₃ | CH₂OCH₂CH₂ | 5-ethoxy-4-methyl-2,4-dihydro-3H-1,2,4-triazol-3-one |
| A1.041 | CF₂Cl | CH₂OCH₂CH₂ | 5-ethoxy-4-methyl-2,4-dihydro-3H-1,2,4-triazol-3-one |
| A1.042 | CHF₂ | CH₂OCH₂CH₂ | 5-ethoxy-4-methyl-2,4-dihydro-3H-1,2,4-triazol-3-one |
| A1.043 | CF₃ | CH₂ | 5-ethoxy-4-ethyl-2,4-dihydro-3H-1,2,4-triazol-3-one |
| A1.044 | CF₂Cl | CH₂ | 5-ethoxy-4-ethyl-2,4-dihydro-3H-1,2,4-triazol-3-one |
| A1.045 | CHF₂ | CH₂ | 5-ethoxy-4-ethyl-2,4-dihydro-3H-1,2,4-triazol-3-one |
| A1.046 | CF₃ | CH₂OCH₂CH₂ | 5-ethoxy-4-ethyl-2,4-dihydro-3H-1,2,4-triazol-3-one |
| A1.047 | CF₂Cl | CH₂OCH₂CH₂ | 5-ethoxy-4-ethyl-2,4-dihydro-3H-1,2,4-triazol-3-one |
| A1.048 | CHF₂ | CH₂OCH₂CH₂ | 5-ethoxy-4-ethyl-2,4-dihydro-3H-1,2,4-triazol-3-one |
| A1.049 | CF₃ | CH₂ | 4-cyclopropyl-5-ethoxy-2,4-dihydro-3H-1,2,4-triazol-3-one |
| A1.050 | CF₂Cl | CH₂ | 4-cyclopropyl-5-ethoxy-2,4-dihydro-3H-1,2,4-triazol-3-one |

TABLE 2-continued

Compounds of formula Ia wherein R is either methyl or ethyl:

(Ia)

| Comp. no. | R₄ | —R₁— | —X₁—R₂ |
|---|---|---|---|
| A1.051 | CHF₂ | CH₂ | 4-cyclopropyl-5-ethoxy-4H-1,2,4-triazol-3(2H)-one |
| A1.052 | CF₃ | CH₂OCH₂CH₂ | 4-cyclopropyl-5-ethoxy-4H-1,2,4-triazol-3(2H)-one |
| A1.053 | CF₂Cl | CH₂OCH₂CH₂ | 4-cyclopropyl-5-ethoxy-4H-1,2,4-triazol-3(2H)-one |
| A1.054 | CHF₂ | CH₂OCH₂CH₂ | 4-cyclopropyl-5-ethoxy-4H-1,2,4-triazol-3(2H)-one |
| A1.055 | CF₃ | CH₂ | S-methyl 5-methyl-3-oxo-2,3-dihydro-1H-pyrazole-1-carbothioate |
| A1.056 | CF₂Cl | CH₂ | S-methyl 5-methyl-3-oxo-2,3-dihydro-1H-pyrazole-1-carbothioate |
| A1.057 | CHF₂ | CH₂ | S-methyl 5-methyl-3-oxo-2,3-dihydro-1H-pyrazole-1-carbothioate |
| A1.058 | CF₃ | CH₂OCH₂CH₂ | S-methyl 5-methyl-3-oxo-2,3-dihydro-1H-pyrazole-1-carbothioate |
| A1.059 | CF₂Cl | CH₂OCH₂CH₂ | S-methyl 5-methyl-3-oxo-2,3-dihydro-1H-pyrazole-1-carbothioate |
| A1.060 | CHF₂ | CH₂OCH₂CH₂ | S-methyl 5-methyl-3-oxo-2,3-dihydro-1H-pyrazole-1-carbothioate |
| A1.061 | CF₃ | CH₂ | 5-methyl-5-phenyl-4,5-dihydro-1H-imidazol-4-one |
| A1.062 | CF₂Cl | CH₂ | 5-methyl-5-phenyl-4,5-dihydro-1H-imidazol-4-one |

TABLE 2-continued

Compounds of formula Ia wherein R is either methyl or ethyl:

(Ia)

| Comp. no. | R₄ | —R₁— | —X₁—R₂ |
|---|---|---|---|
| A1.063 | CHF₂ | CH₂ | (methyl-phenyl-imidazolinone) |
| A1.064 | CF₃ | CH₂OCH₂CH₂ | (methyl-phenyl-imidazolinone) |
| A1.065 | CF₂Cl | CH₂OCH₂CH₂ | (methyl-phenyl-imidazolinone) |
| A1.066 | CHF₂ | CH₂OCH₂CH₂ | (methyl-phenyl-imidazolinone) |
| A1.067 | CF₃ | CH₂ | (dimethyl-imidazolinone) |
| A1.068 | CF₂Cl | CH₂ | (dimethyl-imidazolinone) |
| A1.069 | CHF₂ | CH₂ | (dimethyl-imidazolinone) |
| A1.070 | CF₃ | CH₂OCH₂CH₂ | (dimethyl-imidazolinone) |
| A1.071 | CF₂Cl | CH₂OCH₂CH₂ | (dimethyl-imidazolinone) |
| A1.072 | CHF₂ | CH₂OCH₂CH₂ | (dimethyl-imidazolinone) |
| A1.073 | CF₃ | CH₂ | (methyl-triazolinone) |
| A1.074 | CF₂Cl | CH₂ | (methyl-triazolinone) |
| A1.075 | CHF₂ | CH₂ | (methyl-triazolinone) |
| A1.076 | CF₃ | CH₂OCH₂CH₂ | (methyl-triazolinone) |
| A1.077 | CF₂Cl | CH₂OCH₂CH₂ | (methyl-triazolinone) |
| A1.078 | CHF₂ | CH₂OCH₂CH₂ | (methyl-triazolinone) |

TABLE 2-continued

Compounds of formula Ia wherein R is either methyl or ethyl:

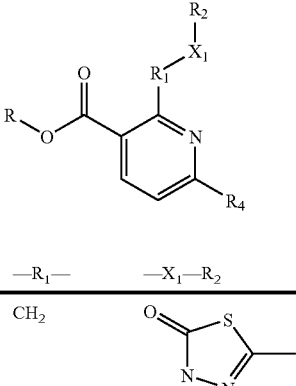
(Ia)

| Comp. no. | $R_4$ | —$R_1$— | —$X_1$—$R_2$ |
|---|---|---|---|
| A1.079 | $CF_3$ | $CH_2$ | 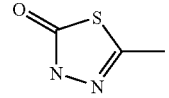 |
| A1.080 | $CF_2Cl$ | $CH_2$ | 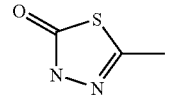 |
| A1.081 | $CHF_2$ | $CH_2$ | 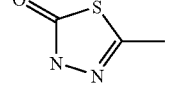 |
| A1.082 | $CF_3$ | $CH_2OCH_2CH_2$ | 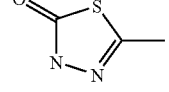 |
| A1.083 | $CF_2Cl$ | $CH_2OCH_2CH_2$ | 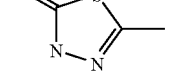 |
| A1.084 | $CHF_2$ | $CH_2OCH_2CH_2$ | 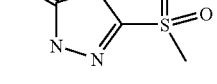 |
| A1.085 | $CF_3$ | $CH_2$ | 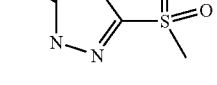 |
| A1.086 | $CF_2Cl$ | $CH_2$ | 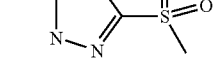 |
| A1.087 | $CHF_2$ | $CH_2$ | 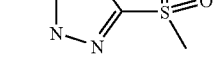 |
| A1.088 | $CF_3$ | $CH_2OCH_2CH_2$ | 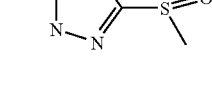 |
| A1.089 | $CF_2Cl$ | $CH_2OCH_2CH_2$ | 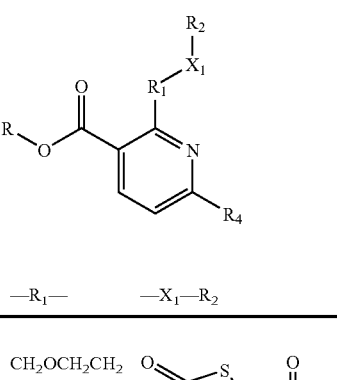 |
| A1.090 | $CHF_2$ | $CH_2OCH_2CH_2$ | 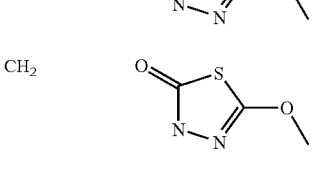 |
| A1.091 | $CF_3$ | $CH_2$ | 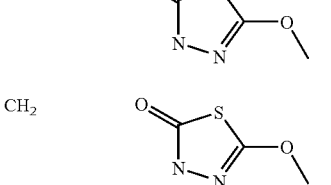 |
| A1.092 | $CF_2Cl$ | $CH_2$ | 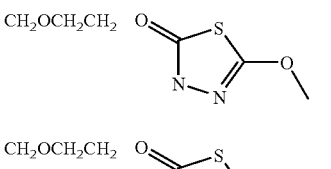 |
| A1.093 | $CHF_2$ | $CH_2$ | 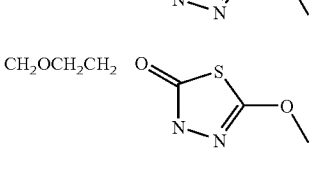 |
| A1.094 | $CF_3$ | $CH_2OCH_2CH_2$ | 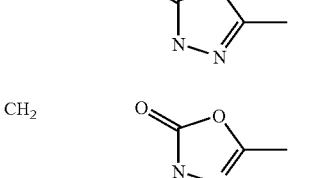 |
| A1.095 | $CF_2Cl$ | $CH_2OCH_2CH_2$ | 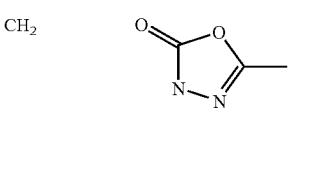 |
| A1.096 | $CHF_2$ | $CH_2OCH_2CH_2$ | 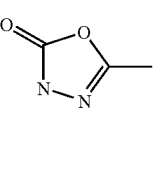 |
| A1.097 | $CF_3$ | $CH_2$ | 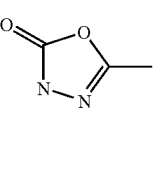 |
| A1.098 | $CF_2Cl$ | $CH_2$ | 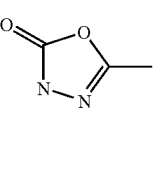 |
| A1.099 | $CHF_2$ | $CH_2$ | |

TABLE 2-continued

Compounds of formula Ia wherein R is either methyl or ethyl:

(Ia)

| Comp. no. | R₄ | —R₁— | —X₁—R₂ |
|---|---|---|---|
| A1.100 | CF₃ | CH₂OCH₂CH₂ | 5-methyl-1,3,4-oxadiazol-2(3H)-one |
| A1.101 | CF₂Cl | CH₂OCH₂CH₂ | 5-methyl-1,3,4-oxadiazol-2(3H)-one |
| A1.102 | CHF₂ | CH₂OCH₂CH₂ | 5-methyl-1,3,4-oxadiazol-2(3H)-one |
| A1.103 | CF₃ | CH₂ | 5-(trifluoromethyl)-1,3,4-oxadiazol-2(3H)-one |
| A1.104 | CF₂Cl | CH₂ | 5-(trifluoromethyl)-1,3,4-oxadiazol-2(3H)-one |
| A1.105 | CHF₂ | CH₂ | 5-(trifluoromethyl)-1,3,4-oxadiazol-2(3H)-one |
| A1.106 | CF₃ | CH₂OCH₂CH₂ | 5-(trifluoromethyl)-1,3,4-oxadiazol-2(3H)-one |
| A1.107 | CF₂Cl | CH₂OCH₂CH₂ | 5-(trifluoromethyl)-1,3,4-oxadiazol-2(3H)-one |
| A1.108 | CHF₂ | CH₂OCH₂CH₂ | 5-(trifluoromethyl)-1,3,4-oxadiazol-2(3H)-one |
| A1.109 | CF₃ | CH₂ | isothiazol-3(2H)-one |
| A1.110 | CF₂Cl | CH₂ | isothiazol-3(2H)-one |
| A1.111 | CHF₂ | CH₂ | isothiazol-3(2H)-one |
| A1.112 | CF₃ | CH₂OCH₂CH₂ | isothiazol-3(2H)-one |
| A1.113 | CF₂Cl | CH₂OCH₂CH₂ | isothiazol-3(2H)-one |
| A1.114 | CHF₂ | CH₂OCH₂CH₂ | isothiazol-3(2H)-one |
| A1.115 | CF₃ | CH₂ | 5-chloroisothiazol-3(2H)-one |
| A1.116 | CF₂Cl | CH₂ | 5-chloroisothiazol-3(2H)-one |
| A1.117 | CHF₂ | CH₂ | 5-chloroisothiazol-3(2H)-one |
| A1.118 | CF₃ | CH₂OCH₂CH₂ | 5-chloroisothiazol-3(2H)-one |
| A1.119 | CF₂Cl | CH₂OCH₂CH₂ | 5-chloroisothiazol-3(2H)-one |
| A1.120 | CHF₂ | CH₂OCH₂CH₂ | 5-chloroisothiazol-3(2H)-one |

TABLE 2-continued

Compounds of formula Ia wherein R is either methyl or ethyl:

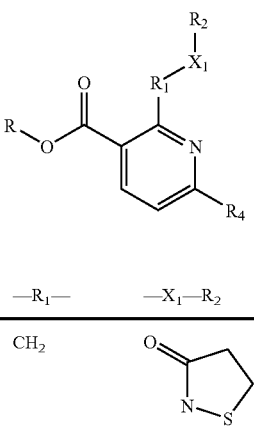
(Ia)

| Comp. no. | R$_4$ | —R$_1$— | —X$_1$—R$_2$ |
|---|---|---|---|
| A1.121 | CF$_3$ | CH$_2$ | 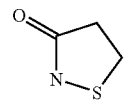 |
| A1.122 | CF$_2$Cl | CH$_2$ | 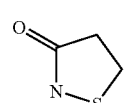 |
| A1.123 | CHF$_2$ | CH$_2$ | 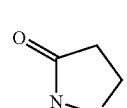 |
| A1.124 | CF$_3$ | CH$_2$OCH$_2$ | 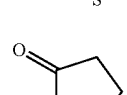 |
| A1.125 | CF$_2$Cl | CH$_2$OCH$_2$ | 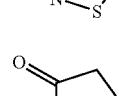 |
| A1.126 | CHF$_2$ | CH$_2$OCH$_2$ | 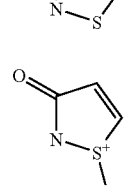 |
| A1.127 | CF$_3$ | CH$_2$ | 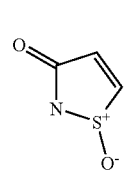 |
| A1.128 | CF$_2$Cl | CH$_2$ | 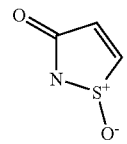 |
| A1.129 | CHF$_2$ | CH$_2$ | 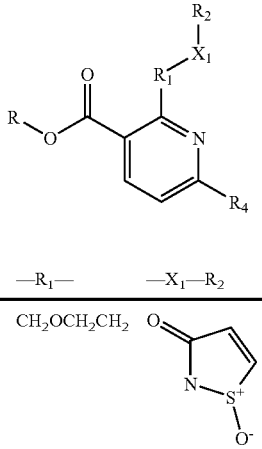 |

TABLE 2-continued

Compounds of formula Ia wherein R is either methyl or ethyl:

(Ia)

| Comp. no. | R$_4$ | —R$_1$— | —X$_1$—R$_2$ |
|---|---|---|---|
| A1.130 | CF$_3$ | CH$_2$OCH$_2$ | 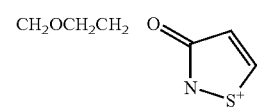 |
| A1.131 | CF$_2$Cl | CH$_2$OCH$_2$ | 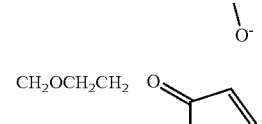 |
| A1.132 | CHF$_2$ | CH$_2$OCH$_2$ | 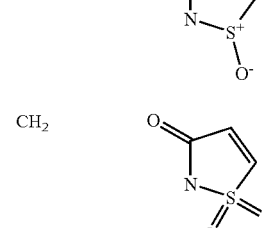 |
| A1.133 | CF$_3$ | CH$_2$ | 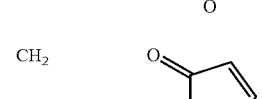 |
| A1.134 | CF$_2$Cl | CH$_2$ | 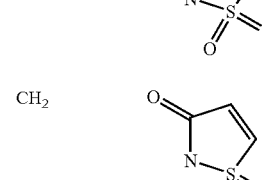 |
| A1.135 | CHF$_2$ | CH$_2$ | 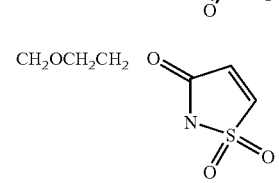 |
| A1.136 | CF$_3$ | CH$_2$OCH$_2$ | 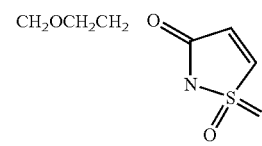 |
| A1.137 | CF$_2$Cl | CH$_2$OCH$_2$ | |

TABLE 2-continued

Compounds of formula Ia wherein R is either methyl or ethyl:

(Ia)

| Comp. no. | R₄ | —R₁— | —X₁—R₂ |
|---|---|---|---|
| A1.138 | CHF₂ | CH₂OCH₂CH₂ | 3-oxo-isothiazoline (S,S-dioxide) |
| A1.139 | CF₃ | CH₂ | 3-oxo-isoxazole |
| A1.140 | CF₂Cl | CH₂ | 3-oxo-isoxazole |
| A1.141 | CHF₂ | CH₂ | 3-oxo-isoxazole |
| A1.142 | CF₃ | CH₂OCH₂CH₂ | 3-oxo-isoxazole |
| A1.143 | CF₂Cl | CH₂OCH₂CH₂ | 3-oxo-isoxazole |
| A1.144 | CHF₂ | CH₂OCH₂CH₂ | 3-oxo-isoxazole |
| A1.145 | CF₃ | CH₂ | 3-oxo-isoxazolidine |
| A1.146 | CF₂Cl | CH₂ | 3-oxo-isoxazolidine |
| A1.147 | CHF₂ | CH₂ | 3-oxo-isoxazolidine |
| A1.148 | CF₃ | CH₂OCH₂CH₂ | 3-oxo-isoxazolidine |
| A1.149 | CF₂Cl | CH₂OCH₂CH₂ | 3-oxo-isoxazolidine |
| A1.150 | CHF₂ | CH₂OCH₂CH₂ | 3-oxo-isoxazolidine |
| A1.151 | CF₃ | CH₂ | 4-methyl-5-propoxy-3-oxo-1,2,4-triazole |
| A1.152 | CF₂Cl | CH₂ | 4-methyl-5-propoxy-3-oxo-1,2,4-triazole |
| A1.153 | CHF₂ | CH₂ | 4-methyl-5-propoxy-3-oxo-1,2,4-triazole |
| A1.154 | CF₃ | CH₂OCH₂CH₂ | 4-methyl-5-propoxy-3-oxo-1,2,4-triazole |
| A1.155 | CF₂Cl | CH₂OCH₂CH₂ | 4-methyl-5-propoxy-3-oxo-1,2,4-triazole |
| A1.156 | CHF₂ | CH₂OCH₂CH₂ | 4-methyl-5-propoxy-3-oxo-1,2,4-triazole |

TABLE 2-continued

Compounds of formula Ia wherein R is either methyl or ethyl:

(Ia)

| Comp. no. | R₄ | —R₁— | —X₁—R₂ |
|---|---|---|---|
| A1.157 | CF₃ | CH₂ | 4-CHF₂-5-methyl-1,2,4-triazol-3(4H)-one |
| A1.158 | CF₂Cl | CH₂ | 4-CHF₂-5-methyl-1,2,4-triazol-3(4H)-one |
| A1.159 | CHF₂ | CH₂ | 4-CHF₂-5-methyl-1,2,4-triazol-3(4H)-one |
| A1.160 | CF₃ | CH₂OCH₂ | 4-CHF₂-5-methyl-1,2,4-triazol-3(4H)-one |
| A1.161 | CF₂Cl | CH₂OCH₂ | 4-CHF₂-5-methyl-1,2,4-triazol-3(4H)-one |
| A1.162 | CHF₂ | CH₂OCH₂ | 4-CHF₂-5-methyl-1,2,4-triazol-3(4H)-one |
| A1.163 | CF₃ | CH₂ | 3-phenyl-2,3-dihydro-imidazol-2-one |
| A1.164 | CF₂Cl | CH₂ | 3-phenyl-2,3-dihydro-imidazol-2-one |
| A1.165 | CHF₂ | CH₂ | 3-phenyl-2,3-dihydro-imidazol-2-one |
| A1.166 | CF₃ | CH₂OCH₂ | 3-phenyl-2,3-dihydro-imidazol-2-one |
| A1.167 | CF₂Cl | CH₂OCH₂ | 3-phenyl-2,3-dihydro-imidazol-2-one |
| A1.168 | CHF₂ | CH₂OCH₂ | 3-phenyl-2,3-dihydro-imidazol-2-one |
| A1.169 | CF₃ | CH₂ | 3-tert-butyl-5-methyl-imidazolidine-2,4-dione |

TABLE 2-continued
Compounds of formula Ia wherein R is either methyl or ethyl:
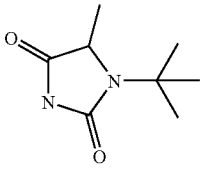
(Ia)
| Comp. no. | R₄ | —R₁— | —X₁—R₂ |
|---|---|---|---|
| A1.170 | CF₂Cl | CH₂ | 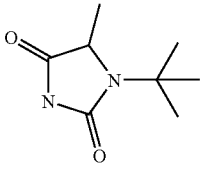 |
| A1.171 | CHF₂ | CH₂ | 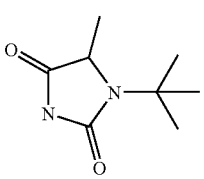 |
| A1.172 | CF₃ | CH₂OCH₂CH₂ | 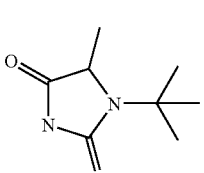 |
| A1.173 | CF₂Cl | CH₂OCH₂CH₂ | 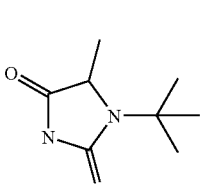 |
| A1.174 | CHF₂ | CH₂OCH₂CH₂ | 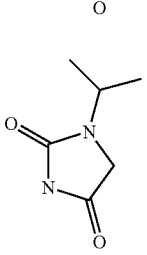 |
| A1.175 | CF₃ | CH₂ | 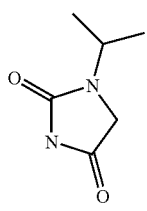 |
| A1.176 | CF₂Cl | CH₂ | 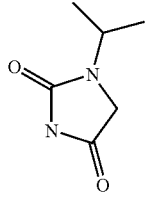 |
| A1.177 | CHF₂ | CH₂ | 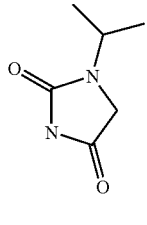 |
| A1.178 | CF₃ | CH₂OCH₂CH₂ | 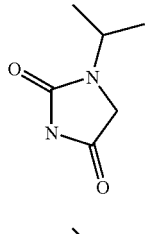 |
| A1.179 | CF₂Cl | CH₂OCH₂CH₂ | 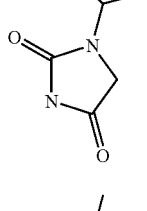 |
| A1.180 | CHF₂ | CH₂OCH₂CH₂ | 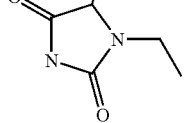 |
| A1.181 | CF₃ | CH₂ |  |

TABLE 2-continued

Compounds of formula Ia wherein R is either methyl or ethyl:

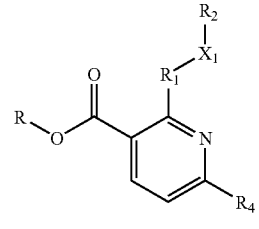 (Ia)

| Comp. no. | R₄ | —R₁— | —X₁—R₂ |
|---|---|---|---|
| A1.182 | CF₂Cl | CH₂ | 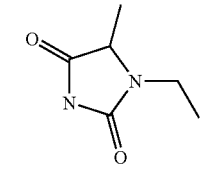 |
| A1.183 | CHF₂ | CH₂ | 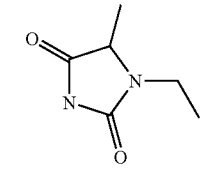 |
| A1.184 | CF₃ | CH₂OCH₂CH₂ | 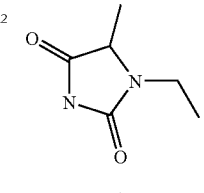 |
| A1.185 | CF₂Cl | CH₂OCH₂CH₂ | 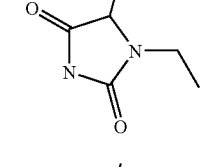 |
| A1.186 | CHF₂ | CH₂OCH₂CH₂ | 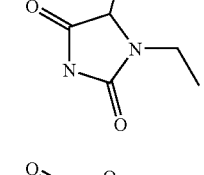 |
| A1.187 | CF₃ | CH₂ | 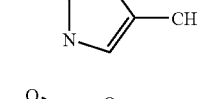 |
| A1.188 | CF₂Cl | CH₂ | 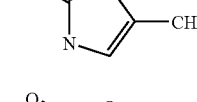 |
| A1.189 | CHF₂ | CH₂ | 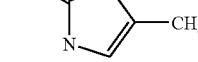 |

TABLE 2-continued

Compounds of formula Ia wherein R is either methyl or ethyl:

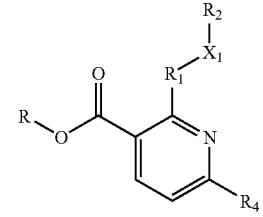 (Ia)

| Comp. no. | R₄ | —R₁— | —X₁—R₂ |
|---|---|---|---|
| A1.190 | CF₃ | CH₂OCH₂CH₂ | 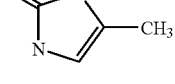 |
| A1.191 | CF₂Cl | CH₂OCH₂CH₂ | 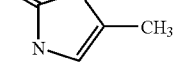 |
| A1.192 | CHF₂ | CH₂OCH₂CH₂ | 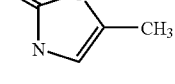 |
| A1.193 | CF₃ | CH₂ | 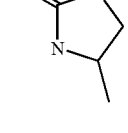 |
| A1.194 | CF₂Cl | CH₂ | 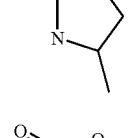 |
| A1.195 | CHF₂ | CH₂ | 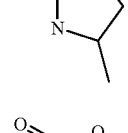 |
| A1.196 | CF₃ | CH₂OCH₂CH₂ | 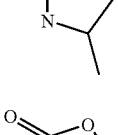 |
| A1.197 | CF₂Cl | CH₂OCH₂CH₂ |  |
| A1.198 | CHF₂ | CH₂OCH₂CH₂ |  |

TABLE 2-continued

Compounds of formula Ia wherein R is either methyl or ethyl:

(Ia)

| Comp. no. | R$_4$ | —R$_1$— | —X$_1$—R$_2$ |
|---|---|---|---|
| A1.199 | CF$_3$ | CH$_2$ | 6-Cl-benzoxazol-2(3H)-one-3-yl |
| A1.200 | CF$_2$Cl | CH$_2$ | 6-Cl-benzoxazol-2(3H)-one-3-yl |
| A1.201 | CHF$_2$ | CH$_2$ | 6-Cl-benzoxazol-2(3H)-one-3-yl |
| A1.202 | CF$_3$ | CH$_2$ | 1-methyl-2-thioxoimidazolidin-3-yl |
| A1.203 | CF$_2$Cl | CH$_2$ | 1-methyl-2-thioxoimidazolidin-3-yl |
| A1.204 | CHF$_2$ | CH$_2$ | 1-methyl-2-thioxoimidazolidin-3-yl |
| A1.205 | CF$_3$ | CH$_2$OCH$_2$ | 1-methyl-2-thioxoimidazolidin-3-yl |
| A1.206 | CF$_2$Cl | CH$_2$OCH$_2$ | 1-methyl-2-thioxoimidazolidin-3-yl |
| A1.207 | CHF$_2$ | CH$_2$OCH$_2$ | 1-methyl-2-thioxoimidazolidin-3-yl |
| A1.208 | CF$_3$ | CH$_2$ | 4-isopropyl-1-phenyl-1H-imidazol-2(3H)-one-3-yl |
| A1.209 | CF$_3$ | CH$_2$ | 5-chloro-2,6-dimethylpyrimidin-4(3H)-one-3-yl |
| A1.210 | CHF$_2$ | CH$_2$ | 5-chloro-2,6-dimethylpyrimidin-4(3H)-one-3-yl |
| A1.211 | CF$_3$ | CH$_2$ | 2,4-dimethyl-1,2,4-triazolidine-3,5-dione-1-yl |
| A1.212 | CHF$_2$ | CH$_2$ | 2,4-dimethyl-1,2,4-triazolidine-3,5-dione-1-yl |

TABLE 2-continued

Compounds of formula Ia wherein R is either methyl or ethyl:

(Ia)

| Comp. no. | R$_4$ | —R$_1$— | —X$_1$—R$_2$ |
|---|---|---|---|
| A1.213 | CF$_3$ | CH$_2$ | 1-methyl-imidazolidin-2-one-3-yl |
| A1.214 | CF$_2$Cl | CH$_2$ | 1-methyl-imidazolidin-2-one-3-yl |
| A1.215 | CHF$_2$ | CH$_2$ | 1-methyl-imidazolidin-2-one-3-yl |
| A1.216 | CF$_3$ | CH$_2$OCH$_2$CH$_2$ | 1-methyl-imidazolidin-2-one-3-yl |
| A1.217 | CF$_2$Cl | CH$_2$OCH$_2$CH$_2$ | 1-methyl-imidazolidin-2-one-3-yl |
| A1.218 | CHF$_2$ | CH$_2$OCH$_2$CH$_2$ | 1-methyl-imidazolidin-2-one-3-yl |
| A1.219 | CF$_3$ | CH$_2$ | pyrrolidin-2-one-1-yl |
| A1.220 | CF$_3$ | CH$_2$OCH$_2$CH$_2$ | pyrrolidin-2-one-1-yl |
| A1.221 | CF$_3$ | CH$_2$ | azetidin-2-one-1-yl |
| A1.222 | CF$_3$ | CH$_2$ | 3-methyl-pyrrolidin-2-one-1-yl |
| A1.223 | CF$_3$ | CH$_2$ | 5-methyl-pyrrolidin-2-one-1-yl |
| A1.224 | CF$_3$ | CH$_2$ | piperidin-2-one-1-yl |
| A1.225 | CClF$_2$ | CH$_2$ | pyrrolidin-2-one-1-yl |
| A1.226 | CClF$_2$ | CH$_2$ | azetidin-2-one-1-yl |
| A1.227 | CClF$_2$ | CH$_2$ | 3-methyl-pyrrolidin-2-one-1-yl |
| A1.228 | CClF$_2$ | CH$_2$ | 5-methyl-pyrrolidin-2-one-1-yl |
| A1.229 | CClF$_2$ | CH$_2$ | piperidin-2-one-1-yl |
| A1.230 | CHF$_2$ | CH$_2$ | pyrrolidin-2-one-1-yl |
| A1.231 | CHF$_2$ | CH$_2$ | azetidin-2-one-1-yl |

TABLE 2-continued

Compounds of formula Ia wherein R is either methyl or ethyl:

(Ia)

| Comp. no. | $R_4$ | —$R_1$— | —$X_1$—$R_2$ |
|---|---|---|---|
| A1.232 | $CHF_2$ | $CH_2$ | 3-methyl-2-oxopyrrolidin-1-yl |
| A1.233 | $CHF_2$ | $CH_2$ | 5-methyl-2-oxopyrrolidin-1-yl |
| A1.234 | $CHF_2$ | $CH_2$ | 2-oxopiperidin-1-yl |
| A1.235 | $CF_3$ | $CH_2$ | 5-methyl-1-(3-trifluoromethylphenyl)-4-oxoimidazolidin-3-yl |
| A1.236 | $CHF_2$ | $CH_2$ | 5-methyl-1-(3-trifluoromethylphenyl)-4-oxoimidazolidin-3-yl |
| A1.237 | $CF_3$ | $CH_2$ | 1-(4-chlorophenyl)-4-oxoimidazolidin-3-yl |
| A1.238 | $CHF_2$ | $CH_2$ | 1-(4-chlorophenyl)-4-oxoimidazolidin-3-yl |
| A1.240 | $CF_3$ | $CH_2$ | 1-(3-trifluoromethylphenyl)-4-oxoimidazolidin-3-yl |
| A1.241 | $CHF_2$ | $CH_2$ | 1-(3-trifluoromethylphenyl)-4-oxoimidazolidin-3-yl |
| A1.242 | $CF_3$ | $CH_2$ | 1-methyl-5-oxo-1H-tetrazol-4(5H)-yl |
| A1.243 | $CF_3$ | $CH_2$ | 1-methyl-2-oxotetrahydropyrimidin-3-yl |
| A1.244 | $CF_3$ | $CH_2$ | 2-oxooxazolidin-3-yl |
| A1.245 | $CF_3$ | $CH_2$ | 5-methyl-2-oxo-1,3,4-thiadiazol-3(2H)-yl |

What is claimed is:

1. A process for the preparation of a compound of formula I (I)

wherein
R is methyl or ethyl;
$R_{05}$ is Hydrogen;
$R_1$ is —$CH_2$—, —$CH_2CH_2$—, —$CH_2CH_2CH_2$—, —$CF_2$—, —CH=$CHCH_2$—, —$CH(CH_3)$— or —C≡$CCH_2$—;
$R_4$ is trifluoromethyl, chlorodifluoromethyl or difluoromethyl;
$X_1$ is oxygen;
$R_2$ is $CH_3$, $CH_2CH_3$, $CH_2OCH_3$, $CH_2OCH_2CH_3$, $CH_2CH_2OCH_3$, $CH_2CH_2OCH_2CH_3$, $CH_2CF_3$, propargyl, cyclopropylmethyl, benzyl, $CH_2CH_2SO_2CH_3$ or $CH_2CH_2OCH_2CH_2OCH_3$;

which process
comprises reacting
a compound of formula II

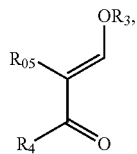
(II)

wherein $R_3$ is $C_1$-$C_8$alkyl or $C_3$-$C_6$cycloalkyl and $R_4$ and $R_{05}$ are as defined for formula I, with a compound of formula III

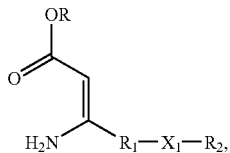
(III)

wherein R, $R_1$, $R_2$ and $X_1$ are as defined for formula I, in an inert solvent in the presence of a proton source.

2. A process according to claim 1, wherein there is prepared a compound of formula I wherein
$R_1$ is —$CH_2$—;
$R_4$ is trifluoromethyl;
$R_{05}$ is hydrogen;
$X_1$ is oxygen;
$R_2$ is $CH_2CH_2OCH_3$.

3. A compound of formula IIIa

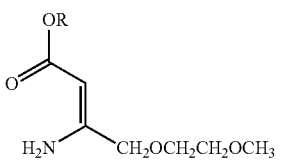
(IIIa)

wherein R is as defined for formula I in claim 1.

* * * * *